(12) United States Patent
Yoshida et al.

(10) Patent No.: US 10,160,721 B2
(45) Date of Patent: Dec. 25, 2018

(54) SALT AND PHOTORESIST COMPOSITION CONTAINING THE SAME

(71) Applicant: SUMITOMO CHEMICAL COMPANY, LIMITED, Tokyo (JP)

(72) Inventors: Isao Yoshida, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/690,568

(22) Filed: Aug. 30, 2017

(65) Prior Publication Data

US 2018/0065924 A1  Mar. 8, 2018

(30) Foreign Application Priority Data

Sep. 2, 2016 (JP) ................................. 2016-171968

(51) Int. Cl.
| | | |
|---|---|---|
| *C07C 309/17* | (2006.01) | |
| *C07C 309/07* | (2006.01) | |
| *G03F 7/039* | (2006.01) | |
| *G03F 7/004* | (2006.01) | |
| *G03F 7/038* | (2006.01) | |
| *G03F 7/16* | (2006.01) | |
| *G03F 7/20* | (2006.01) | |
| *G03F 7/32* | (2006.01) | |
| *G03F 7/38* | (2006.01) | |
| *C07D 317/72* | (2006.01) | |
| *C07D 319/08* | (2006.01) | |
| *C07D 321/10* | (2006.01) | |
| *C07D 327/06* | (2006.01) | |
| *C07D 327/08* | (2006.01) | |
| *C07C 309/12* | (2006.01) | |
| *C07D 333/46* | (2006.01) | |
| *C07D 335/02* | (2006.01) | |
| *C07C 381/12* | (2006.01) | |
| *C07F 7/08* | (2006.01) | |
| *C07D 307/33* | (2006.01) | |
| *C07D 307/77* | (2006.01) | |

(52) U.S. Cl.
CPC .......... *C07C 309/17* (2013.01); *C07C 309/07* (2013.01); *C07C 309/12* (2013.01); *C07C 381/12* (2013.01); *C07D 307/33* (2013.01); *C07D 307/77* (2013.01); *C07D 317/72* (2013.01); *C07D 319/08* (2013.01); *C07D 321/10* (2013.01); *C07D 327/06* (2013.01); *C07D 327/08* (2013.01); *C07D 333/46* (2013.01); *C07D 335/02* (2013.01); *C07F 7/08* (2013.01); *G03F 7/0045* (2013.01); *G03F 7/038* (2013.01); *G03F 7/0392* (2013.01); *G03F 7/16* (2013.01); *G03F 7/20* (2013.01); *G03F 7/322* (2013.01); *G03F 7/38* (2013.01); *C07C 2601/14* (2017.05); *C07C 2602/42* (2017.05); *C07C 2603/74* (2017.05); *C07C 2603/98* (2017.05)

(58) Field of Classification Search
CPC .......... G03F 7/0392; G03F 7/38; G03F 7/322; G03F 7/20; G03F 7/16; G03F 7/0045; C07C 309/17; C07C 309/07
See application file for complete search history.

(56) References Cited

U.S. PATENT DOCUMENTS

| | | | |
|---|---|---|---|
| 9,663,656 B2 * | 5/2017 | Hatakeyama | ........... C08L 81/02 |
| 2007/0100096 A1 | 5/2007 | Harada et al. | |
| 2007/0149702 A1 | 6/2007 | Ando et al. | |
| 2013/0209938 A1 * | 8/2013 | Takihana | .............. C07C 309/10 |
| | | | 430/285.1 |
| 2016/0075875 A1 * | 3/2016 | Hatakeyama | ........... C08L 33/16 |
| | | | 252/500 |

FOREIGN PATENT DOCUMENTS

JP    2013-82893 A    5/2013

OTHER PUBLICATIONS

"sulfonium compounds" from PAC, 1995, 67, 1307 (Glossary of class names of organic compounds and reactivity intermediates based on structure (IUPAC Recommendations 1995)) on p. 1369. obtained from IUPAC Compendium of Chemical Terminology—the Gold Book online on Jan. 17, 2018.*

* cited by examiner

*Primary Examiner* — Cynthia Hamilton
(74) *Attorney, Agent, or Firm* — Birch, Stewart, Kolasch & Birch, LLP

(57) ABSTRACT

A salt represented by formula (I):

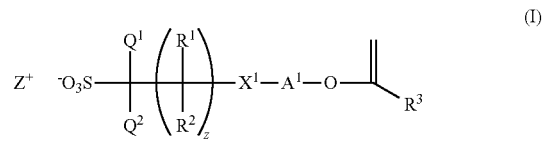

wherein $Q^1$ and $Q^2$ independently each represent a fluorine atom or a C1-C6 perfluoroalkyl group,
$R^1$ and $R^2$ independently each represent a hydrogen atom, a fluorine atom or a C1-C6 perfluoroalkyl group,
z represents an integer of 0 to 6,
$X^1$ represents *—C(=O)—O—, *—O—C(=O)—, *—O—C(=O)—O— or —O—, where * represents a binding site to —C($R^1$)($R^2$)— or —C($Q^1$)($Q^2$)-,
$A^1$ represents a C2-C36 divalent hydrocarbon group in which a methylene group can be replaced by an oxygen atom, a sulfur atom, a carbonyl group or a sulfonyl group and in which a hydrogen atom can be replaced by a substituent,
$R^3$ represents a hydrogen atom or a methyl group, and
$Z^+$ represents an organic cation.

7 Claims, No Drawings

SALT AND PHOTORESIST COMPOSITION CONTAINING THE SAME

This nonprovisional application claims priority under 35 U.S.C. § 119(a) on No. 2016-171968 filed in JAPAN on Sep. 2, 2016, the entire contents of which are hereby incorporated by reference.

FIELD OF THE INVENTION

The present invention relates to a salt and a photoresist composition containing the same.

BACKGROUND OF THE INVENTION

US2007/0149702A1 mentions an acid generator which contains a salt.

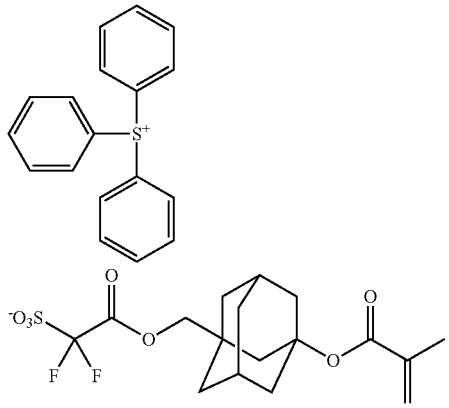

US2007/0100096A1 mentions a photoresist composition comprising the following salt as an acid generator.

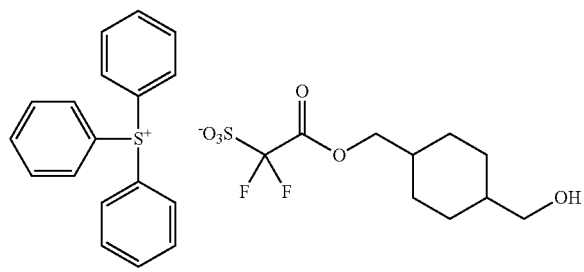

JP2013-82893A1 mentions a photoresist composition which comprises a salt as an acid generator.

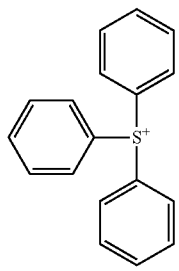

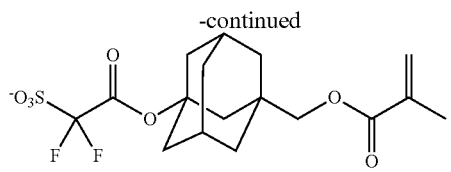

SUMMARY OF THE INVENTION

The present invention relates to the followings:

<1> A salt represented by formula (I):

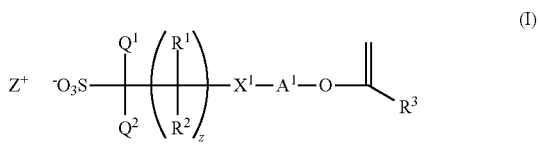

wherein $Q^1$ and $Q^2$ independently each represent a fluorine atom or a C1-C6 perfluoroalkyl group, $R^1$ and $R^2$ independently each represent a hydrogen atom, a fluorine atom or a C1-C6 perfluoroalkyl group, z represents an integer of 0 to 6, $X^1$ represents *—C(=O)—O—, *—O—C(=O)—, *—O—C(=O)—O— or —O—, where * represents a binding site to —C($R^1$)($R^2$)— or —C($Q^1$)($Q^2$)-, $A^1$ represents a C2-C36 divalent hydrocarbon group in which a methylene group can be replaced by an oxygen atom, a sulfur atom, a carbonyl group or a sulfonyl group and in which a hydrogen atom can be replaced by a substituent, $R^3$ represents a hydrogen atom or a methyl group, and $Z^+$ represents an organic cation.

<2> The salt according to <1> wherein $X^1$ represents *—C(=O)—O—.

<3> The salt according to <1> or <2> wherein the divalent hydrocarbon group represented by $A^1$ has a C3-C18 alicyclic hydrocarbon group.

<4> The salt according to any one of <1> to <3> wherein $R^3$ is a hydrogen atom.

<5> An acid generator comprising the salt according to any one of <1> to <4>.

<6> A photoresist composition comprising the salt according to any one of <1> to <5> as an acid generator and a resin which comprises a structural unit having an acid-labile group.

<7> The photoresist composition according to <6> which further comprises a salt generating an acid weaker in acidity than an acid generated from the acid generator.

<8> A process for producing a photoresist pattern comprising the following steps (1) to (5):

(1) a step of applying the photoresist composition according to <6> on a substrate, (2) a step of forming a composition film by conducting drying, (3) a step of exposing a composition film to radiation, (4) a step of baking the exposed composition film, and (5) a step of developing the baked composition film with an alkaline developer, thereby forming a photoresist pattern.

DESCRIPTION OF EMBODIMENTS

The salt of the disclosure is represented by the formula (I):

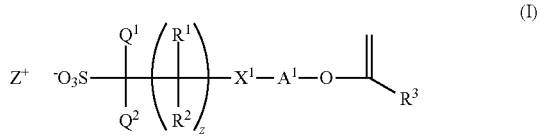

in which $Q^1$ and $Q^2$ independently each represent a fluorine atom or a C1-C6 perfluoroalkyl group, $R^1$ and $R^2$ independently each represent a hydrogen atom, a fluorine atom or a C1-C6 perfluoroalkyl group, z represents an integer of 0 to 6, $X^1$ represents *—C(=O)—O—, *—O—C(=O)—, *—O—C(=O)—O— or —O—, where * represents a binding site to —C($R^1$)($R^2$)— or —C($Q^1$)($Q^2$), $A^1$ represents a C2-C36 divalent hydrocarbon group in which a methylene group can be replaced by an oxygen atom, a sulfur atom, a carbonyl group or a sulfonyl group and in which a hydrogen atom can be replaced by a substituent, $R^3$ represents a hydrogen atom or a methyl group, and $Z^+$ represents an organic cation.

For $Q^1$, $Q^2$, $R^1$ and $R^2$, examples of the perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferred.

$Q^1$ and $Q^2$ each independently preferably represent a fluorine atom or a trifluoromethyl group, and Q and $Q^2$ are more preferably fluorine atoms.

$R^1$ and $R^2$ each independently preferably represent a hydrogen atom or a fluorine atom. z is preferably 0.

$X^1$ preferably represents *—C(=O)—O— where * represents a binding site to —C($R^1$)($R^2$)— or —C($Q^1$)($Q^2$)-.

As to $A^1$, examples of the C2-C36 divalent hydrocarbon group include a C2-C36 alkylene group, a C3-C36 divalent monocyclic or polycyclic alicyclic hydrocarbon group, a C6-C36 aromatic hydrocarbon group and any combination of them.

Examples of the saturated hydrocarbon group include linear alkylene groups such as an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,1-diyl group and a dodecane-1,12-diyl group;

branched alkylene groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, 2-methylpropane-1,2-diyl group, pentane-1,4-diyl group, and 2-methylbutane-1,4-diyl group;

divalent monocyclic alicyclic hydrocarbon groups such as cyclobutane-1,3-diyl group, cyclopentane-1,3-diyl group, cyclohexane-1,4-diyl group and cyclooctane-1,5-diyl group;

divalent polycyclic alicyclic hydrocarbon groups such as norbornane-1,4-diyl group, norbornane-2,5-diyl group, adamantane-1,5-diyl group and adamantane-2,6-diyl group; and divalent aromatic hydrocarbon group such as a phenylene group, a naphthylene group, an anthrylene group, a p-methylphenylene group, a p-tert-butylphenylene group, a p-adamantylphenylene group, a tolylene group, a xylylene group, a cumylene group, a mesitylene group, a biphenylene group, a phenanthrylene group, a 2,6-diethylphenylene group and a 2-methyl-6-ethylphenylene group. The divalent hydrocarbon group represented by $A^1$ can have a substituent. Examples of the substituent include a hydroxyl group, a cyano group, a carboxyl group, a C1-C12 alkoxy group, a C2-C13 alkoxycarbonyl group, a C2-C13 alkoxycarbonyloxy group, or any combination of these groups.

Examples of the alkoxy group include a methoxy group, an ethoxy group, a propoxy group, a butoxy group, a pentyloxy group and a hexyloxy group.

Examples of the alkylcarbony group include an acetyl group, a propyonyl group and a butyryl group.

Examples of alkylcarbonyloxy group include a methylcarbonyloxy group, an ethylcarbonyloxy group, a propylcarbonyloxy group and a butylcarbonyloxy group.

In the divalent hydrocarbon group represented by $A^1$, a methylene group can be replaced by an oxygen atom, a sulfur atom, a carbonyl group or a sulfonyl group.

The divalent hydrocarbon group represented by $A^1$ has preferably a C3-C18 alicyclic hydrocarbon group, more preferably a cyclohexanediyl group or an adamantanediyl group. $A^1$ is preferably a divalent hydrocarbon group composed of a C1-C6 alkyl group and a cyclohexanediyl or adamantanediyl group.

$R^3$ is preferably a hydrogen atom.

Specific examples of the anion for the salt represented by formula (I) include the following ones. Among them, an anion represented by any one of formulae (Ia-1) to (Ia-11), (Ia-13) to (Ia-20) and (Ia-22) is preferred, and an anion represented by any one of formulae (Ia-1) to (Ia-3) and (Ia-13) to (Ia-16) is more preferred.

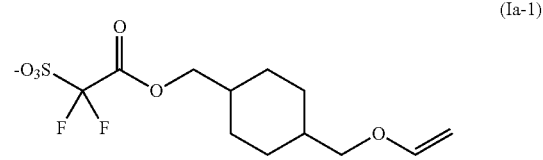
(Ia-1)

(1a-2)

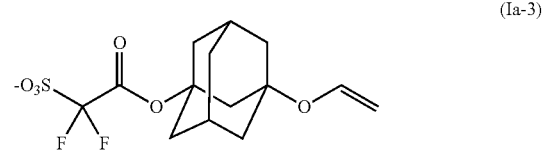
(Ia-3)

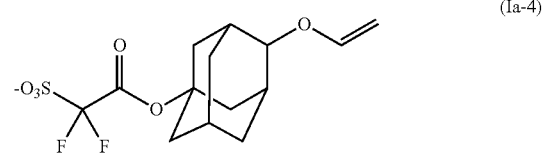
(Ia-4)

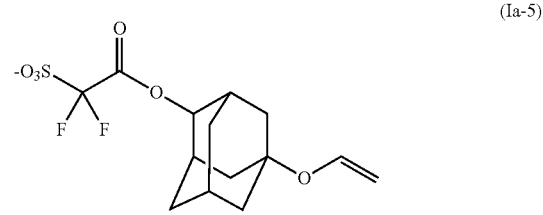
(Ia-5)

-continued

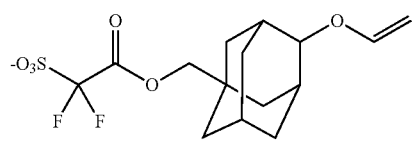
(Ia-6)

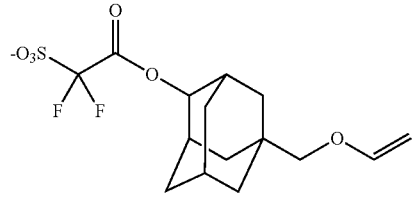
(Ia-7)

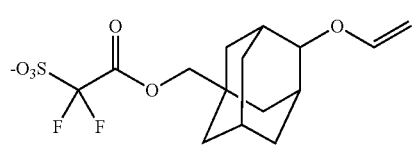
(Ia-8)

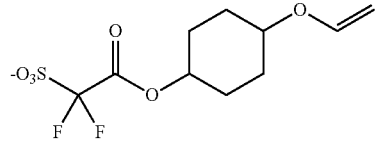
(Ia-9)

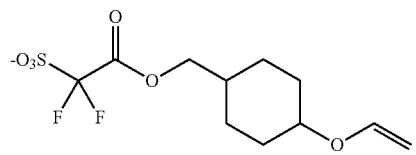
(Ia-10)

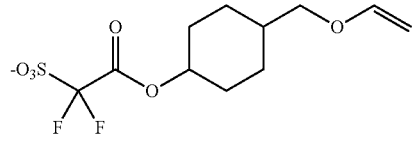
(Ia-11)

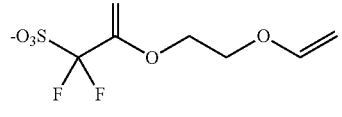
(Ia-12)

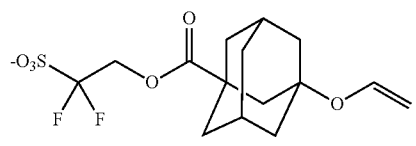
(Ia-13)

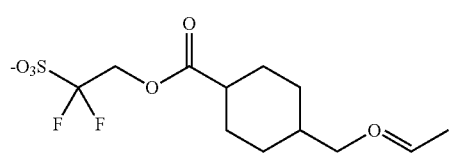
(Ia-14)

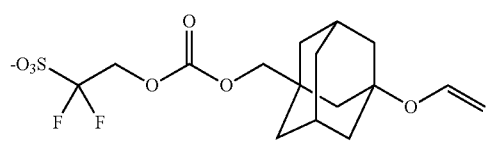
(Ia-15)

-continued

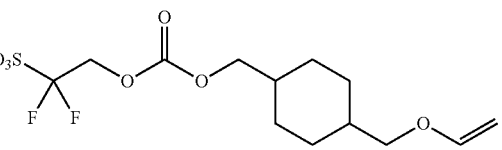
(Ia-16)

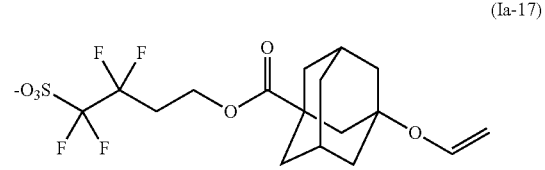
(Ia-17)

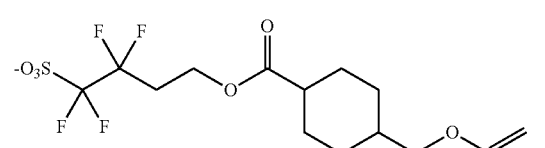
(Ia-18)

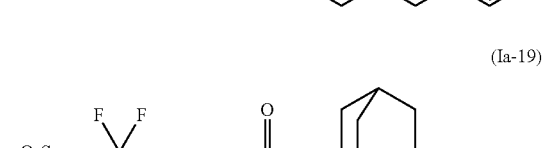
(Ia-19)

(Ia-20)

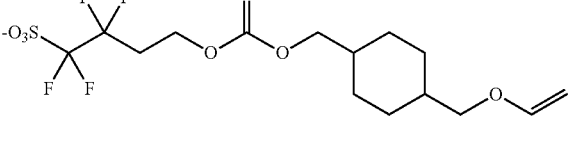
(Ia-21)

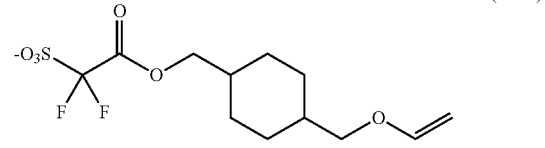
(Ia-22)

Examples of the organic cation represented by $Z^+$ include an organic onium cation such as an organic sulfonium cation, an organic iodonium cation, an organic ammonium cation, a benzothiazolium cation and an organic phosphonium cation. As $Z^+$, an organic sulfonium cation and an organic iodonium cation are preferred, and an arylsulfonium cation is more preferred. Herein, the arylsulfonium includes those having one, two or three aryl groups.

Preferable examples of the organic cation represented by $Z^+$ include the organic cations represented by the formulae (b2-1) to (b2-4):

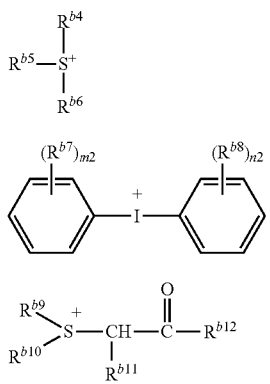

(b2-1)

(b2-2)

(b2-3)

(b2-4)

wherein $R^{b4}$, $R^{b5}$ and $R^{b6}$ independently represent a C1-C30 aliphatic hydrocarbon group in which a hydrogen atom can be replaced by a hydroxy group, a C1-C12 alkoxy group or a C6-C18 alicyclic hydrocarbon group, a C3-C36 alicyclic hydrocarbon group in which a hydrogen atom can be replaced by a halogen atom, a C2-C4 acyl group or a glycidyloxy group, and a C6-C36 aromatic hydrocarbon group in which a hydrogen atom can be replaced by a halogen atom, a hydroxy group, or C1-C12 alkoxy group; and $R^{b4}$ and $R^{b5}$, $R^{b4}$ and $R^{b6}$, or $R^{b5}$ and $R^{b6}$ can be bonded each other to form a ring containing $S^+$;

$R^{b7}$ and $R^{b8}$ are independently in each occurrence a hydroxy group, a C1-C12 alkyl group or a C1-C12 alkoxy group;

m2 and n2 independently represents an integer of 0 to 5;

$R^{b9}$ and $R^{b10}$ independently represent a C1-C36 aliphatic hydrocarbon group or a C3-C36 alicyclic hydrocarbon group, or $R^{b9}$ and $R^{b10}$ are bonded each other to form a ring together with the adjacent —$S^+$—, and one or more —$CH_2$— in the ring may be replaced by an oxygen atom, a sulfur atom or carbonyl group; and $R^{b11}$ represents a hydrogen atom, a C1-C36 aliphatic hydrocarbon group, a C3-C36 alicyclic hydrocarbon group, or a C6-C18 aromatic hydrocarbon group, and $R^{b12}$ represents a C1-C12 aliphatic hydrocarbon group where a hydrogen atom can be replaced by a C6-C18 aromatic hydrocarbon group, a C3-C18 alicyclic hydrocarbon group, and a C6-C18 aromatic hydrocarbon group optionally substituted with a C1-C12 alkoxy group or a C1-C12 alkylcarbonyloxy group;

or $R^{b11}$ and $R^{b12}$ are bonded each other to form a C1-C10 divalent alicyclic hydrocarbon group which forms a 2-oxocycloalkyl group together with the adjacent —CHCO—, and one or more —$CH_2$— in the group may be replaced by an oxygen atom, a sulfur atom or carbonyl group; and $R^{b13}$, $R^{b14}$, $R^{b15}$, $R^{b16}$, $R^{b17}$ and $R^{b18}$ independently represent a hydroxy group, a C1-C12 alkyl group or a C1-C12 alkoxy group;

$L^{b31}$ represents —S— or —O—; and o2, p2, s2 and t2 each independently represents an integer of 0 to 5;

q2 and r2 each independently represents an integer of 0 to 4; and u2 represents 0 or 1.

Examples of the aliphatic hydrocarbon group represented by each substituent include an alkyl group such as a methyl group, an ethyl group, a propyl group, an isopropyl group, a butyl group, a sec-butyl group, a tert-butyl group, a pentyl group, a hexyl group, an octyl group, and a 2-ethylhexyl group. The aliphatic hydrocarbon group represented by $R^{b9}$ to $R^{b12}$ is preferably a C1-C18 alkyl group, more preferably a C1-C12 alkyl group.

Examples of the alkyl group where a hydrogen atom has been replaced by an alicyclic hydrocarbon group include 1-(adamantane-1-yl) alkane-1-yl group.

The alicyclic hydrocarbon group represented by each substituent may be monocyclic or polycyclic, a hydrogen atom of which can be replaced by an alkyl group. When a hydrogen atom of it has been replaced by an alkyl group, the total number of carbon atoms is 30 or less.

Examples of the monocyclic alicyclic hydrocarbon group include a cycloalkyl group such as a cyclopropyl group, a cyclobutyl group, a cyclopentyl group, a cyclohexyl group, a cycloheptyl group, a cyclodecyl group.

Examples of the polycyclic alicyclic hydrocarbon group include a decahydronaphtyl group, an adamantyl group, a norbornyl group, and the following ones.

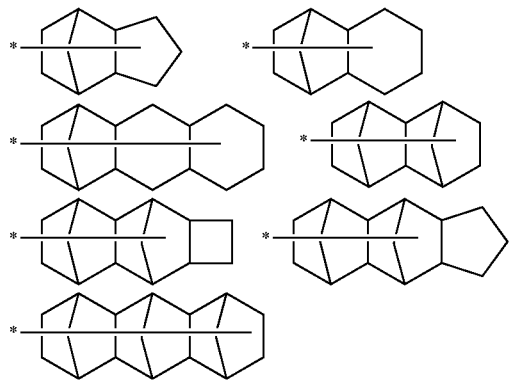

The alicyclic hydrocarbon group represented by $R^{b9}$ to $R^{b12}$ has preferably 3 to 18, more preferably 4 to 12, carbon atoms.

Examples of the alicyclic hydrocarbon group where a hydrogen atom has been replaced by an alkyl group include a methylcyclohexyl group, a 2-alkyladamantane-2-yl group, a methylnorbornyl group, and an isobornyl group.

Preferable examples of the aromatic hydrocarbon group include substituted or unsubstituted phenyl group such as a phenyl group, a tolyl group, a xylyl group, a cumenyl group, a mesityl group, a 4-ethylphenyl group, 4-tert-butylphenyl group, 4-cyclohexylphenyl group, a 4-adamantylphenyl group, a 2,6-diethylphenyl group, a 2-methyl-6-ethylphenyl group; a biphenyl group, a naphtyl group, a phenanthryl group.

Preferable examples of the aromatic hydrocarbon group where a hydrogen atom has been replaced by an alkoxy group include 4-methoxyphenyl group.

Preferable examples of the alkyl group where a hydrogen atom has been replaced by an aromatic hydrocarbon group, i.e., an aralkyl group, include a benzyl group, a phenethyl group, a phenylpropyl group, a trityl group, a naphthylmethyl group and a naphthylethyl group.

When the aromatic hydrocarbon group has an alkyl group or an alicyclic hydrocarbon group as a substituent, the substituent is preferably a C1-C12 alkyl group or a C3-C18 alicyclic hydrocarbon group. Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the C2-C4 acyl group include an acetyl group, a propionyl group and a butyryl group.

Examples of the halogen atom include a fluorine atom, a chlorine atom, a bromine atom and an iodine atom.

Preferable examples of the alkylcarbonyloxy group include a methylcarbonyloxy group, an ethylcarbonyloxy group, n-propylcarbonyloxy group, an isopropylcarbonyloxy group, n-butylcarbonyloxy group, sec-butylcarbonyloxy group, a tert-butylcarbonyloxy group, a pentylcarbonyloxy group, a hexylcarbonyloxy group, an octylcarbonyloxy group and 2-ethyl hexylcarbonyloxy group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain a sulfur atom or oxygen atom in addition to $S^+$. The ring preferably has 3 to 18 carbon atoms, and more preferably has 4 to 13 carbon atoms. Examples of such ring include, 3 to 12-membered rings, preferably 3 to 7-membered rings, specifically the following ones.

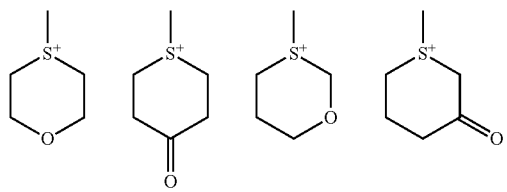

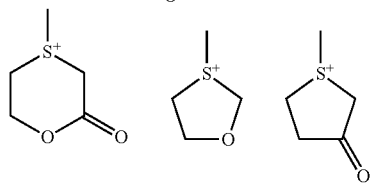

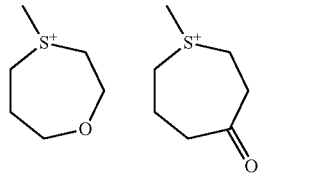

Examples of the ring group formed by bonding $R^{b9}$ and $R^{b10}$ together with the adjacent $S^+$ and the divalent alicyclic hydrocarbon group include, 3 to 12-membered rings, preferably 3 to 7-membered rings, specifically a thiolan-1-ium ring (tetrahydrothiophenium ring), a thian-1-ium ring and a 1,4-oxathian-4-ium ring.

Examples of the ring group formed by bonding $R^{b11}$ and $R^{b12}$ include 3 to 12-membered rings, preferably 3 to 7-membered rings, specifically oxocyclopentane ring, oxocyclohexane ring, oxonorbornane ring and oxoadamantane ring.

Among the above-mentioned cations, preferred is the cation represented by the formula (b2-1).

Examples of the cation represented by the formula (b2-1) include the following ones.

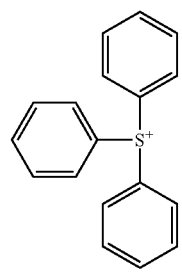

(b2-c-1)

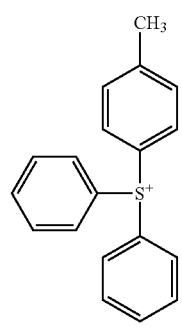

(b2-c-2)

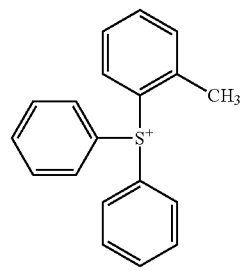

(b2-c-3)

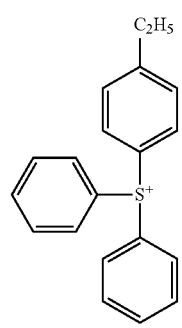

(b2-c-4)

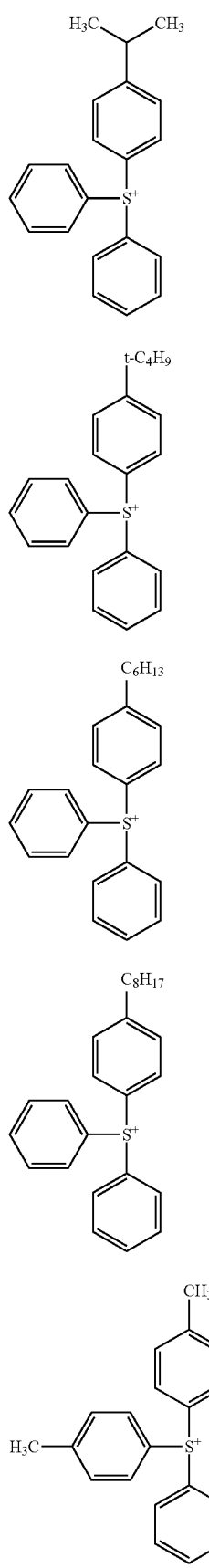
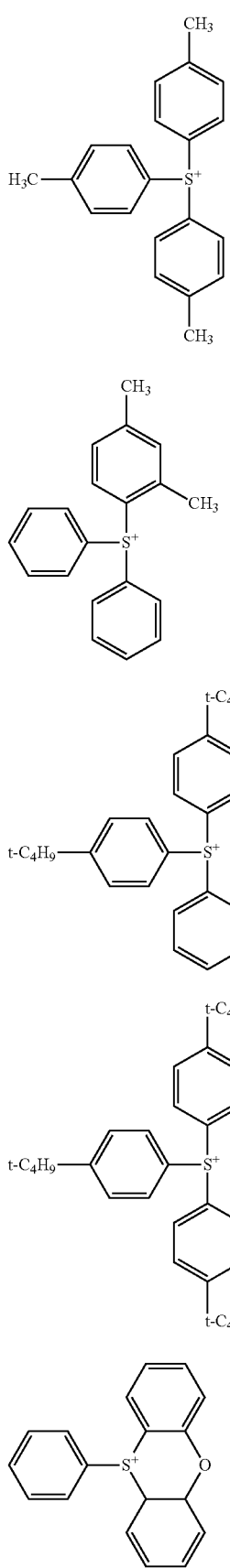

(b2-c-15)
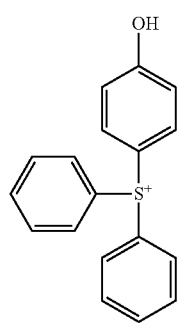
(b2-c-16)
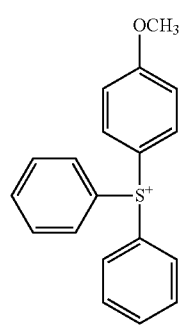
(b2-c-17)
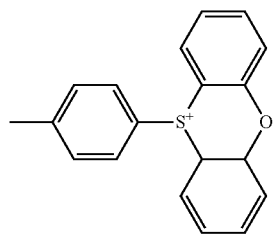
(b2-c-18)
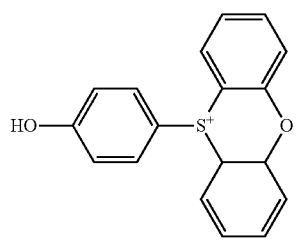
(b2-c-19)
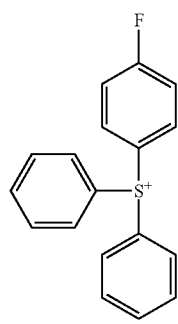
(b2-c-20)
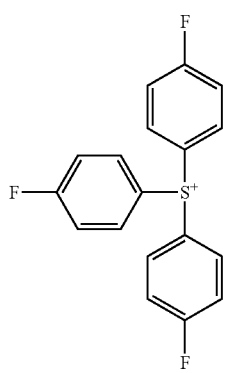
(b2-c-21)
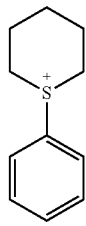
(b2-c-22)
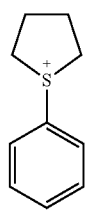
(b2-c-23)
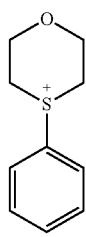
(b2-c-24)
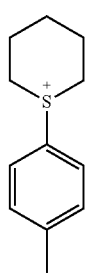
(b2-c-25)

-continued
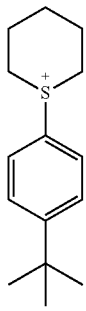
(b2-c-26)
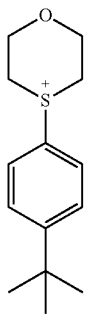
(b2-c-27)
Examples of the cation represented by the formula (b2-2) include the following ones.
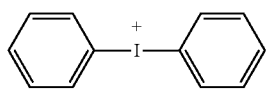
(b2-c-28)
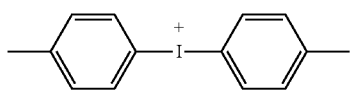
(b2-c-29)
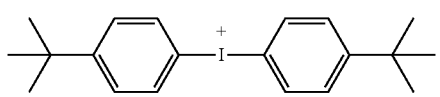
(b2-c-30)
Examples of the cation represented by the formula (b2-3) include the following ones.
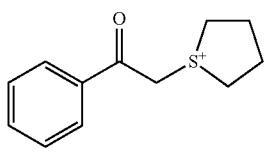
(b2-c-31)
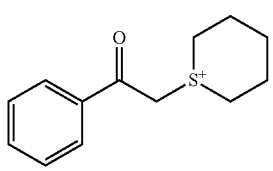
(b2-c-32)
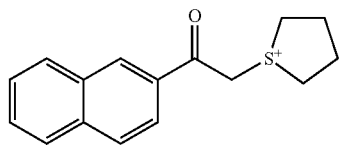
(b2-c-33)
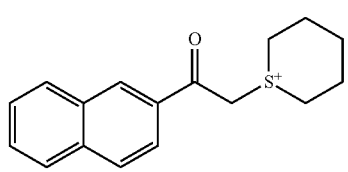
(b2-c-34)
Examples of the cation represented by the formula (b2-4) include the following ones.
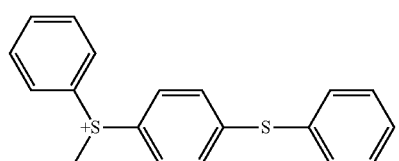
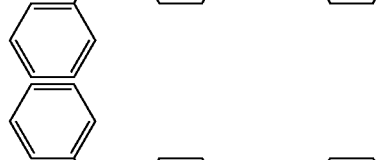
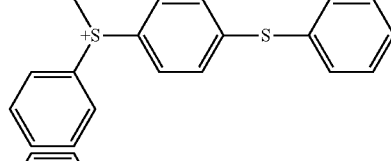
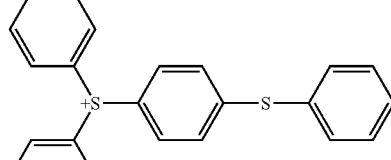
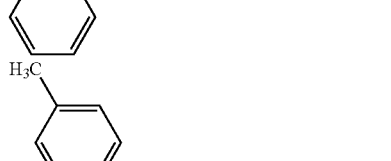
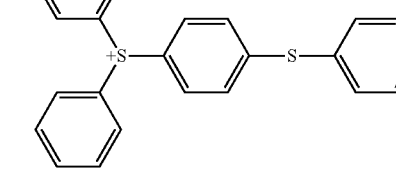
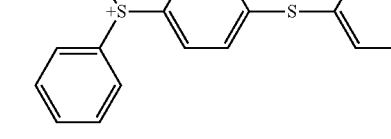

-continued

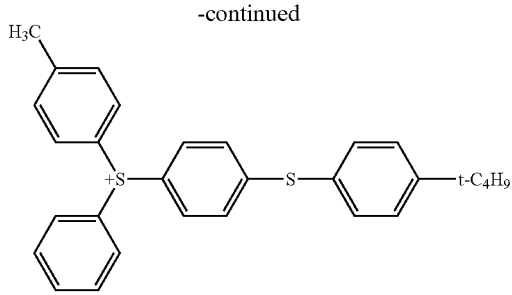

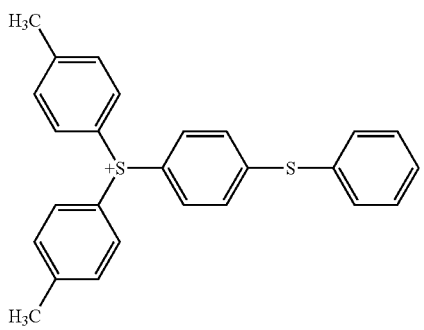

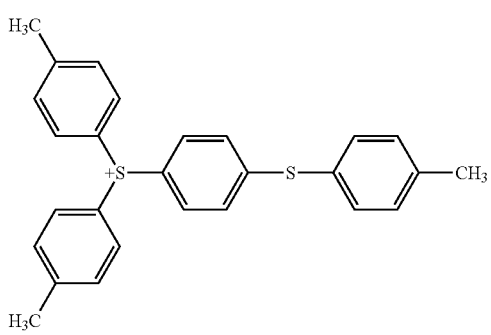

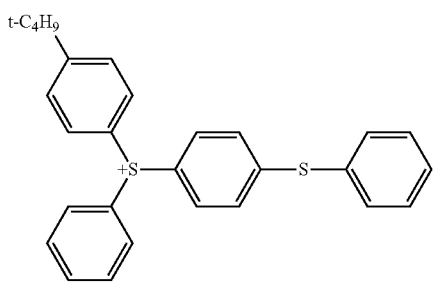

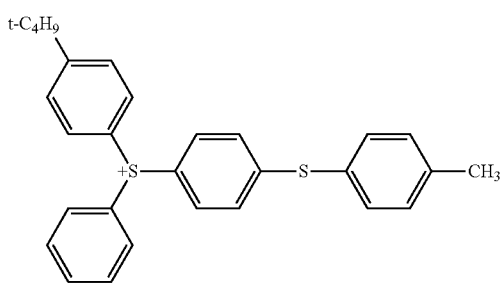

-continued

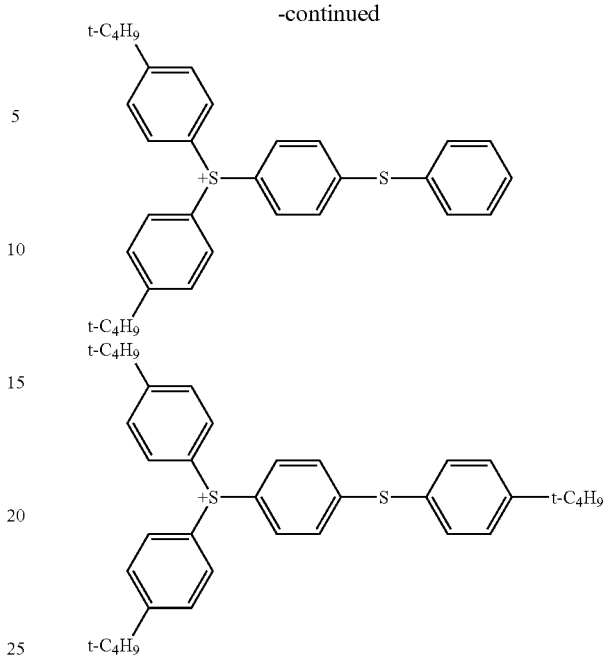

Among them, a cation represented by any one of formulae (b2-c-1), (b2-c-10), (b2-c-12), (b2-c-14), (b2-c-27), (b2-c-30) and (b2-c-31) is preferred.

Specific examples of the salt represented by formula (I) are listed in the following tables.

In those tables, every character in each column represents a sign which represents one of the chemical formulae specifically illustrated above. For example, the salt (I-1) consists of the anion of formula (Ia-1) and the cation of formula (b2-c-1) as shown below.

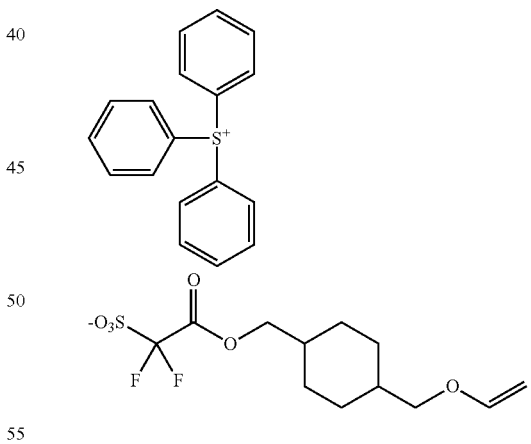

TABLE 1

| Salt  | anion  | cation   |
|-------|--------|----------|
| (I-1) | (Ia-1) | (b2-c-1) |
| (I-2) | (Ia-2) | (b2-c-1) |
| (I-3) | (Ia-3) | (b2-c-1) |
| (I-4) | (Ia-4) | (b2-c-1) |
| (I-5) | (Ia-5) | (b2-c-1) |
| (I-6) | (Ia-6) | (b2-c-1) |
| (I-7) | (Ia-7) | (b2-c-1) |
| (I-8) | (Ia-8) | (b2-c-1) |

TABLE 1-continued

| Salt | anion | cation |
| --- | --- | --- |
| (I-9) | (Ia-9) | (b2-c-1) |
| (I-10) | (Ia-10) | (b2-c-1) |
| (I-11) | (Ia-11) | (b2-c-1) |
| (I-12) | (Ia-12) | (b2-c-1) |
| (I-13) | (Ia-13) | (b2-c-1) |
| (I-14) | (Ia-14) | (b2-c-1) |
| (I-15) | (Ia-15) | (b2-c-1) |
| (I-16) | (Ia-16) | (b2-c-1) |
| (I-17) | (Ia-17) | (b2-c-1) |
| (I-18) | (Ia-18) | (b2-c-1) |
| (I-19) | (Ia-19) | (b2-c-1) |
| (I-20) | (Ia-20) | (b2-c-1) |
| (I-21) | (Ia-21) | (b2-c-1) |
| (I-22) | (Ia-22) | (b2-c-1) |
| (I-23) | (Ia-1) | (b2-c-10) |
| (I-24) | (Ia-2) | (b2-c-10) |
| (I-25) | (Ia-3) | (b2-c-10) |
| (I-26) | (Ia-4) | (b2-c-10) |
| (I-27) | (Ia-5) | (b2-c-10) |
| (I-28) | (Ia-6) | (b2-c-10) |
| (I-29) | (Ia-7) | (b2-c-10) |
| (I-30) | (Ia-8) | (b2-c-10) |
| (I-31) | (Ia-9) | (b2-c-10) |
| (I-32) | (Ia-10) | (b2-c-10) |
| (I-33) | (Ia-11) | (b2-c-10) |
| (I-34) | (Ia-12) | (b2-c-10) |
| (I-35) | (Ia-13) | (b2-c-10) |
| (I-36) | (Ia-14) | (b2-c-10) |
| (I-37) | (Ia-15) | (b2-c-10) |
| (I-38) | (Ia-16) | (b2-c-10) |
| (I-39) | (Ia-17) | (b2-c-10) |
| (I-40) | (Ia-18) | (b2-c-10) |

TABLE 2

| Salt | anion | cation |
| --- | --- | --- |
| (I-41) | (Ia-19) | (b2-c-10) |
| (I-42) | (Ia-20) | (b2-c-10) |
| (I-43) | (Ia-21) | (b2-c-10) |
| (I-44) | (Ia-22) | (b2-c-10) |
| (I-45) | (Ia-1) | (b2-c-12) |
| (I-46) | (Ia-2) | (b2-c-12) |
| (I-47) | (Ia-3) | (b2-c-12) |
| (I-48) | (Ia-4) | (b2-c-12) |
| (I-49) | (Ia-5) | (b2-c-12) |
| (I-50) | (Ia-6) | (b2-c-12) |
| (I-51) | (Ia-7) | (b2-c-12) |
| (I-52) | (Ia-8) | (b2-c-12) |
| (I-53) | (Ia-9) | (b2-c-12) |
| (I-54) | (Ia-10) | (b2-c-12) |
| (I-55) | (Ia-11) | (b2-c-12) |
| (I-56) | (Ia-12) | (b2-c-12) |
| (I-57) | (Ia-13) | (b2-c-12) |
| (I-58) | (Ia-14) | (b2-c-12) |
| (I-59) | (Ia-15) | (b2-c-12) |
| (I-60) | (Ia-16) | (b2-c-12) |
| (I-61) | (Ia-17) | (b2-c-12) |
| (I-62) | (Ia-18) | (b2-c-12) |
| (I-63) | (Ia-19) | (b2-c-12) |
| (I-64) | (Ia-20) | (b2-c-12) |
| (I-65) | (Ia-21) | (b2-c-12) |
| (I-66) | (Ia-22) | (b2-c-12) |
| (I-67) | (Ia-1) | (b2-c-14) |
| (I-68) | (Ia-2) | (b2-c-14) |
| (I-69) | (Ia-3) | (b2-c-14) |
| (I-70) | (Ia-4) | (b2-c-14) |
| (I-71) | (Ia-5) | (b2-c-14) |
| (I-72) | (Ia-6) | (b2-c-14) |
| (I-73) | (Ia-7) | (b2-c-14) |
| (I-74) | (Ia-8) | (b2-c-14) |
| (I-75) | (Ia-9) | (b2-c-14) |
| (I-76) | (Ia-10) | (b2-c-14) |
| (I-77) | (Ia-11) | (b2-c-14) |
| (I-78) | (Ia-12) | (b2-c-14) |

TABLE 2-continued

| Salt | anion | cation |
| --- | --- | --- |
| (I-79) | (Ia-13) | (b2-c-14) |
| (I-80) | (Ia-14) | (b2-c-14) |

TABLE 3

| Salt | anion | Cation |
| --- | --- | --- |
| (I-81) | (Ia-15) | (b2-c-14) |
| (I-82) | (Ia-16) | (b2-c-14) |
| (I-83) | (Ia-17) | (b2-c-14) |
| (I-84) | (Ia-18) | (b2-c-14) |
| (I-85) | (Ia-19) | (b2-c-14) |
| (I-86) | (Ia-20) | (b2-c-14) |
| (I-87) | (Ia-21) | (b2-c-14) |
| (I-88) | (Ia-22) | (b2-c-14) |
| (I-89) | (Ia-1) | (b2-c-27) |
| (I-90) | (Ia-2) | (b2-c-27) |
| (I-91) | (Ia-3) | (b2-c-27) |
| (I-92) | (Ia-4) | (b2-c-27) |
| (I-93) | (Ia-5) | (b2-c-27) |
| (I-94) | (Ia-6) | (b2-c-27) |
| (I-95) | (Ia-7) | (b2-c-27) |
| (I-96) | (Ia-8) | (b2-c-27) |
| (I-97) | (Ia-9) | (b2-c-27) |
| (I-98) | (Ia-10) | (b2-c-27) |
| (I-99) | (Ia-11) | (b2-c-27) |
| (I-100) | (Ia-12) | (b2-c-27) |
| (I-101) | (Ia-13) | (b2-c-27) |
| (I-102) | (Ia-14) | (b2-c-27) |
| (I-103) | (Ia-15) | (b2-c-27) |
| (I-104) | (Ia-16) | (b2-c-27) |
| (I-105) | (Ia-17) | (b2-c-27) |
| (I-106) | (Ia-18) | (b2-c-27) |
| (I-107) | (Ia-19) | (b2-c-27) |
| (I-108) | (Ia-20) | (b2-c-27) |
| (I-109) | (Ia-21) | (b2-c-27) |
| (I-110) | (Ia-22) | (b2-c-27) |
| (I-111) | (Ia-1) | (b2-c-30) |
| (I-112) | (Ia-2) | (b2-c-30) |
| (I-113) | (Ia-3) | (b2-c-30) |
| (I-114) | (Ia-4) | (b2-c-30) |
| (I-115) | (Ia-5) | (b2-c-30) |
| (I-116) | (Ia-6) | (b2-c-30) |
| (I-117) | (Ia-7) | (b2-c-30) |
| (I-118) | (Ia-8) | (b2-c-30) |
| (I-119) | (Ia-9) | (b2-c-30) |
| (I-120) | (Ia-10) | (b2-c-30) |

TABLE 4

| Salt | anion | Cation |
| --- | --- | --- |
| (I-121) | (Ia-11) | (b2-c-30) |
| (I-122) | (Ia-12) | (b2-c-30) |
| (I-123) | (Ia-13) | (b2-c-30) |
| (I-124) | (Ia-14) | (b2-c-30) |
| (I-125) | (Ia-15) | (b2-c-30) |
| (I-126) | (Ia-16) | (b2-c-30) |
| (I-127) | (Ia-17) | (b2-c-30) |
| (I-128) | (Ia-18) | (b2-c-30) |
| (I-129) | (Ia-19) | (b2-c-30) |
| (I-130) | (Ia-20) | (b2-c-30) |
| (I-131) | (Ia-21) | (b2-c-30) |
| (I-132) | (Ia-22) | (b2-c-30) |
| (I-133) | (Ia-1) | (b2-c-31) |
| (I-134) | (Ia-2) | (b2-c-31) |
| (I-135) | (Ia-3) | (b2-c-31) |
| (I-136) | (Ia-4) | (b2-c-31) |
| (I-137) | (Ia-5) | (b2-c-31) |
| (I-138) | (Ia-6) | (b2-c-31) |
| (I-139) | (Ia-7) | (b2-c-31) |
| (I-140) | (Ia-8) | (b2-c-31) |
| (I-141) | (Ia-9) | (b2-c-31) |

TABLE 4-continued

| Salt | anion | Cation |
|---|---|---|
| (I-142) | (Ia-10) | (b2-c-31) |
| (I-143) | (Ia-11) | (b2-c-31) |
| (I-144) | (Ia-12) | (b2-c-31) |
| (I-145) | (Ia-13) | (b2-c-31) |
| (I-146) | (Ia-14) | (b2-c-31) |
| (I-147) | (Ia-15) | (b2-c-31) |
| (I-148) | (Ia-16) | (b2-c-31) |
| (I-149) | (Ia-17) | (b2-c-31) |
| (I-150) | (Ia-18) | (b2-c-31) |
| (I-151) | (Ia-19) | (b2-c-31) |
| (I-152) | (Ia-20) | (b2-c-31) |
| (I-153) | (Ia-21) | (b2-c-31) |
| (I-154) | (Ia-22) | (b2-c-31) |

Among these specific examples, the salt represented by formula (I) is preferably salt(I-1), salt(I-2), salt(I-3), salt(I-15), salt(I-16), salt(I-23), salt(I-24), salt(I-37), salt(I-38), salt(I-45), salt(I-46), salt(I-59), salt(I-60), salt(I-67), salt(I-68), salt(I-81), salt(I-82), salt(I-89), salt(I-90), salt(I-103), salt(I-104), salt(I-111), salt(I-112), salt(I-125), salt(I-126), salt(I-133), salt(I-134), salt(I-147), salt(I-148).

The process for producing the salt represented by formula (I) will be illustrated.

When the salt represented by formula (I) has *—C(=O)—O— as $X^1$, it can be produced by reacting a salt represented by the formula (I1-a) with the compound represented by formula (I1-b) in a solvent such as chloroform or acetonitrile:

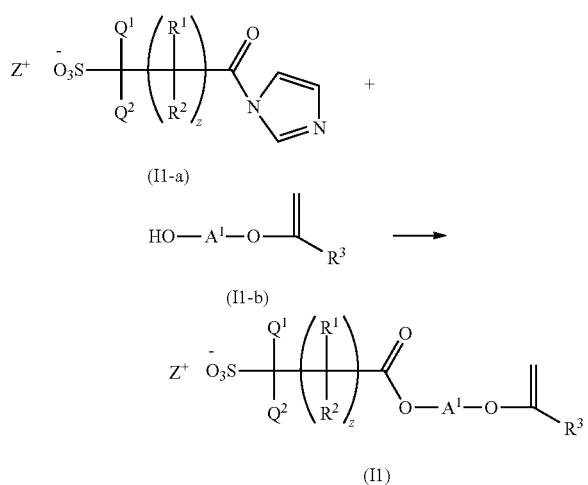

wherein $Q^1$, $Q^2$, $R^1$, $R^2$, $R^3$, z, $A^1$ and $Z^+$ are the same as defined above, and the formula (I1) represents the salt represented by formula (I) in which $X^1$ is *—C(=O)—O—.

The above-mentioned reaction is usually conducted at about 5 to 80° C., for 0.5 to 24 hours.

Specific examples of the salt represented by the formula (I1-a) include the following ones, which are available in the market.

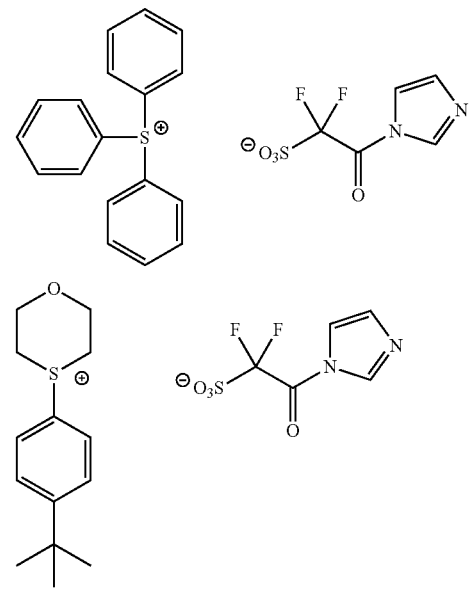

Specific examples of the compound represented by the formula (I1-b) include the following ones. These compounds are available in the market.

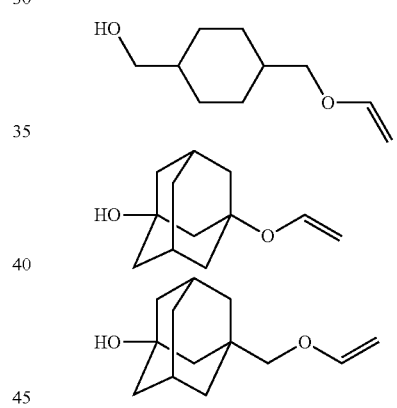

When the salt represented by formula (I) has *—O—C(=O)—O— as $X^1$, it can be produced by reacting a salt represented by the formula (I2-a) with the compound represented by formula (I1-b) in a solvent such as chloroform or acetonitrile:

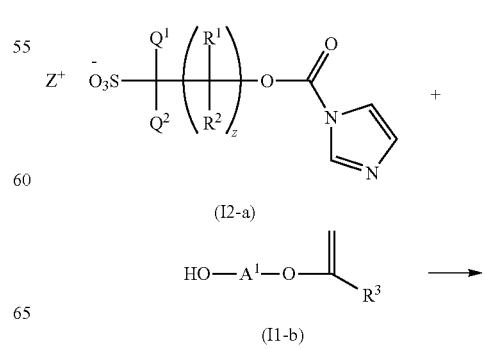

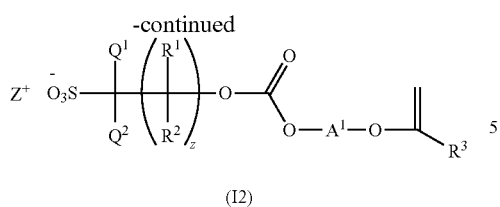

(I2)

wherein $Q^1$, $Q^2$, $R^1$, $R^2$, $R^3$, z, $A^1$ and $Z^+$ are the same as defined above, and formula (I2) represents the salt represented by formula (I) in which $X^1$ is *—O—C(=O)—O—

The above-mentioned reaction is usually conducted at about 5 to 80° C., for 0.5 to 24 hours.

The salt represented by formula (I2-a) can be produced by reacting a salt represented by the formula (I2-c) with the compound represented by formula (I2-d) in a solvent such as chloroform or acetonitrile:

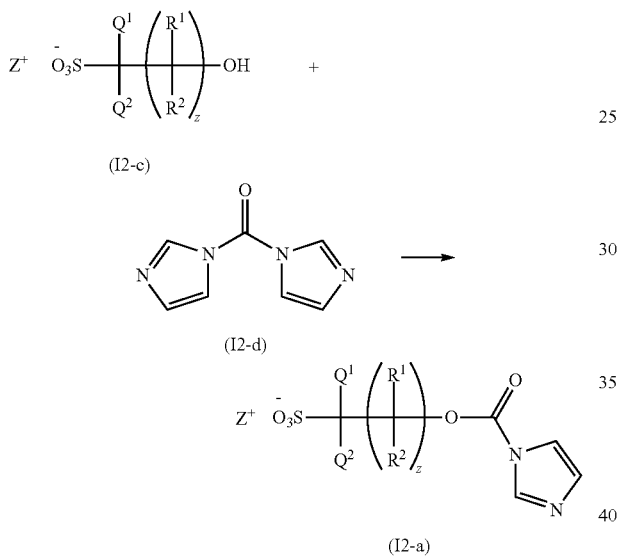

wherein $Q^1$, $Q^2$, $R^1$, $R^2$, z and $Z^+$ are the same as defined above.

The above-mentioned reaction is usually conducted at about 5 to 80° C., for 0.5 to 24 hours.

Specific examples of the salt represented by the formula (I1-c) include the following ones, which can be produced according to the method recited in JP2012-193170A1.

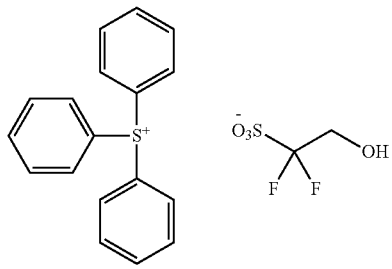

When the salt represented by formula (I) has *—O—C(=O)— as $X^1$, it can be produced by reacting a salt represented by the formula (I2-c) with the compound represented by formula (I3-b), in the presence of a base such as potassium carbonate, potassium iodide, pyridine, dimethylaminopyridine, in a solvent such as chloroform or acetonitrile:

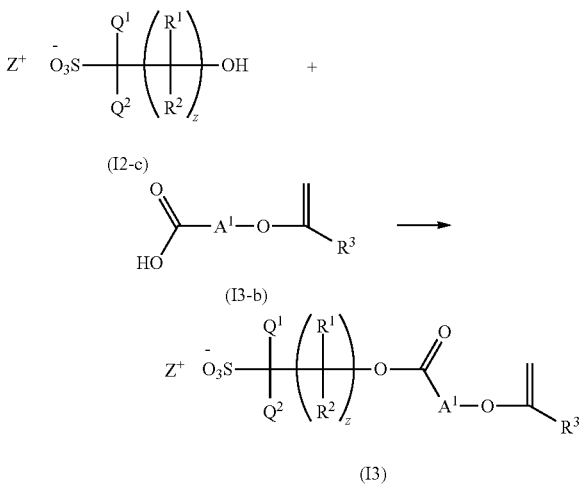

wherein $Q^1$, $Q^2$, $R^1$, $R^2$, $R^3$, z, $A^1$ and $Z^+$ are the same as defined above, and the salt represented by formula (I) in which $X^1$ is *—O—C(=O)— is represented by formula (I3).

The above-mentioned reaction is usually conducted at about 5 to 80° C., for 0.5 to 24 hours.

Specific examples of the salt represented by the formula (I3-b) include the following ones, which are available on the market.

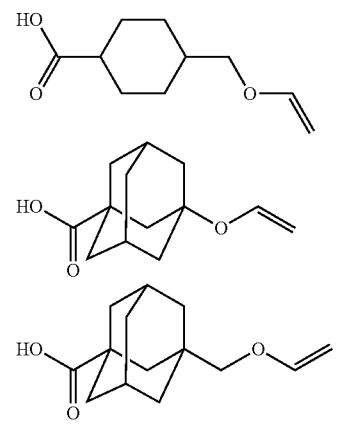

When the salt represented by formula (I) has —O— as $X^1$, it can be produced by reacting a salt represented by the formula (I2-c) with the compound represented by formula (I1-b), in the presence of a base such as potassium carbonate, in a solvent such as chloroform or acetonitrile:

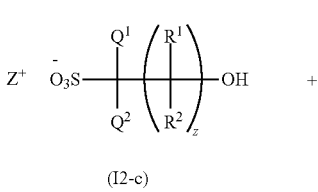

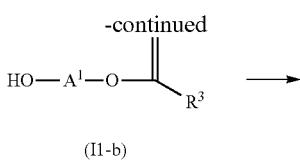

(I1-b)

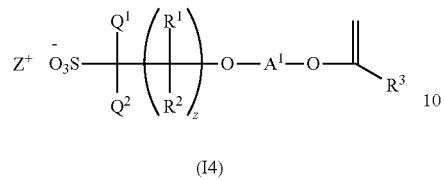

(I4)

<Acid Generator>

The acid generator of the disclosure comprises the salt represented by formula (I). The acid generator may contain two or more of the salt represented by formula (I). The acid generator may contain a known acid generator, which is described later, in addition to the salt represented by formula (I).

In the photoresist composition, an acid generates from the acid generator by light for lithography. The acid catalytically acts against an acid-labile group in the resin to cleave the acid-labile group.

When the acid generator contains a known acid generator, the weight ratio of the salt and the known acid generator is usually 1:99 to 99:1, preferably 2:98 to 98:2, more preferably 5:95 to 95:5, still more preferably 10:90 to 90:10.

<Photoresist Composition>

The photoresist composition of the disclosure comprises the salt represented by formula (I) as an acid generator and a resin having an acid-labile group which resin is referred to as "Resin (A)". The photoresist composition may further contain a known acid generator, a quencher, or solvent. Hereinafter, a known acid generator is referred to as "acid generator (B)".

The content of the salt represented by formula (I) is preferably 0.1 to 35% by mass, more preferably 0.5 to 30% by mass, still more preferably 1 to 25% by mass of solid components.

Resin (A) usually has a structural unit having an acid-labile group. Hereinafter, the structural unit is sometimes referred to as "structural unit (a1)".

Preferably Resin (A) further has another structural unit than the structural unit (a1), i.e. a structural unit having no acid-labile group, which is sometimes referred to as "structural unit (s)".

Herein, "an acid-labile group" means a group which has a hydrophilic group, such as a hydroxy group or a carboxy group, resulting from removing a leaving group therefrom by the action of an acid.

The structural unit (a1) is derived from a monomer having an acid-labile group which is sometimes referred to as "monomer (a1)". Specific examples of the acid-labile group include a group represented by the formula (1):

(1)

wherein $R^{a1}$, $R^{a2}$ and $R^{a3}$ each independently represent a C1-C8 alkyl group, a C3-C20 alicyclic hydrocarbon group or a combination of them, or $R^{a1}$ and $R^{a2}$ may be bonded each other to form a C3-C20 divalent alicyclic hydrocarbon group together with the carbon atom bonded to both of them, "na" represents an integer of 0 or 1, and * represents a binding site, and a group represented by the formula (2):

(2)

wherein $R^{a1'}$ and $R^{a2'}$ each independently represent a hydrogen atom or a C1-C12 hydrocarbon group, and $R^{a3'}$ represents a C1-C20 hydrocarbon group, or $R^{a3'}$ is bonded to $R^{a1'}$ or $R^{a2'}$ to form a C2-C20 divalent heterocyclic group with a carbon atom and X bonded thereto, a methylene group in the divalent heterocyclic group may be replaced by —O— or —S—, X represents an oxygen atom or a sulfur atom, and * represents a binding site.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, and the followings.

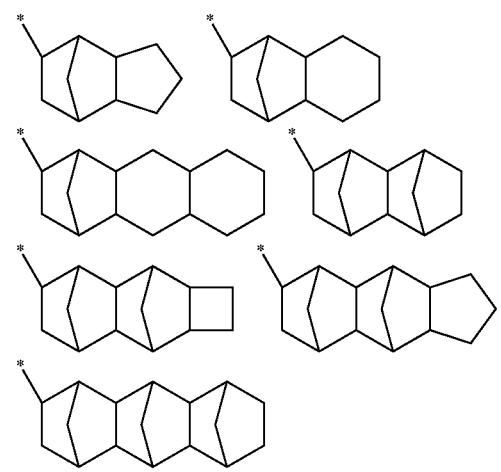

The alicyclic hydrocarbon group preferably has C3-C16 carbon atoms. The combination of alkyl group and alicyclic hydrocarbon group includes a methylcyclohexyl group, a dimethylcyclohexyl group, a methylnorbornyl group, a cyclohexylmethyl group, an adamantylmethyl group, a norbornylethyl group.

When $R^{a1}$ and $R^{a2}$ of formula (1) are bonded each other to form a C2-C20 divalent hydrocarbon group, examples of the moiety represented by —C($R^{a1}$)($R^{a2}$)($R^{a3}$) include the following groups and the ring preferably has 3 to 12 carbon atoms:

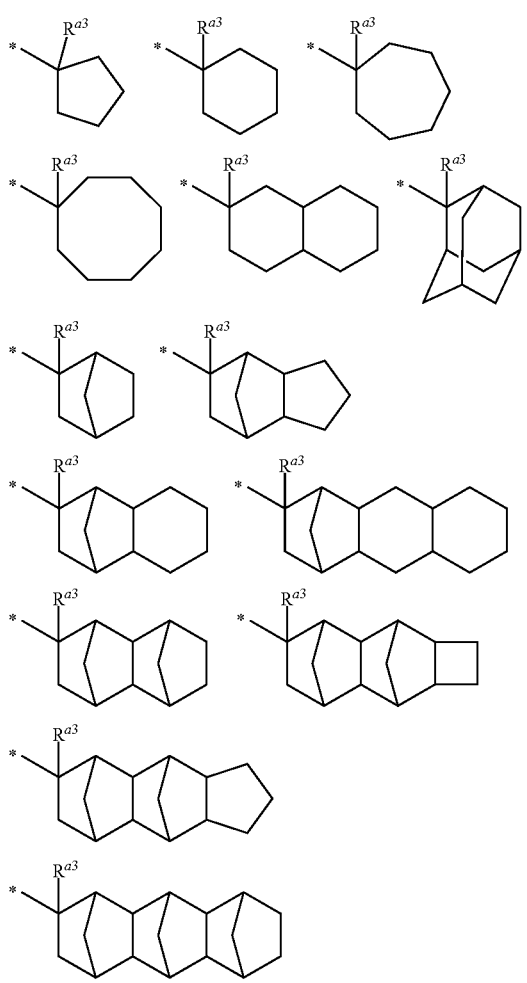
wherein $R^{a3}$ is as defined above and * represents a binding site. Specific examples of the groups represented by formula (1) include the following ones:
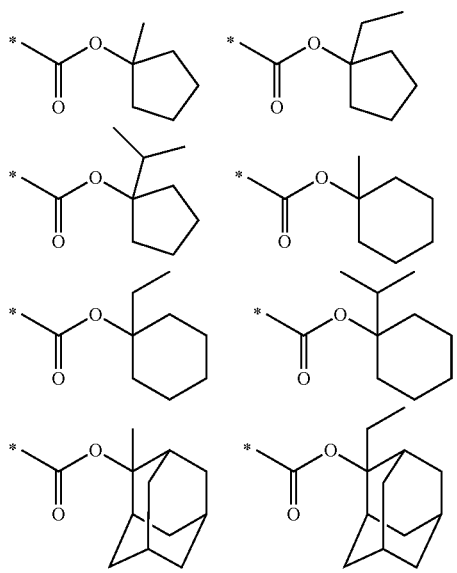
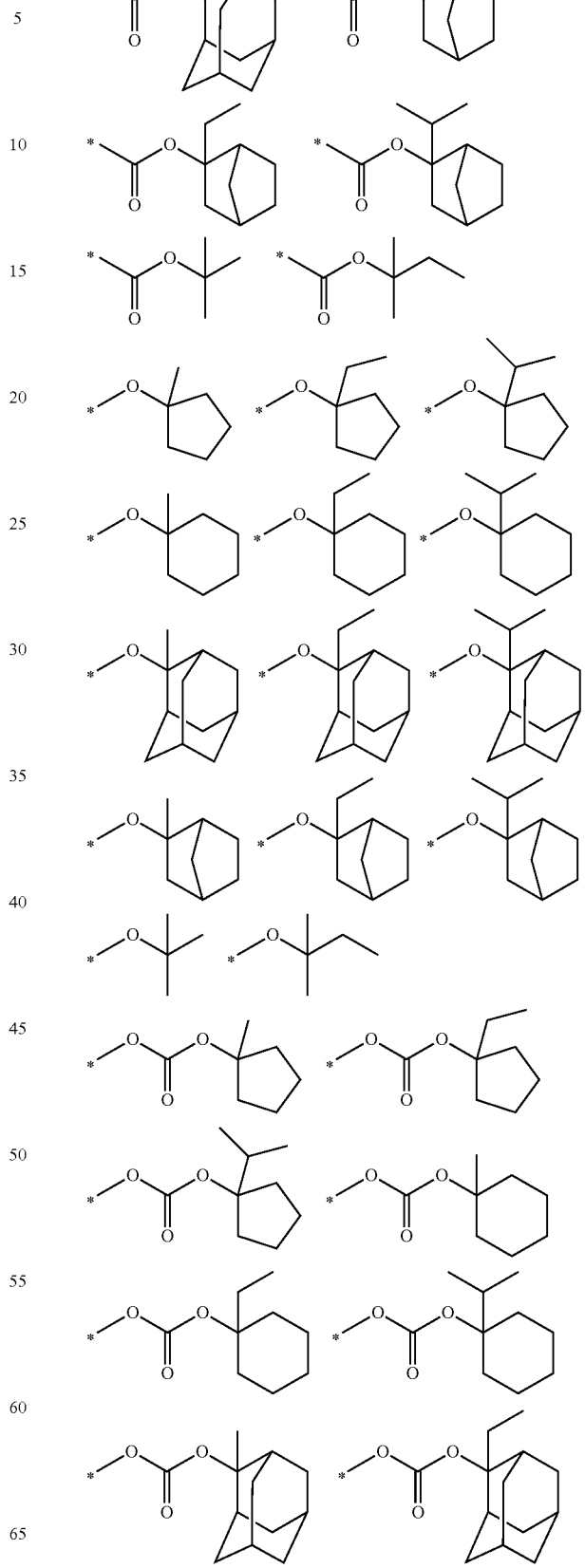

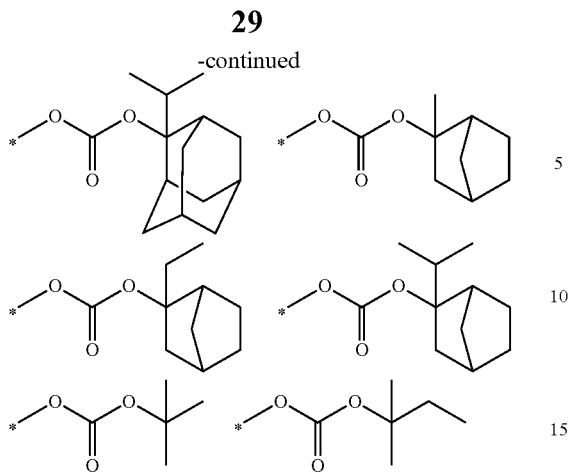

in which * represents a binding site.

As the group represented by the formula (1), preferred are 1,1'-dialkylalkoxylcarbonyl group, i.e., the group represented by the formula (1) wherein $R^{a1}$, $R^{a2}$ and $R^{a3}$ each independently represent a C1-C8 alkyl group, preferably a tert-butyl group;

2-alkyladaman-2-tyloxycarbonyl group, i.e., the group represented by the formula (1) wherein $R^{a1}$ and $R^{a2}$ are bonded each other to form an adamantyl group and $R^{a3}$ is a C1-C8 alkyl group; and a 1-(1-adaman-1-tyl)-1-alkylalkoxycarbonyl group, i.e., the group represented by the formula (1) wherein $R^{a1}$ and $R^{a2}$ are C1-C8 alkyl groups and $R^{a3}$ is an adamantyl group.

As to formula (2), examples of the hydrocarbon group include an alkyl group, an alicyclic hydrocarbon group, an aromatic hydrocarbon group, and any combination of these hydrocarbon groups. Examples of the alkyl group and the alicyclic hydrocarbon group include the same as described above.

Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the divalent heterocyclic group formed by bonding with $R^{a2'}$ or $R^{a3'}$ with a carbon atom and X bonded thereto include the following groups.

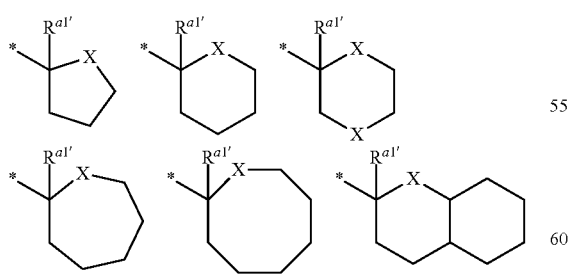

In each formula, $R^{a1'}$, X and * are as defined above.

Preferably, at least one of $R^{a1'}$ and $R^{a2'}$ is a hydrogen atom. Examples of the group represented by formula (2) include the following.

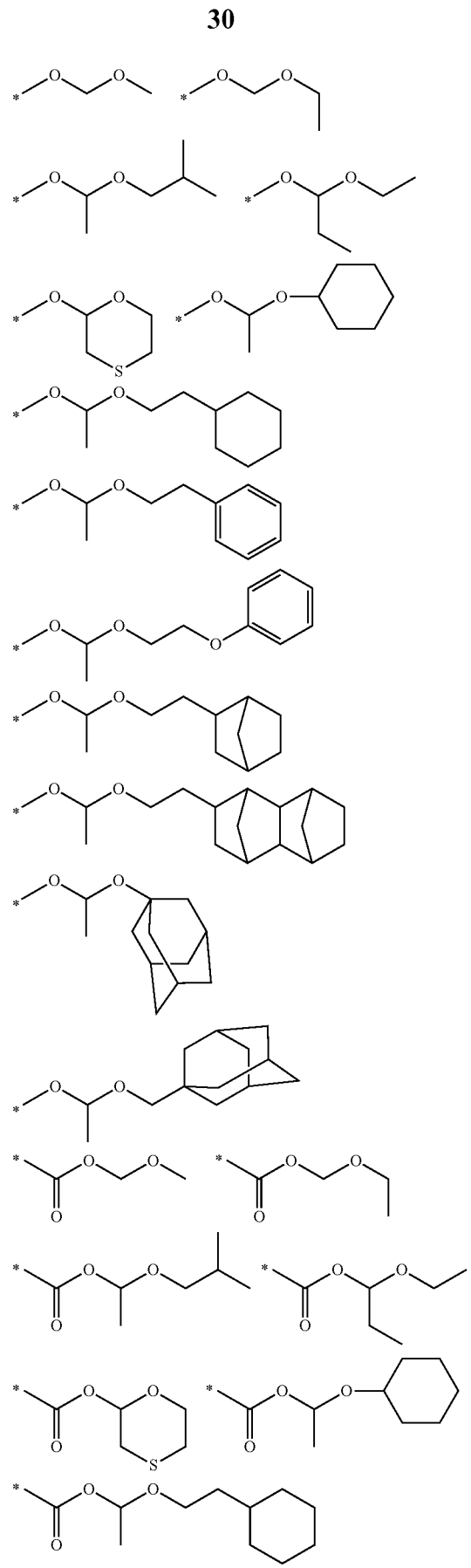

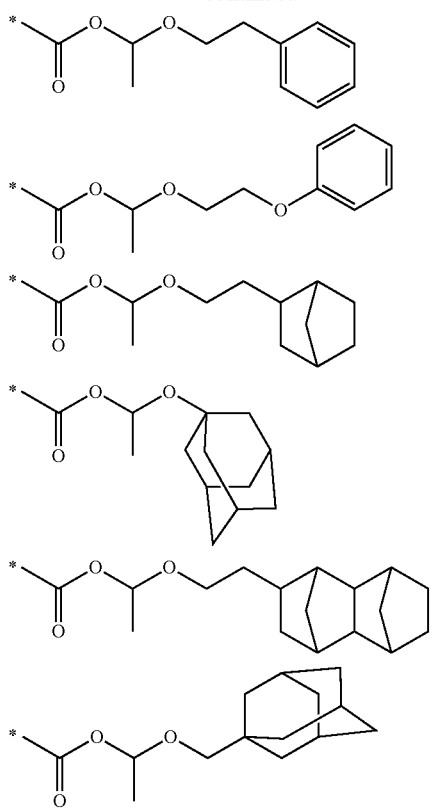

The monomer (a1) is preferably a compound having an acid-labile group and a carbon-carbon double bond, and is more preferably a (meth)acrylate compound having an acid-labile group.

Such (meth)acrylate compound preferably has a C5-C20 alicyclic hydrocarbon group. When the photoresist composition has a resin which has a structural unit with a bulky structure such as a saturated alicyclic hydrocarbon group, the photoresist composition can provide a photoresist pattern with excellent resolution.

Specific examples of the structural unit derived from the (meth)acrylate compound having a group of formula (1) include those represented by the formulae (a1-0), (a1-1) and (a1-2). The structural units represented by the formulae (a1-0), (a1-1) and (a1-2) are sometimes referred to as "structural unit (a1-0)", "structural unit (a1-1)" and "structural unit (a1-2)", respectively. The monomers from which the structural unit (a1-0), (a1-1) and (a1-2) are derived are sometimes referred to as "monomer (a1-0)", "monomer (a1-1)" and "monomer (a1-2)", respectively.

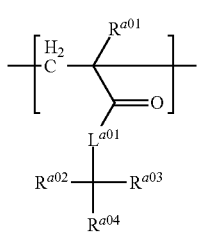
(a1-0)

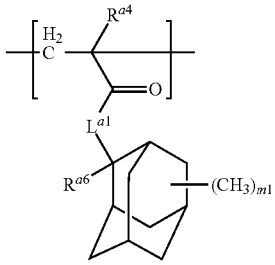
(a1-1)

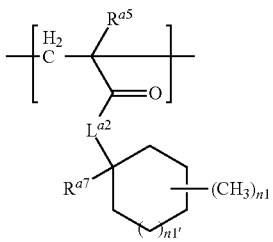
(a1-2)

In formulae (a1-0), (a1-1) and (a1-2), $L^{a01}$ each independently represents an oxygen atom or *—O—$(CH_2)_{k01}$—CO—O— in which * represents a binding site to —CO—, and k01 represents an integer of 1 to 7;

$R^{a01}$ each independently represent a hydrogen atom or a methyl group;

$R^{a02}$, $R^{a03}$ and $R^{a04}$ each independently represent a C1-C8 alkyl group, a C3-C18 alicyclic hydrocarbon group, or a combination of them;

$L^{a1}$ and $L^{a2}$ each independently represents an oxygen atom or *—O—$(CH_2)_{k1}$—CO—O— in which * represents a binding site to —CO—, and k1 represents an integer of 1 to 7;

$R^{a4}$ and $R^{a5}$ each independently represent a hydrogen atom or a methyl group;

$R^{a6}$ and $R^{a7}$ each independently represent a C1-C8 alkyl group, a C3-C18 alicyclic hydrocarbon group, or a combination of them;

"m1" represents an integer of 0 to 14; "n1" represents an integer of 0 to 10; and "n1'" represents 0 to 3.

$L^{a01}$ is preferably an oxygen atom or *—O—$(CH_2)_{f01}$—CO—O— in which * represents a binding site to —CO—, and "f01" represents an integer of 1 to 4, and is more preferably an oxygen atom.

"f01" represents preferably an integer of 1 to 4, more preferably 1.

Examples of the alkyl group, the alicyclic hydrocarbon group and the combination of them, represented by $R^{a02}$, $R^{a03}$ and $R^{a04}$, include those same as examples of the alkyl group, the alicyclic hydrocarbon group and the combination of them for $R^{a1}$, $R^{a2}$ and $R^{a3}$.

The alkyl group represented by $R^{a02}$, $R^{a03}$ or $R^{a04}$ is preferably a C1-C6 alkyl group.

The alicyclic hydrocarbon group represented by $R^{a02}$, $R^{a03}$ or $R^{a04}$ has preferably 8 or less, and more preferably 6 or less of carbon atoms.

The combination of the alkyl group and the alicyclic hydrocarbon group, as a group represented by $R^{a02}$, $R^{a03}$ or $R^{a04}$, has preferably 18 or less of carbon atoms. Examples of the combination include a methylcyclohexyl group, dimethylcyclohexyl group, a methylnorbornyl group, a methyladamantyl group, a (cyclohexyl)methyl group, a methyl cyclohexylmethyl group, an adamantylmethyl group, and a norbornylmethyl group.

$R^{ao2}$ and $R^{ao3}$ are each preferably a C1-C6 alkyl group, more preferably a methyl group or an ethyl group.

$R^{ao4}$ is preferably a C1-C6 alkyl group or a C5-C12 alicyclic hydrocarbon group, more preferably a methyl group, an ethyl group, a cyclohexyl group or an adamantyl group.

$L^{a1}$ and $L^{a2}$ are preferably an oxygen atom or *—O—$(CH_2)_{f1}$—CO—O— in which * represents a binding site to —CO—, and "f1" represents an integer of 1 to 4, and is more preferably an oxygen atom.

"f1" represents preferably an integer of 1 to 4, more preferably an integer of 1.

$R^{a4}$ and $R^{a5}$ are each preferably a methyl group.

Examples of the alkyl group, the alicyclic hydrocarbon group and the combination of them, represented by $R^{a6}$ and $R^{a7}$, include those same as examples for $R^{a1}$, $R^{a2}$ and $R^{a3}$.

The alkyl group represented by $R^{a6}$ or $R^{a7}$ is preferably a C1-C6 alkyl group.

The alicyclic hydrocarbon group represented by $R^{a6}$ or $R^{a7}$ has preferably 8 or less, more preferably 6 or less of carbon atoms. "m1" is preferably an integer of 0 to 3, and more preferably 0 or 1. "n1" is preferably an integer of 0 to 3, and more preferably 0 or 1. "n1'" is preferably 0 or 1.

The structural unit (a1-0) is preferably one represented by any one of the following formulae, and more preferably one represented by any one of formulae (a1-0-1) to (a1-0-10).

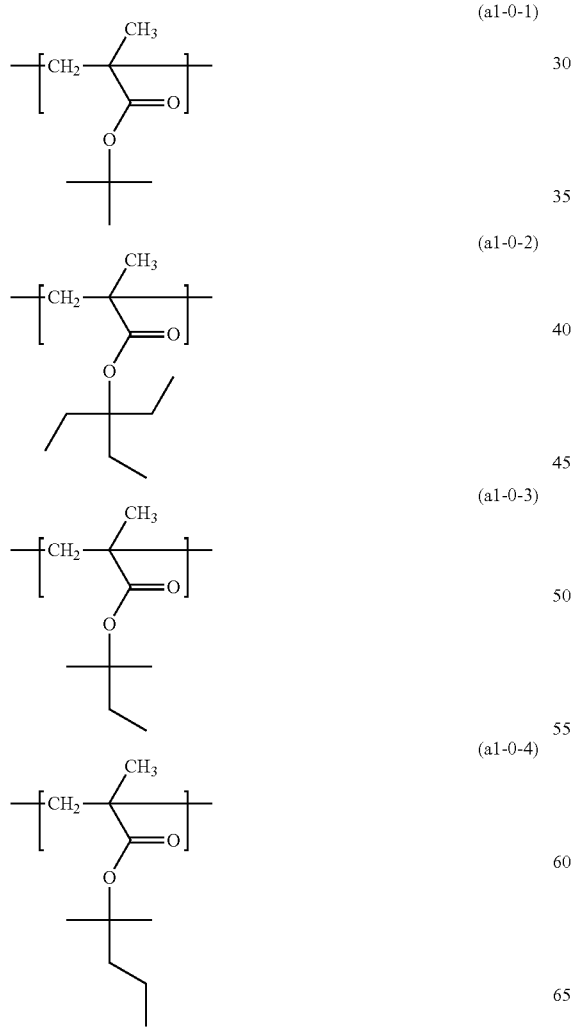

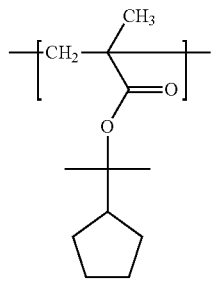
(a1-0-5)

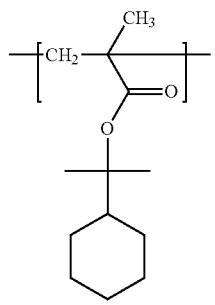
(a1-0-6)

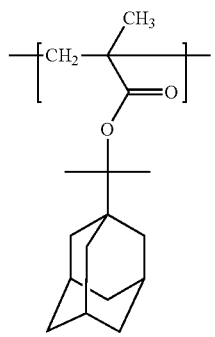
(a1-0-7)

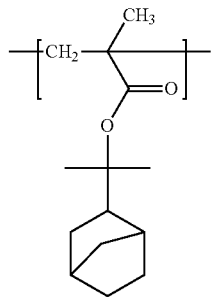
(a1-0-8)

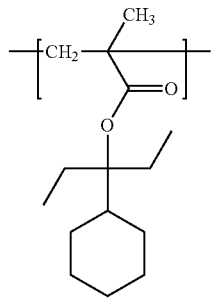
(a1-0-9)

(a1-0-10)
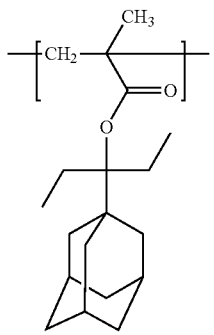
(a1-0-11)
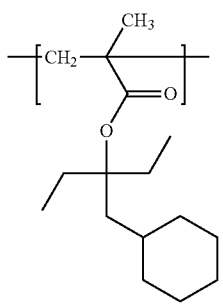
(a1-0-12)
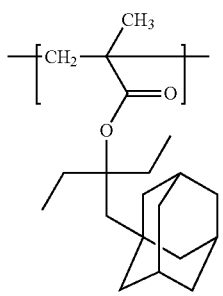
Other examples of the structural unit (a1-0) include those represented by the above-mentioned formulae in which a methyl group bonded to its main chain has been replaced by a hydrogen atom.
Examples of the structural unit (a1-1) include those derived from a monomer (a1-1) as recited in JP2010-204646A1. Preferred are the structural units represented by of formulae (a1-1-1) to (a1-1-8)
(a1-1-1)
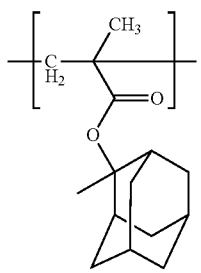
(a1-1-2)
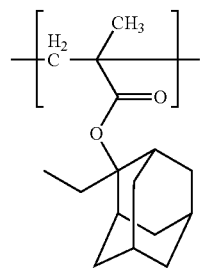
(a1-1-3)
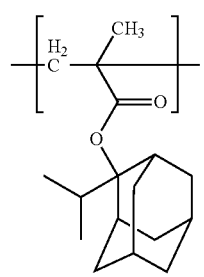
(a1-1-4)
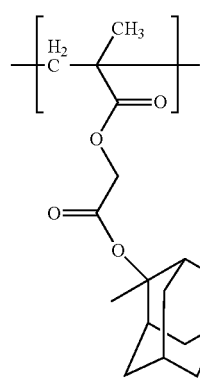
(a1-1-5)
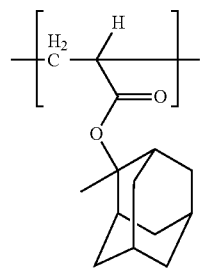
(a1-1-6)
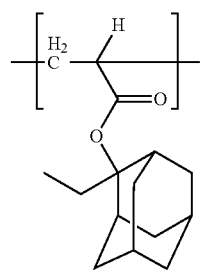

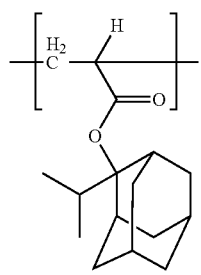
(a1-1-7)
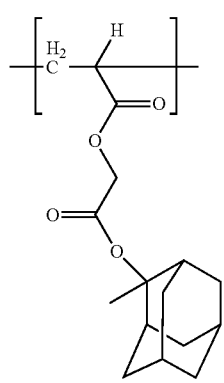
(a1-1-8)
As the structural unit (a1-2), preferred are those represented by formulae (a1-2-1) to (a1-2-12), more preferred are those represented by formulae (a1-2-3), (a1-2-4), (a1-2-9) and (a1-2-10), more preferred are those represented by formulae (a1-2-3) and (a1-2-9).
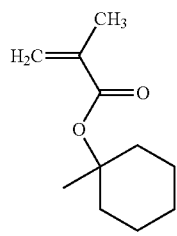
(a1-2-1)
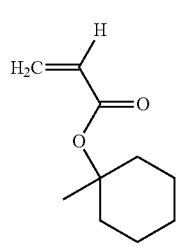
(a1-2-2)
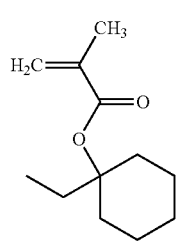
(a1-2-3)
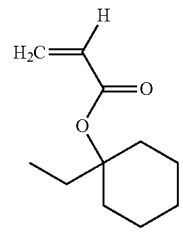
(a1-2-4)
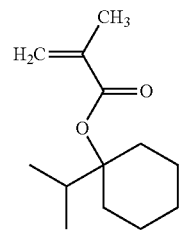
(a1-2-5)
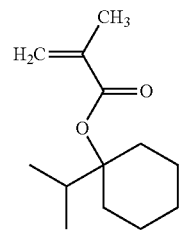
(a1-2-6)
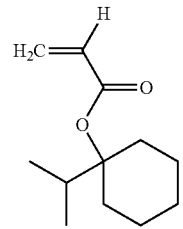
(a1-2-7)
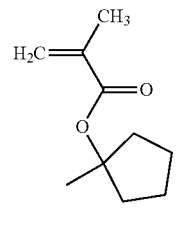
(a1-2-8)
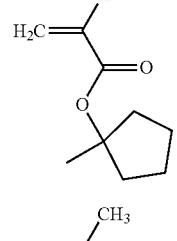
(a1-2-9)
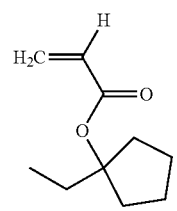
(a1-2-10)

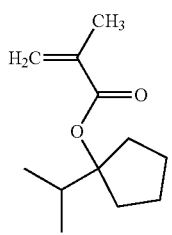
(a1-2-11)

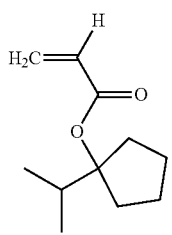
(a1-2-12)

When the resin (A) has at least one of the structural units (a1-0), (a1-1) and (a1-2), the content of the structural unit in the resin is usually 10 to 95% by mole, preferably 15 to 90% by mole, and more preferably 20 to 85% by mole based on all the structural units of the resin (A).

Another example of the structural unit (a1) includes a structural unit represented by the formula (a1-5).

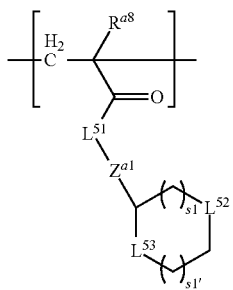
(a1-5)

In the formula (a1-5), $R^{a8}$ represents a hydrogen atom, a halogen atom or a C1-C6 alkyl group that may have a halogen atom, $Z^{a1}$ represent a single bond or *—$(CH_2)_{h3}$—CO-$L^{54}$-, where h3 represents an integer of 1 to 4, * represents a binding site to $L^{51}$, and $L^{54}$ represents —O— or —S—, $L^{51}$, $L^{52}$ and $L^{53}$ each independently represent —O— or —S—, "s1" represents an integer of 1 to 3, and
"s1'" represents an integer of 0 to 3.

The structural unit represented by the formula (a1-5) is sometimes referred to as "structural unit (a1-5)".

$R^{a8}$ is preferably a hydrogen atom, a methyl group or a trifluoromethyl group. $L^{51}$ is preferably —O—.

$L^{52}$ and $L^{53}$ are independently preferably —O— or —S—, and more preferably one is —O— and the other is —S—.

"s1" is preferably 1. "s1'" is preferably an integer of 0 to 2.

$Z^{a1}$ is preferably a single bond or *—$CH_2$—CO—O— where * represents a binding site to $L^{51}$.

Examples of the monomer from which the structural unit (a1-5) is derived include the monomers described in JP2010-61117A1. Among these, the monomers are preferably the following monomers represented by formula (a1-5-1) to formula (a1-5-4), and more preferably monomers represented by formula (a1-5-1) and formula (a1-5-2).

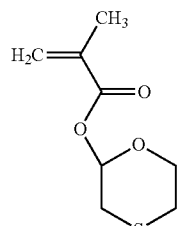
(a1-5-1)

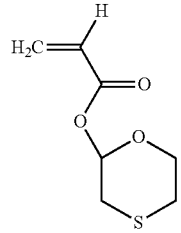
(a1-5-2)

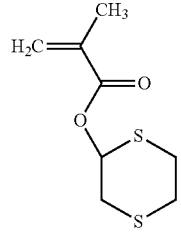
(a1-5-3)

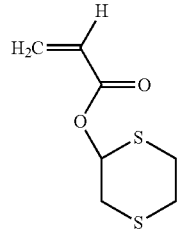
(a1-5-4)

When the resin (A) has a structural unit (a1-5), the content of the structural unit is usually 1 to 50% by mole, preferably 3 to 45% by mole and more preferably 5 to 40% by mole based on all the structural units of the resin.

Examples of the structural unit (a1) further include the following structural units.

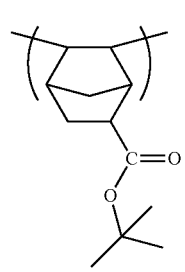
(a1-3-1)

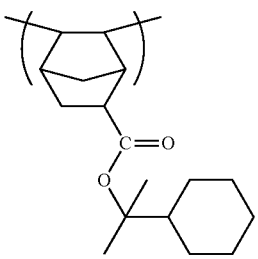
(a1-3-2)

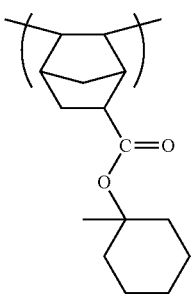
(a1-3-3)

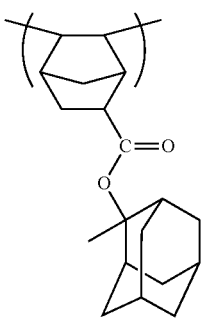
(a1-3-4)

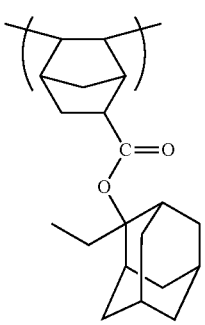
(a1-3-5)

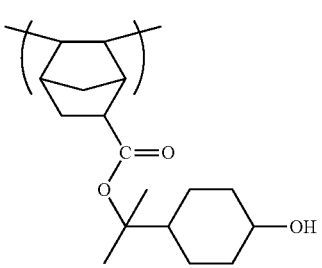
(a1-3-6)

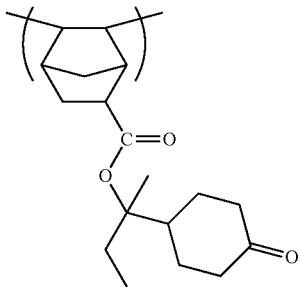
(a1-3-7)

When the resin (A) has at least one of the structural units (a1-3-1), to (a1-3-7), the content of the structural unit in the resin is usually 10 to 95% by mole, preferably 15 to 90% by mole, and more preferably 20 to 85% by mole based on all the structural units of the resin (A).

Examples of the structural unit (a1) having the group represented by formula (2) include a structural unit represented by formula (a1-4). The structural unit is sometimes referred to as "structural unit (a1-4)".

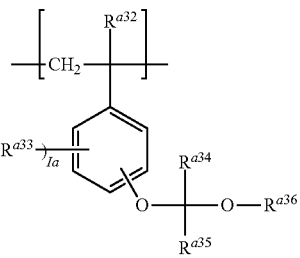
(a1-4)

In the formula, $R^{a32}$ represents a hydrogen atom, a halogen atom or a C1-C6 alkyl group that may have a halogen atom, $R^{a33}$ in each occurrence independently represent a halogen atom, a hydroxy group, a C1-C6 alkyl group, a C1-C6 alkoxy group, a C2-C4 acyl group, a C2-C4 acyloxy group, an acryloyloxy group or methacryloyloxy group, "la" represents an integer 0 to 4, $R^{a34}$ and $R^{a35}$ each independently represent a hydrogen atom or a C1-C12 hydrocarbon group; and $R^{a36}$ represents a C1-C20 hydrocarbon group, or $R^{a35}$ and $R^{a36}$ may be bonded together with a C—O bonded thereto to form a divalent C3-C20 heterocyclic group, and a methylene group contained in the hydrocarbon group or the divalent heterocyclic group may be replaced by an oxygen atom or a sulfur atom.

Examples of the alkyl group of $R^{a32}$ and $R^{a33}$ include methyl, ethyl, propyl, isopropyl, butyl, pentyl and hexyl groups. The alkyl group is preferably a C1-C4 alkyl group, and more preferably a methyl group or an ethyl group, and still more preferably a methyl group.

Examples of the halogen atom of $R^{a32}$ and $R^{a33}$ include a fluorine, chlorine, bromine and iodine atoms.

Examples of the alkyl group that may have a halogen atom include trifluoromethyl, difluoromethyl, methyl, perfluoroethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy and hexyloxy groups. The alkoxy group is preferably a C1-C4 alkoxy group, more preferably a methoxy group or an ethoxy group, and still more preferably a methoxy group. Examples of the acyl group include acetyl, propionyl and butyryl groups. Examples of the acyloxy group include acetyloxy, propionyloxy and butyryloxy groups. Examples of the hydrocarbon group for $R^{a34}$ and $R^{a35}$ are the same examples as described in $R^{a1'}$ to $R^{a2'}$ in the formula (2).

Examples of hydrocarbon group for $R^{a36}$ include a C1-C18 alkyl group, a C3-C18 alicyclic hydrocarbon group, a C6-C18 aromatic hydrocarbon group or a group formed by combining thereof.

In the formula (a1-4), $R^{a32}$ is preferably a hydrogen atom. $R^{a33}$ is preferably a C1-C4 alkoxy group, more preferably a methoxy group or an ethoxy group, and still more preferably a methoxy group. "la" is preferably 0 or 1, and more preferably 0. $R^{a34}$ is preferably a hydrogen atom. $R^{a35}$ is preferably a C1-C12 hydrocarbon group, and more preferably a methyl group or an ethyl group.

The hydrocarbon group for $R^{a36}$ is preferably a C1-C18 alkyl group, a C3-C18 alicyclic hydrocarbon group, a C6-C18 aromatic hydrocarbon group or a combination thereof, and more preferably a C1-C18 alkyl group, a C3-C18 alicyclic hydrocarbon group or a C7-C18 aralkyl group. The alkyl group and the alicyclic hydrocarbon group for $R^{a36}$ are preferably unsubstituted. When the aromatic hydrocarbon group of $R^{a36}$ has a substituent, the substituent is preferably a C6-C10 aryloxy group.

Examples of the structural unit (a1-4) include those derived from the monomers described in JP2010-204646A1. Among them, the structural unit is preferably the following ones represented by formula (a1-4-1) to formula (a1-4-8), and more preferably the structural units represented by formula (a1-4-1) to formula (a1-4-5).

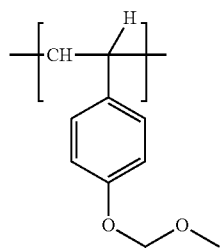

(a1-4-1)

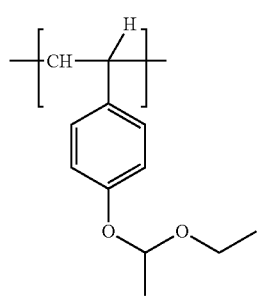

(a1-4-2)

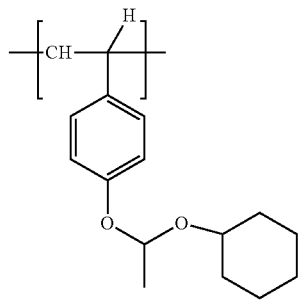

(a1-4-3)

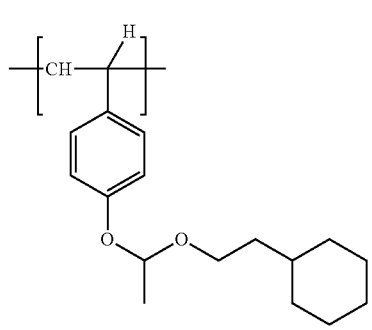

(a1-4-4)

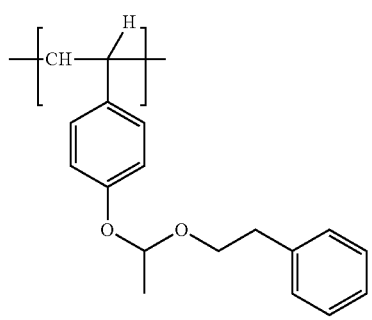

(a1-4-5)

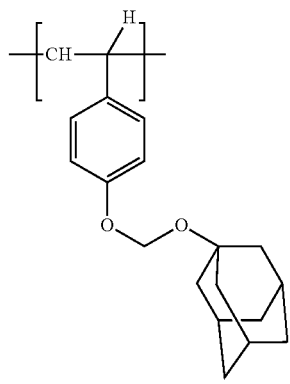

(a1-4-6)

(a1-4-7)

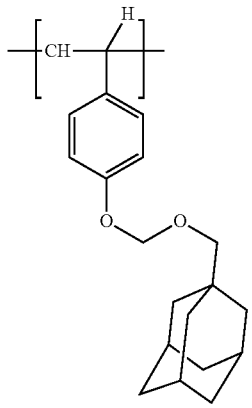

(a1-4-8)

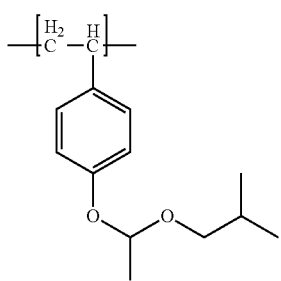

When the resin (A) has the structural unit (a1-4), the proportion thereof is preferably 10% by mole to 95% by mole, more preferably 15% by mole to 90% by mole, and still more preferably 20% by mole to 85% by mole, based on the all the structural units of the resin (A) (100% by mole).

The resin (A) may further have a structural unit having no acid-labile group.

The structural unit having no acid-labile group preferably has a hydroxy group or lactone group. The structural unit having not acid-labile group but a hydroxy group is sometimes referred to as "structural unit (a2)". The structural unit having not acid-labile group but a lactone group is sometimes referred to as "structural unit (a3)".

The resin (A) which has a structural unit (a2) or (a3) can give a photoresist composition capable of providing a photoresist pattern with improved resolution and adhesiveness to a substrate.

The structural unit (a2) may have an alcoholic hydroxy group or a phenolic-hydroxy group.

When KrF excimer laser (wavelength: 248 nm) lithography system, or a high energy laser such as electron beam and extreme ultraviolet is used as an exposure system, preferred is a resin which has a structural unit (a2) having a phenolic-hydroxy group.

When ArF excimer laser (wavelength: 193 nm) is used as an exposure system, preferred is a resin which has the structural unit (a2) having an alcoholic hydroxy group.

Examples of the structural unit (a2) having a phenolic-hydroxy group include a structural unit represented by formula (a2-0):

(a2-0)

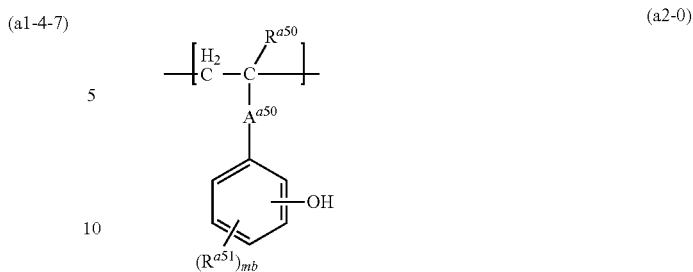

wherein $R^{a50}$ represents a hydrogen atom, a halogen atom or a C1-C6 alkyl group in which a hydrogen atom can be replaced by a halogen atom, $R^{a51}$ represents a halogen atom, a hydroxy group, a C1-C6 alkyl group, a C1-C6 alkoxy group, a C1-C6 alkylcarbonyl group, a C2-C4 alkylcarbonyloxy group, an acryloyloxy group or methacryloyloxy group, $A^{a50}$ represents a single bond or *—$X^{a51}$-($A^{a52}$-$X^{a52}$)$_{nb}$— in which * represents a binding site to the carbon atom attached to $R^{a50}$, $A^{a52}$ represents a C1-C6 alkanediyl group, $X^{a51}$ and $X^{a52}$ each independently represent —O—, —CO—O— or —O—CO—, nb represents 0 or 1, and mb represents an integer of 0 to 4.

Examples of the halogen atom for $R^{a50}$ include fluorine, chlorine, bromine and iodine atoms.

As to $R^{a50}$, examples of the alkyl group in which a hydrogen atom can be replaced by a halogen atom include a trifluoromethyl group, a difluoromethyl group, a methyl group, a perfluoroethyl group, a 1,1,1-trifluoroethyl group, a 1,1,2,2-tetrafluoroethyl group, an ethyl group, a perfluoropropyl group, a 1,1,1,2,2-pentafluoropropyl group, a propyl group, a perfluorobutyl group, a 1,1,2,2,3,3,4,4-octafluorobutyl group, a butyl group, perfluoropentyl group, a 1,1,1,2,2,3,3,4,4-nonafluoropentyl group, a pentyl group, a hexyl group and a perfluorohexyl group. $R^{a50}$ is preferably a hydrogen atom or a C1-C4 alkyl group, more preferably a hydrogen atom, a methyl group or an ethyl group, still more preferably a hydrogen atom or a methyl group.

As to $R^{a51}$, examples of an alkyl group include methyl, ethyl, n-propyl, isopropyl, n-butyl, sec-butyl, tert-butyl, pentyl and hexyl groups.

As to $R^{a51}$, examples of an alkoxy group include a methoxy group, an ethoxy group, a propoxy group, an isopropoxy group, a butoxy group, a sec-butoxy group and a tert-butoxy group. The alkoxy group represented by $R^{a51}$ is preferably a hydrogen atom or a C1-C4 alkoxy group, more preferably a methoxy group or an ethoxy group, still more preferably a methoxy group.

As to $R^{a51}$, examples of an alkylcarbony group include an acetyl group, a propionyl group and a butyryl group.

As to $R^{a51}$, examples of an alkylcarbonyloxy group include an acetyloxy group, a propionyloxy group and a butyryloxy group.

$R^{a51}$ is a methyl group.

Examples of the group represented by *—$X^{a51}$-($A^{a52}$-$X^{a52}$)$_{nb}$— include —O—, —CO—O—, —O—CO—, *—CO—O-$A^{a52}$-CO—O—, —O—CO-$A^{a52}$-O—, —O-$A^{a52}$-CO—O—, *—CO—O-$A^{a2}$-O—CO—, —O—CO-$A^{a52}$-O—CO—. Among them, *—CO—O—, *—CO—O-$A^{a52}$-CO—O— and *—O-$A^{a52}$-CO—O— are preferred.

mb represents preferably 0, 1 or 2, more preferably 0 or 1, and still more preferably 0.

In formula (a2-0), a hydroxyl group is preferably bonded to o-position or p-position, more preferably bonded to p-position.

Examples of the structural unit represented by formula (a2-0) include those derived from a monomer recited in JP2010-204634A1 and JP2012-12577A1.

Examples of the structural unit represented by the formula (a2-0) preferably include those represented by formulae (a2-0-1) to (a2-0-8), and more preferably those represented by formulae (a2-0-1), (a2-0-2), (a2-0-3) and (a2-0-4).

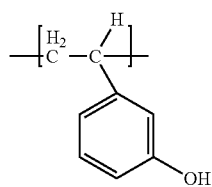
(a2-0-1)

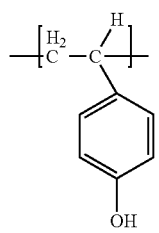
(a2-0-2)

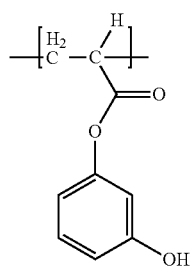
(a2-0-3)

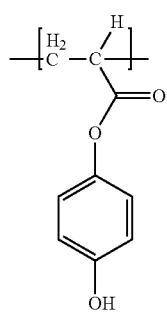
(a2-0-4)

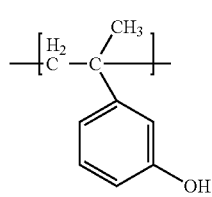
(a2-0-5)

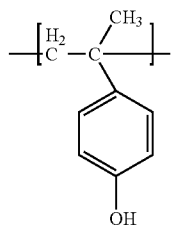
(a2-0-6)

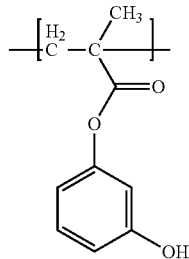
(a2-0-7)

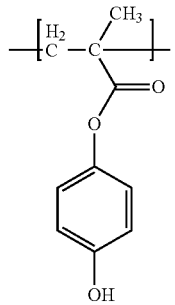
(a2-0-8)

When the resin (A) further has the structural unit (a2) having a phenolic-hydroxy group, the proportion thereof is preferably 5 to 95% by mole, more preferably 10 to 80% by mole, and still more preferably 15 to 80% by mole, based on all the structural units of the resin (A).

Preferred examples of the structural unit (a2) having an alcoholic hydroxy group include a structural unit represented by the formula (a2-1):

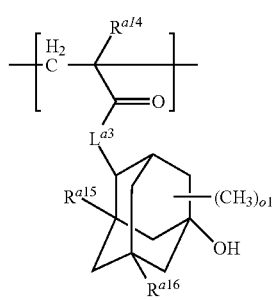
(a2-1)

wherein $R^{a14}$ represents a hydrogen atom or a methyl group, $R^{a15}$ and $R^{a16}$ each independently represent a hydrogen atom, a methyl group or a hydroxy group, $L^{a3}$ represents an oxygen atom or *—O—$(CH_2)_{k2}$—CO—O— in which * represents a binding site to —CO—, and k2 represents an integer of 1 to 7, and o1 represents an integer of 0 to 10.

In the formula (a2-1), $L^{a3}$ is preferably an oxygen atom or *—O—$(CH_2)_{f2}$—CO—O— in which * represents a binding site to —CO—, and f2 represents an integer of 1 to 4, is more preferably an oxygen atom or *—O—CH$_2$—CO—O—, and is still more preferably an oxygen atom.

R$^{a14}$ is preferably a methyl group.
R$^{a15}$ is preferably a hydrogen atom.
R$^{a16}$ is preferably a hydrogen atom or a hydroxy group.
o1 is preferably 0, 1, 2 or 3 and is more preferably 0 or 1.

Examples of the monomer from which the structural unit represented by the formula (a2-1) is derived include those mentioned in JP2010-204646A1. Examples of the structural unit represented by the formula (a2-1) preferably include those represented by formulae (a2-1-1), (a2-1-2), (a2-1-3), (a2-1-4), (a2-1-5) and (a2-1-6), and more preferably those represented by formulae (a2-1-1), (a2-1-2), (a2-1-3) and (a2-1-4), still more preferably those represented by formulae (a2-1-1) and (a2-1-3).

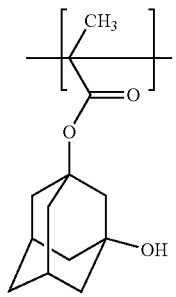

(a2-1-1)

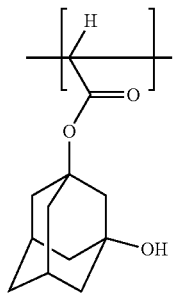

(a2-1-2)

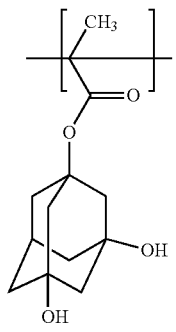

(a2-1-3)

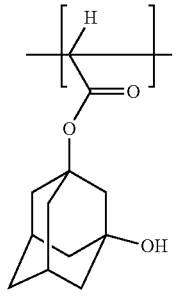

(a2-1-4)

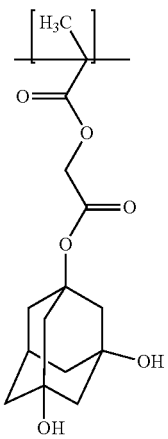

(a2-1-5)

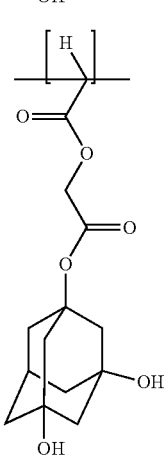

(a2-1-6)

When the resin (A) further has the structural unit represented by the formula (a2-1), the content of the structural unit represented by the formula (a2-1) is usually 1 to 45% by mole and preferably 1 to 40% by mole, more preferably 1 to 35% by mole, still more preferably 2 to 20% by mole, still further more preferably 2 to 5% by mole, based on all the structural units of the resin (A).

In the structural unit (a3), examples of the lactone ring include a monocyclic lactone ring such as β-propiolactone ring, γ-butyrolactone ring and δ-valerolactone ring, and a condensed ring formed from a monocyclic lactone ring and the other ring. Among them, preferred are γ-butyrolactone ring and a condensed lactone ring formed from γ-butyrolactone ring and another ring.

Preferable examples of the structural unit (a3) include those represented by the formulae (a3-1), (a3-2), (a3-3) and (a3-4):

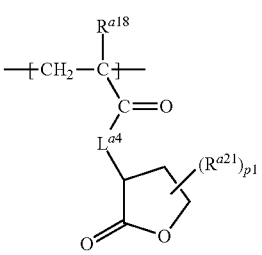

(a3-1)

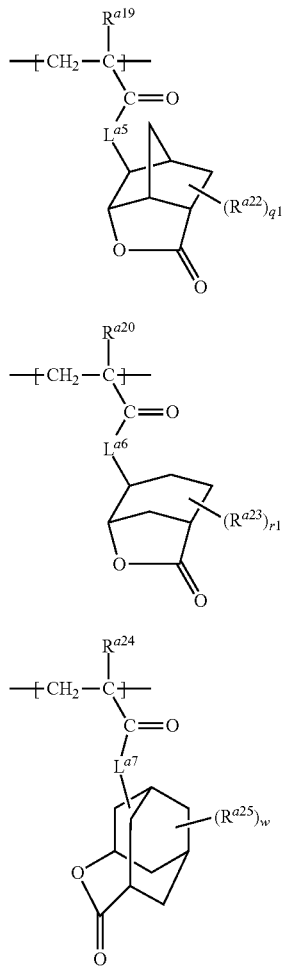

(a3-2)

(a3-3)

(a3-4)

wherein $L^{a4}$, $L^{a5}$ and $L^{a6}$ each independently represent —O— or *—O—$(CH_2)_{k3}$—CO—O— in which * represents a binding site to —CO— and k3 represents an integer of 1 to 7, $L^{a7}$ represents a single bond, —O—, *—O-$L^{a8}$-O—, *—O-$L^{a8}$-CO—O—, *—O-$L^{a8}$-CO—O-$L^{a9}$-CO—O—, or *—O-$L^{a8}$-O—CO-$L^{a9}$-O—; * represents a binding site to a carbonyl group, $L^{a8}$ and $L^{a9}$ each represent a C1-C6 alkanediyl group, $R^{a18}$, $R^{a19}$ and $R^{a20}$ each independently represent a hydrogen atom or a methyl group, $R^{a21}$ represents a C1-C4 aliphatic hydrocarbon group, $R^{a22}$, $R^{a23}$ and $R^{a25}$ are independently in each occurrence a carboxyl group, a cyano group or a C1-C4 aliphatic hydrocarbon group, $R^{a24}$ represents a hydrogen atom, a halogen atom or a C1-C6 alkyl group optionally having a halogen atom, p1 represents an integer of 0 to 5, q1 and r1 each independently represent an integer of 0 to 3, and w represents an integer of 0 to 8.

Examples of the aliphatic hydrocarbon group for $R^{a21}$, $R^{a22}$, $R^{a23}$ and $R^{a25}$ include an alkyl group such as methyl, ethyl, n-propyl, isopropyl, n-butyl, sec-butyl and tert-butyl groups.

Examples of the alkanediyl group of $L^{a8}$ and $L^{a9}$ include methylene, ethylene, propane-1,3-diyl, propane-1,2-diyl, butane-1,4-diyl, pentane-1,5-diyl, hexane-1,6-diyl, butane-1,3-diyl, 2-methylpropane-1,3-diyl, 2-methylpropane-1,2-diyl, pentane-1,4-diyl and 2-methylbutane-1,4-diyl groups.

$L^{a4}$, $L^{a5}$ and $L^{a6}$ each independently represent preferably —O— or *—O—$(CH_2)_{d1}$—CO—O— in which * represents a binding site to —CO— and d1 represents an integer of 1 to 4, and more preferably —O— and *—O—$CH_2$—CO—O—, and still more preferably —O—.

Preferably, $R^{a18}$, $R^{a19}$ and $R^{a20}$ are independently in each occurrence a methyl group.

Preferably, $R^{a22}$ and $R^{a23}$ are independently in each occurrence a carboxyl group, a cyano group or a methyl group.

p1, q1, r1 and w are independently in each occurrence preferably an integer of 0 to 2, and more preferably 0 or 1.

Examples of the halogen atom for $R^{a24}$ include fluorine, chlorine, bromine and iodine atoms.

Examples of the alkyl group for $R^{a24}$ include methyl, ethyl, n-propyl, isopropyl, n-butyl, sec-butyl, tert-butyl, n-pentyl and n-hexyl groups. The alkyl group is preferably a C1-C4 alkyl group, more preferably a methyl group or an ethyl group.

Examples of the alkyl group having a halogen atom for $R^{a24}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, tribromomethyl and triiodomethyl groups.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or *-$L^{a8}$-CO—O—, and more preferably a single bond, *—$CH_2$—CO—O— or *—$C_2H_4$—CO—O—.

The structural unit represented by formula (a3-4) is preferably one represented by formula (a3-4)'.

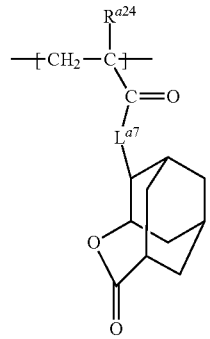

(a3-4')

In formula (a3-4)', $R^{a24}$ and $L^{a7}$ are as defined above.

Examples of the monomers from which the structural unit (a3) is derived include those mentioned in JP2010-204646A1, JP2010-122294A1, and JP2010-41274A1. Examples of the structural unit (a3) include preferably those represented by the formulae (a3-1-1) to (a3-1-4), the formulae (a3-2-1) to (a3-2-4), the formulae (a3-3-1) to (a3-3-4), and the formulae (a3-4-1) to (a3-4-12), more preferably those represented by the formulae (a3-1-1), (a3-1-2), (a3-2-1), (a3-2-3), (a3-2-4), (a3-4-1) to (a3-4-12), still more preferably those represented by the formulae (a3-4-1) to (a3-4-12), and furthermore preferably those represented by the formulae (a3-4-1) to (a3-4-6).

(a3-1-1) 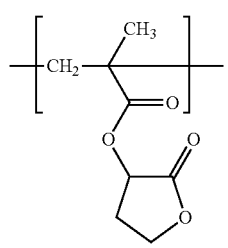
(a3-1-2) 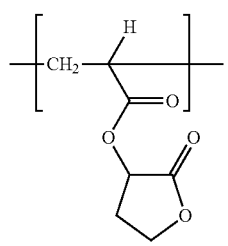
(a3-1-3) 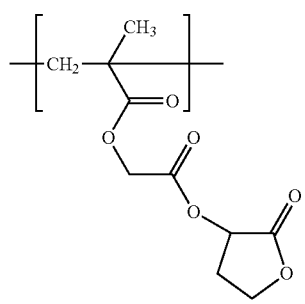
(a3-1-4) 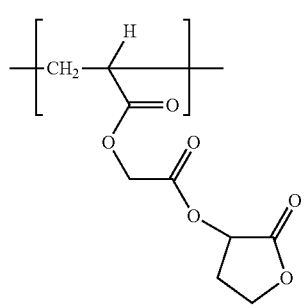
(a3-2-1) 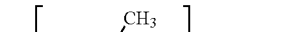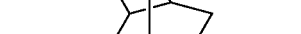
(a3-2-2) 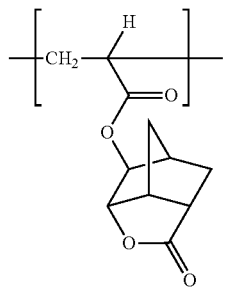
(a3-2-3) 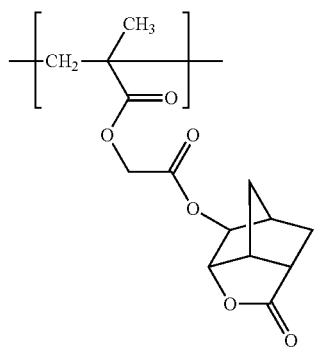
(a3-2-4) 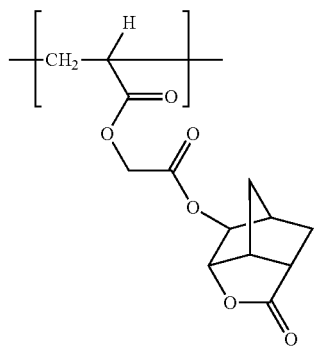
(a3-3-1) 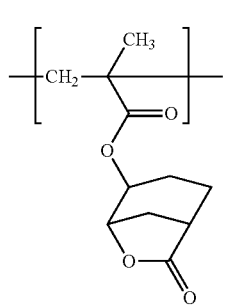
(a3-3-2) 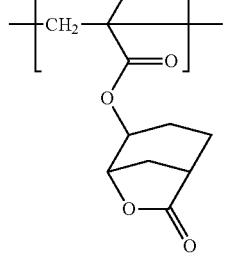

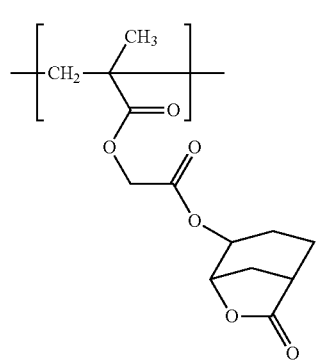
(a3-3-3)
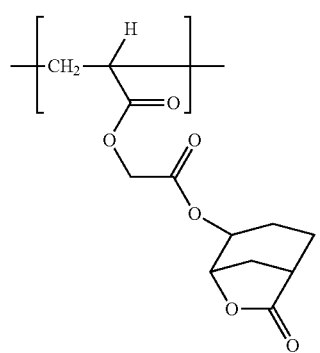
(a3-3-4)
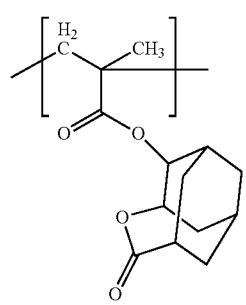
(a3-4-1)
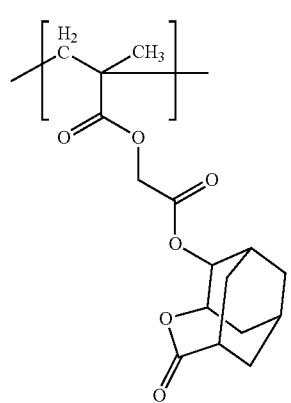
(a3-4-2)
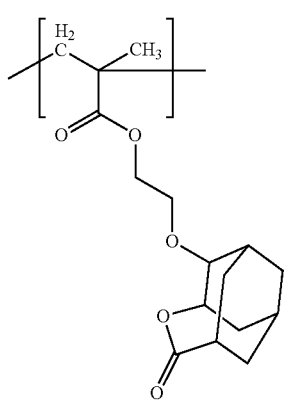
(a3-4-3)
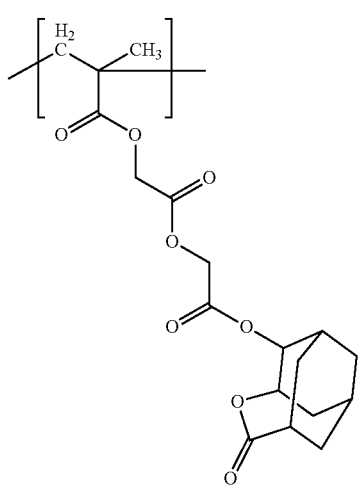
(a3-4-4)
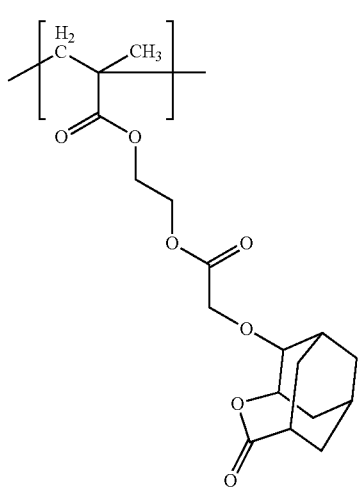
(a3-4-5)

(a3-4-6)
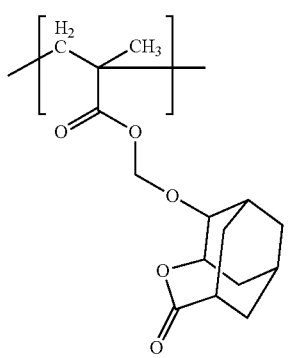
(a3-4-7)
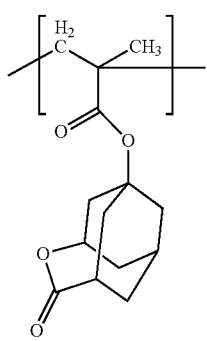
(a3-4-8)
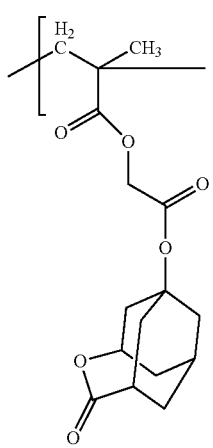
(a3-4-9)
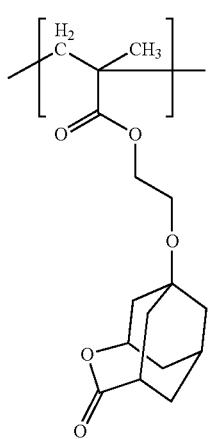
(a3-4-10)
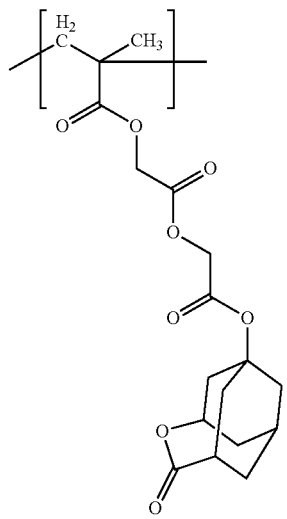
(a3-4-11)
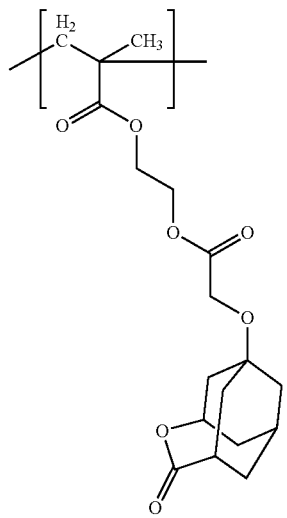
(a3-4-12)
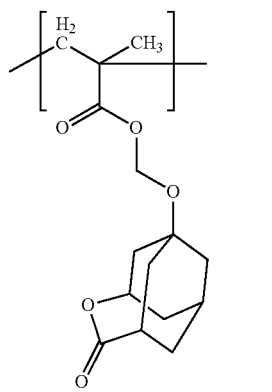
Examples of the structural unit (a3) further include those represented by formulae (a3-4-1) to (a3-4-12) in which a methyl group has been replaced by a hydrogen atom.
When the resin (A) has the structural unit (a3), the total content of the structural unit (a3) is usually 5 to 70% by mole, preferably 10 to 65% by mole, and more preferably 10 to 60% by mole, based on all the structural units of the resin (A).

When the resin (A) has the structural unit (a3-1), (a3-2), (a3-3) or (a3-4), each content of them is usually 5 to 60% by mole, preferably 5 to 50% by mole, and more preferably 10 to 50% by mole, based on all the structural units of the resin (A).

The resin (A) may further have a structural unit other than the structural units (a1), (a2) and (a3). The structural unit other than the structural units (a1), (a2) and (a3) is sometimes referred to as the "structural unit (t)".

Examples of the structural unit (t) include a structural unit having a halogen atom such as a fluorine atom and a structural unit which has a hydrocarbon group having no acid-labile group.

As to the structural unit (t), examples of the structural unit having a halogen atom, which structural unit is sometimes referred to as "structural unit (a4)", include a structural unit represented by formula (a4-0).

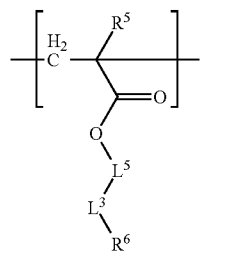
(a4-0)

In the formula (a4-0), $R^5$ represents a hydrogen atom or a methyl group, $L^5$ represents a single bond or a C1-C4 saturated aliphatic hydrocarbon group, $L^3$ represents a C1-C8 perfluoroalkanediyl group, or a C3-C12 perfluorocycloalkanediyl group, and $R^6$ represents a hydrogen atom or a fluorine atom.

Examples of the saturated aliphatic hydrocarbon group for $L^5$ include C1-C4 alkanediyl group, i.e., a linear alkanediyl group such as methylene, ethylene, propane-1,3-diyl, and butane-1,4-diyl groups; and a branched alkanediyl group such as ethane-1,1-diyl, propane-1,2-diyl, butane-1,3-diyl, 2-methylpropane-1,3-diyl and 2-methylpropane-1,2-diyl groups.

$L^5$ is preferably a single bond, methylene or ethylene group, and more preferably a single bond or a methylene group.

Examples of the perfluoroalkanediyl group for $L^3$ include difluoromethylene, perfluoroethylene, perfluoropropane-1,3-diyl, perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluorocycloalkanediyl group for $L^3$ include perfluorocyclohexanediyl, perfluorocyclopentanediyl, perfluorocycloheptanediyl and perfluoroadamantanediyl groups.

$L^3$ is preferably a C1-C6 perfluoroalkanediyl group, more preferably a C1-C3 perfluoroalkanediyl group.

Examples of the structural unit represented by formula (a4-0) include those as follow.

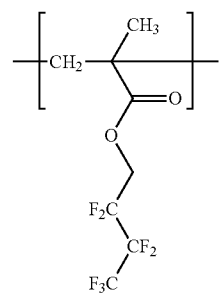
(a4-0-1)

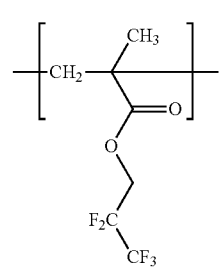
(a4-0-2)

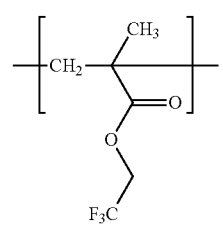
(a4-0-3)

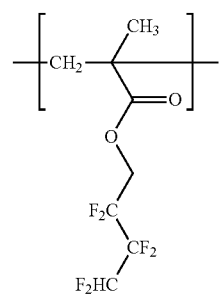
(a4-0-4)

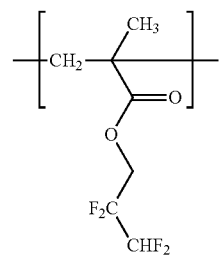
(a4-0-5)

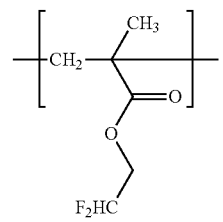
(a4-0-6)

(a4-0-7) 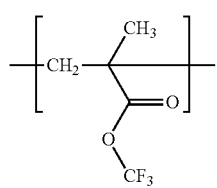
(a4-0-8) 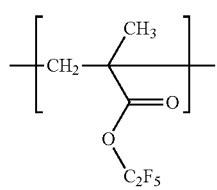
(a4-0-9) 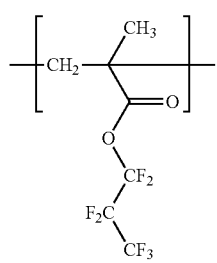
(a4-0-10) 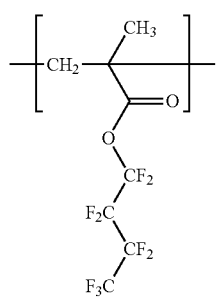
(a4-0-11) 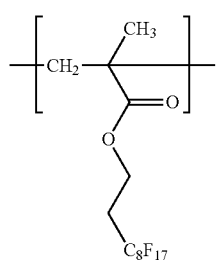
(a4-0-12) 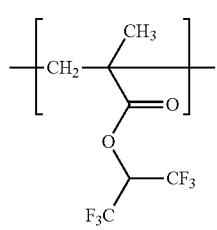
(a4-0-13) 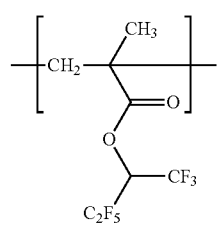
(a4-0-14) 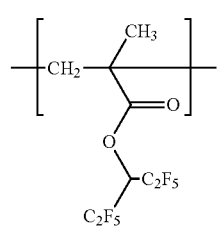
(a4-0-15) 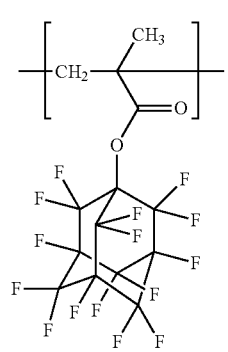
(a4-0-16) 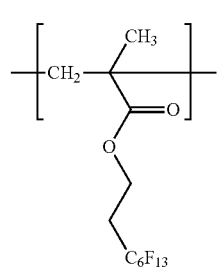
Examples of the structural unit (a4) include those represented by formula (a4-1):
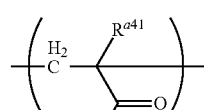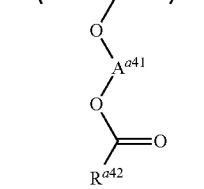 (a4-1)
wherein $R^{a41}$ represents a hydrogen atom or a methyl group,
$R^{a42}$ represents an optionally substituted C1-C20 hydrocarbon group where a methylene group may be replaced by an oxygen atom or a carbonyl group, and $A^{a41}$ represents an optionally substituted C1-C6 alkanediyl group or a group represented by formula (a-g1):

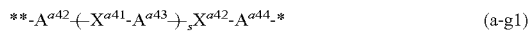
(a-g1)

wherein s represents 0 or 1,
$A^{a42}$ and $A^{a44}$ each independently represent an optionally substituted C1-C5 divalent aliphatic hydrocarbon group,
$A^{a43}$ represents a single bond or an optionally substituted C1-C5 divalent aliphatic hydrocarbon group, and
$X^{a41}$ and $X^{a42}$ each independently represent —O—, —CO—, —CO—O— or —O—CO—,
provided that the total number of the carbon atoms contained in the group of $A^{a42}$, $A^{a43}$, $A^{a44}$, $X^{a41}$ and $X^{a42}$ is 6 or less, at least one of $A^{a41}$ and $R^{a42}$ has a halogen atom as a substituent, and
* and ** represent a binding site, and * represents a binding site to —O—CO—$R^{a42}$.

The hydrocarbon group for $R^{a42}$ may be a chain aliphatic hydrocarbon group, a cyclic aliphatic hydrocarbon group, an aromatic hydrocarbon group, or a combination thereof.

The chain aliphatic hydrocarbon group and the cyclic aliphatic hydrocarbon group may have a carbon-carbon unsaturated bond, and is preferably a chain and a cyclic saturated aliphatic hydrocarbon group. Examples of the saturated aliphatic hydrocarbon group include a linear or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group include an alkyl group such as methyl, ethyl, propyl, butyl, pentyl, hexyl, heptyl, octyl, decyl, dodecyl and hexadecyl groups.

Examples of the alicyclic hydrocarbon group include a cycloalkyl group such as cyclopentyl, cyclohexyl, cycloheptyl and cyclooctyl groups; and polycyclic hydrocarbon groups such as decahydronaphtyl, adamantyl and norbornyl groups as well as groups below. * represents a binding site.

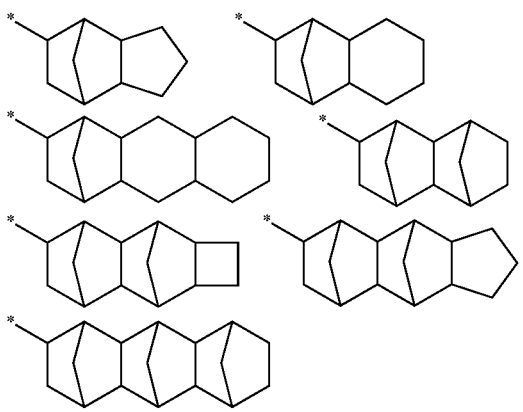

Examples of the aromatic hydrocarbon group include an aryl group such as phenyl, naphthyl, anthryl, biphenyl, phenanthryl and fluorenyl groups.

The hydrocarbon group for $R^{a42}$ is preferably a chain aliphatic hydrocarbon group, a cyclic aliphatic hydrocarbon group, and a combination thereof. The hydrocarbon group may have a carbon-carbon unsaturated bond, is preferably a chain saturated aliphatic hydrocarbon group, a cyclic saturated aliphatic hydrocarbon group, and a combination thereof.

Examples of the substituent for $R^{a42}$ include a halogen atom and a group represented by formula (a-g3):

(a-g3)

wherein $X^{a43}$ represent an oxygen atom, a carbonyl group, a carbonyloxy group or an oxycarbonyl group,
$A^{a45}$ represents a C1-C17 aliphatic hydrocarbon group that has a halogen atom, and * represents a binding site.

Examples of the halogen atom include fluorine, chlorine, bromine or iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfulorocycloalkyl group are more preferred, a C1-C6 perfluoroalkyl group is still more preferred, a C1-C3 perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

The aliphatic hydrocarbon group having the group represented by the formula (a-g3) is more preferably a group represented by formula (a-g2):

(a-g2)

wherein $A^{a46}$ represents a C1-C17 aliphatic hydrocarbon group that may have a halogen atom,
$X^{a44}$ represent a carbonyloxy group or an oxycarbonyl group,
$A^{a47}$ represents a C1-C17 aliphatic hydrocarbon group that may have a halogen atom,
provided that the total number of the carbon atoms contained in the group of $A^{a46}$, $X^{a44}$ and $A^{a47}$ is 18 or less,
at least one of $A^{a46}$ and $A^{a47}$ has a halogen atom, and
* represents a binding site to a carbonyl group.

The aliphatic hydrocarbon group for $A^{a46}$ has preferably 1 to 6 carbon atoms, more preferably 1 to 3, carbon atoms.

The aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group.

Preferred examples of *-$A^{a46}$-$X^{a44}$-$A^{a47}$ include the following ones.

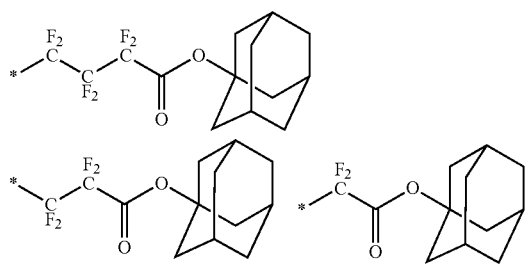

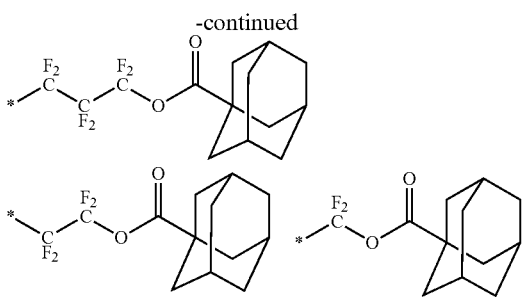

Examples of the alkanediyl group for $A^{a41}$ include a linear alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a C1-C6 alkoxy group.

$A^{a41}$ is preferably a C1-C4 alkanediyl group, more preferably a C2-C4 alkanediyl group, and still more preferably ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent on the aliphatic hydrocarbon group for $A^{a42}$, $A^{a43}$ and $A^{a44}$ include a hydroxy group and a C1-C6 alkoxy group. s is preferably 0.

Examples of the group (a-g1) in which $X^{a42}$ represents an oxygen atom include the following ones. In the formulae, * and  each represent a binding site, and  represents a binding site to —O—CO—$R^{a42}$.

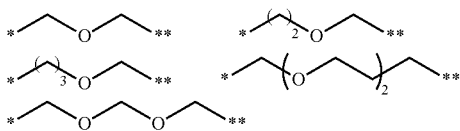

Examples of the group (a-g1) in which $X^{a42}$ represents a carbonyl group include the following ones. In the formulae, * and ** are as defined above.

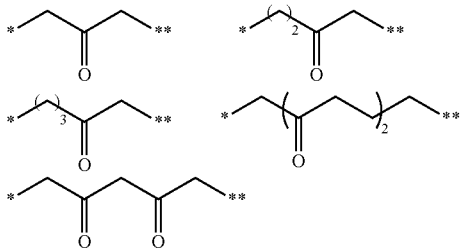

Examples of the group (a-g1) in which $X^{a42}$ represents a carbonyloxy group include the following ones. In the formulae, * and ** are as defined above.

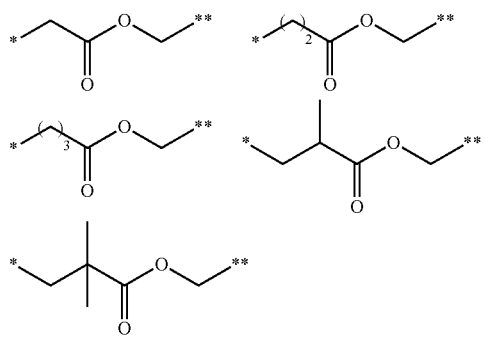

Examples of the group (a-g1) in which $X^{a42}$ represents an oxycarbonyl group include the following ones. In the formulae, * and ** are as defined above.

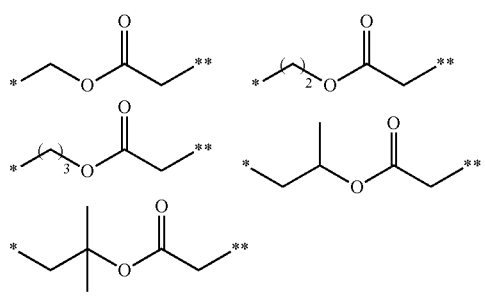

The structural unit represented by the formula (a4-1) is preferably a structural unit represented by formula (a4-2):

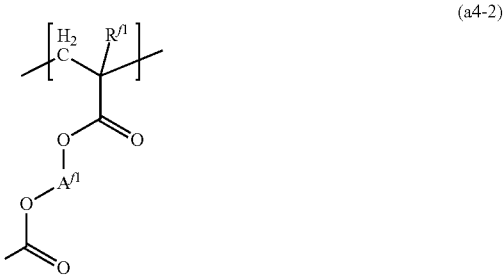

wherein $R^{f1}$ represents a hydrogen atom or a methyl group, $A^{f1}$ represent a C1-C6 alkanediyl group, and $R^{f2}$ represents a C1-C10 hydrocarbon group that has a fluorine atom.

Examples of the alkanediyl group for $A^{f1}$ include a linear alkanediyl group such as methylene, ethylene, propane-1,3-diyl, propane-1,2-diyl, butane-1,4-diyl, pentane-1,5-diyl and hexane-1,6-diyl groups; a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

Examples of the hydrocarbon group for $R^{f2}$ include an aliphatic hydrocarbon group and an aromatic hydrocarbon group. The aliphatic hydrocarbon group includes chain and cyclic groups, and a combination thereof. The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl)alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)-2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^{f1}$ is preferably a C2-C4 alkanediyl group, and more preferably an ethylene group.

$R^{f2}$ is preferably a C1-C6 fluorinated alkyl group.

Another preferred example of the structural unit represented by the formula (a4-1) includes one represented by formula (a4-3):

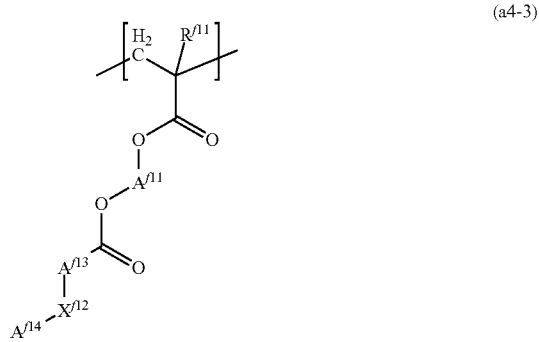

(a4-3)

In formula, $R^{f11}$ represents a hydrogen atom or a methyl group.

$A^{f11}$ represents a C1-C6 alkanediyl group.

$A^{f13}$ represents a C1-C18 chain or alicyclic hydrocarbon group which may have a fluorine atom.

$X^{f12}$ represents a carbonyloxy group or an oxycarbonyl group.

$A^{f14}$ represents a C1-C17 chain or alicyclic hydrocarbon group which may have a fluorine atom, provided that one or both of $A^{f13}$ and $A^{f14}$ represents a fluorine-containing aliphatic hydrocarbon group. Examples of the alkanediyl group represented by $A^{f11}$ include those as referred to for $A^{f11}$.

$A^{f13}$ further includes combined groups of chain hydrocarbon groups and alicyclic hydrocarbon groups.

As to $A^{f13}$, the chain or alicyclic hydrocarbon group which may have a fluorine atom is preferably a divalent saturated chain hydrocarbon group which may have a fluorine atom, more preferably a perfluoroalkanediyl group.

Examples of the divalent chain saturated hydrocarbon group which may have a fluorine atom include an alkanediyl group such as a methylene group, an ethylene group, a propanediyl group, a butanediyl group and pentanediyl group; and a perfluoroalkanediyl group such as a difluoromethylene group, a perfluoroethylene group, a perfluoropropanediyl group, a perfluorobutanediyl group and perfluoropentanediyl group.

The divalent cyclic saturated hydrocarbon group which may have a fluorine atom may be a divalent monocyclic or polycyclic group. Examples of the divalent monocyclic hydrocarbon group which may have a fluorine atom include a cyclohexanediyl group and a perfluorocyclohexanediyl group.

Examples of the divalent polycyclic hydrocarbon group which may have a fluorine atom include an adamantanediyl group, norbornanediyl group, and a perfluoroadamantanediyl group.

In the group represented by $A^{f14}$, the aliphatic hydrocarbon group includes chain saturated hydrocarbon groups, cyclic saturated hydrocarbon groups and combined groups of these saturated hydrocarbon groups.

As to $A^{f14}$, the chain or alicyclic hydrocarbon group which may have a fluorine atom is preferably a saturated aliphatic hydrocarbon group which may have a fluorine atom, more preferably a perfluoroalkanediyl group.

Examples of the chain hydrocarbon group which may have a fluorine atom include a trifluoromethyl group, a fluoromethyl group, a methyl group, a perfluoroethyl group, a 1,1,1-trifluoroethyl group, a 1,1,2,2-tetrafluoroethyl group, an ethyl group, a perfluoropropyl group, a 1,1,1,2,2-pentafluoropropyl group, propyl group, a perfluorobutyl group, 1,1,2,2,3,3,4,4-octafluorobutyl group, a butyl group, a perfluoropentyl group, 1,1,1,2,2,3,3,4,4-nonafluoropentyl group, a pentyl group, a hexyl group, a perfluorohexyl group, a heptyl group, a perfluoroheptyl group, an octyl group and a perfluorooctyl group.

The alicyclic hydrocarbon group which may have a fluorine atom may be monocyclic or polycyclic group.

Examples of the monovalent monocyclic hydrocarbon group which may have a fluorine atom include a cyclopropyl group, cyclopentyl group, cyclohexyl group, and perfluorocyclohexyl group.

Examples of the polycyclic hydrocarbon group which may have a fluorine atom include an adamantyl group, a norbornyl group, and a perfluoroadamantyl group.

Examples of the combined groups of the above-mentioned chain and alicyclic hydrocarbon groups include a cyclopropylmethyl group, a cyclobutylmethyl group, an adamantylmethyl group, a norbornylmethyl group and a perfluoroadamantylmethyl group.

In formula (a4-3), $A^{f11}$ is preferably an ethylene group.

The chain or alicyclic hydrocarbon group represented by $A^{f13}$ has preferably 6 or less, more preferably 2 to 3, of carbon atoms.

The chain or alicyclic hydrocarbon group represented by $A^{f14}$ has preferably 3 to 12, more preferably 3 to 10, of carbon atoms.

$A^{n4}$ has preferably a C3-C12 alicyclic hydrocarbon group, more preferably a cyclopropylmethyl group, a cyclopentyl group, a cyclohexyl group, a norbornyl group or an adamantyl group. Examples of the structural unit represented by formula (a4-2) include structural units represented by formula (a4-1-1) to formula (a4-1-11) and the structural units represented by these formulae in which a methyl group has been replaced by a hydrogen atom.

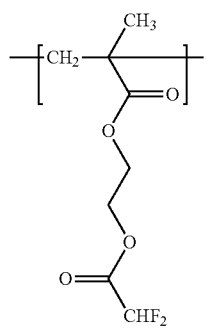
(a4-1-1)

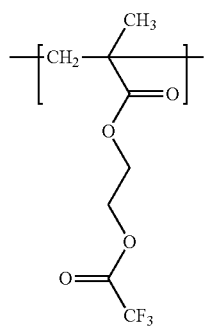
(a4-1-2)

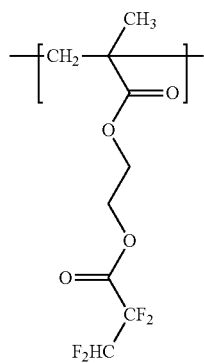
(a4-1-3)

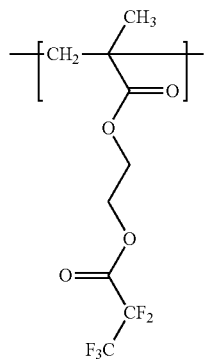
(a4-1-4)

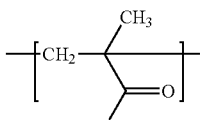
(a4-1-5)

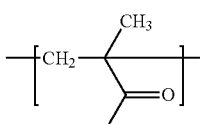
(a4-1-6)

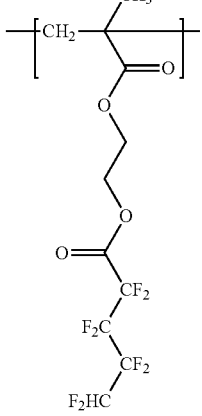
(a4-1-7)

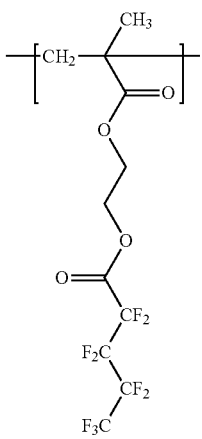
(a4-1-8)

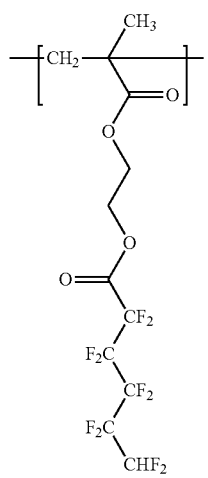 (a4-1-9)
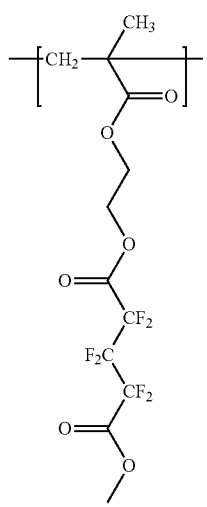 (a4-1'-1)
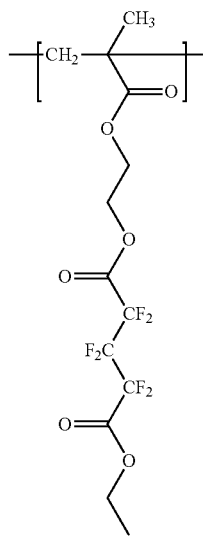 (a4-1'-2)
(a4-1-10)
(a4-1-11)
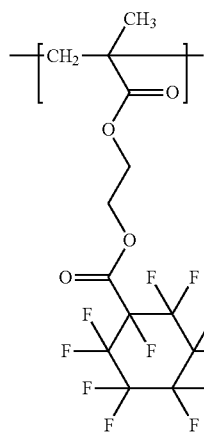
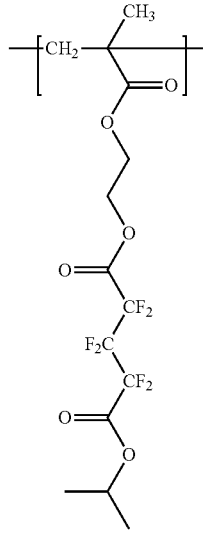 (a4-1'-3)
Examples of the structural unit represented by formula (a4-3) include structural units represented by the following formulae and the structural units represented by these formulae in which a methyl group has been replaced by a hydrogen atom.

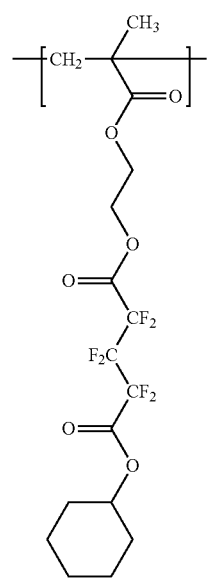
(a4-1'-4)
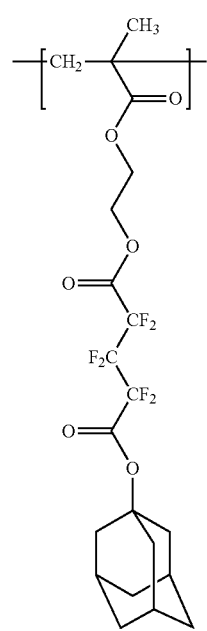
(a4-1'-5)
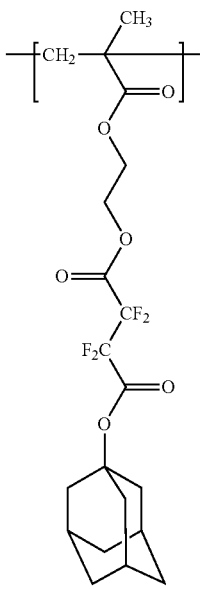
(a4-1'-6)
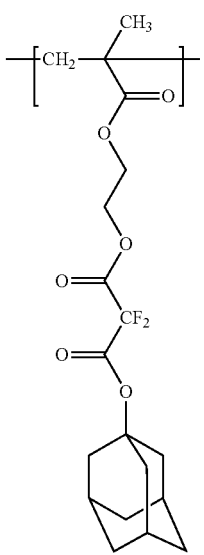
(a4-1'-7)

(a4-1'-8)
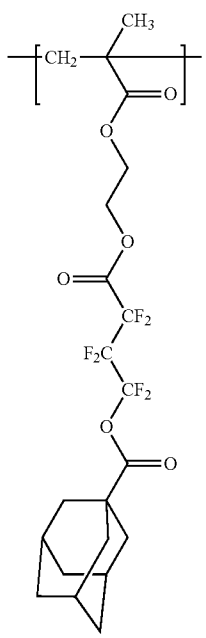

(a4-1'-9)
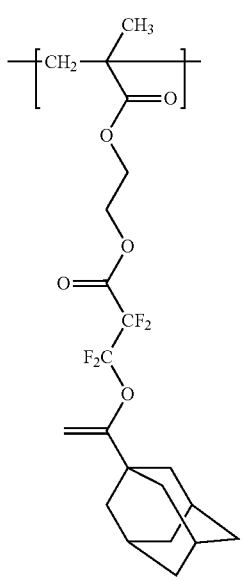

(a4-1'-10)
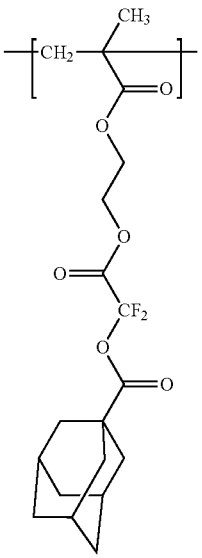

(a4-1'-11)
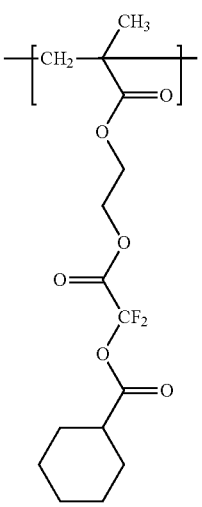

Another example of the structural unit represented by the formula (a4-1) includes one represented by formula (a4-4):

(a4-4)
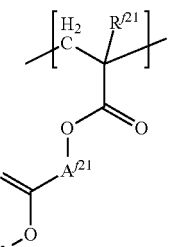

In formula, $R^{f21}$ represents a hydrogen atom or a methyl group.

$A^{f21}$ represents $-(CH_2)_{j1}-$, $-(CR_2)_{j2}-O-(CH_2)_{j3}-$ or $-(CH_2)_{j4}-C(=O)-O-(CH_2)_{j5}-$, and j1 to j5 each independently represent an integer of 1 to 6.

$R^{f22}$ represents a C1-C10 hydrocarbon group which has a fluorine atom. Examples of the hydrocarbon group represented by $R^{f22}$ include those as referred to for $R^{f2}$.

R′²² is preferably a C1-C10 fluorinated alkyl group or a C3-C10 fluorinated cycloalkyl group, more preferably a C1-C10 fluorinated alkyl group, and still more preferably a C1-C6 fluorinated alkyl group.

In formula, $A'^{21}$ represents preferably —$(CH_2)_{j1}$—, more preferably a methylene group or an ethylene group, and still more preferably a methylene group.

Examples of the structural unit represented by formula (a4-4) further include the following ones and those represented by the following formulae in which a methyl group has been replaced by a hydrogen atom.

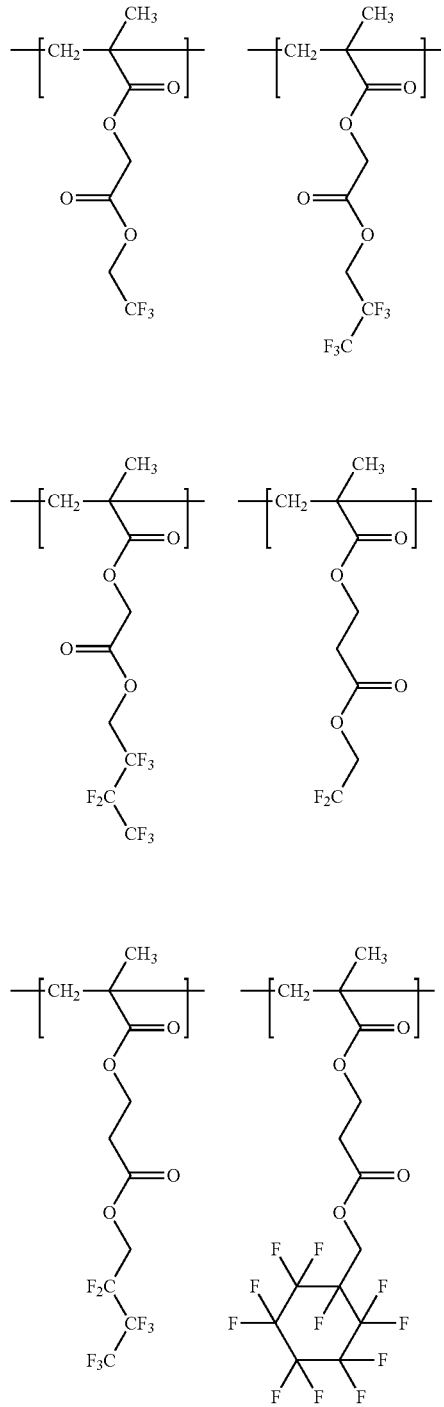

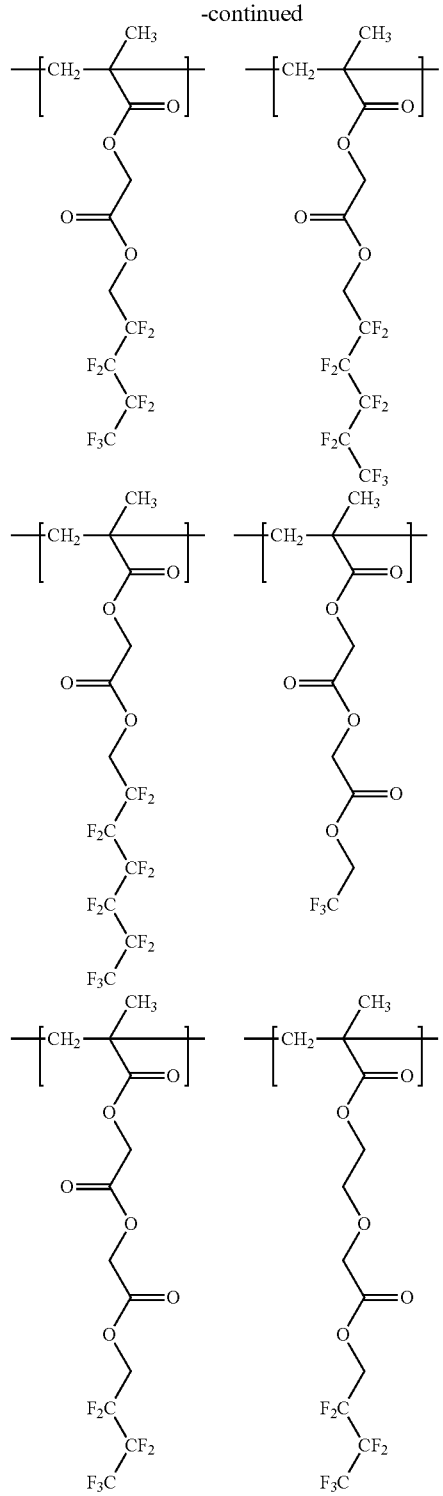

-continued

When Resin (A) has the structural unit (a4), the content thereof is usually 1 to 20% by mole, preferably 2 to 15% by mole, and more preferably 3 to 10% by mole, based on all the structural units of the resin (A)

The structural unit which has a hydrocarbon group having no acid-labile group, which is sometimes referred to as the "structural unit (a5)", may have a linear, branched or cyclic hydrocarbon group, preferably an alicyclic hydrocarbon group.

Examples of the structural unit (a5) include one represented by formula (a5-1):

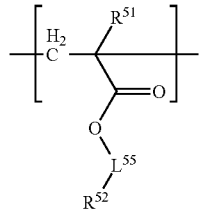
(a5-1)

where $R^{51}$ represents a hydrogen atom or a methyl group;

$R^{52}$ represents a C3-C18 alicyclic hydrocarbon group, provided that the alicyclic hydrocarbon group has no substituent on the carbon atom bonded to $L^{55}$; and $L^{55}$ represents a single bond or a C1-C8 alkanediyl group where a methylene group can be replaced by an oxygen atom or carbonyl group. The alicyclic hydrocarbon group represented by $R^{52}$ may be monocyclic or polycyclic one. Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the alicyclic hydrocarbon group having a substituent include a 3-hydroxyadamantyl group, and a 3-methyladamantyl group. Examples of the C1-C8 aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent for $R^{52}$ include 3-methyladamantyl group.

$R^{52}$ is preferably an unsubstituted C3-C18 alicyclic hydrocarbon group, and more preferably an adamantyl, norbornyl or cyclohexyl group.

Examples of the divalent saturated hydrocarbon group for $L^{55}$ include a divalent saturated aliphatic hydrocarbon group and a divalent saturated alicyclic hydrocarbon group, and a divalent saturated aliphatic hydrocarbon group is preferred.

Examples of the divalent saturated aliphatic hydrocarbon group include an alkanediyl group such as methylene, ethylene, propanediyl, butanediyl and pentanediyl groups.

Examples of the divalent saturated alicyclic hydrocarbon group include any of a monocyclic group and a polycyclic group. Examples of the monocyclic group include cycloalkanediyl group such as cyclopentanediyl and cyclohexanediyl groups. Examples of the polycyclic group include adamantanediyl and norbornanediyl groups. Examples of the saturated hydrocarbon group in which a methylene group has been replaced by an oxygen atom or a carbonyl group include groups represented by formula (L1-1) to formula (L1-4). In formula (L1-1) to formula (L1-4), * represents a binding site to an oxygen atom.

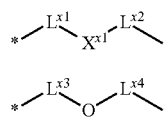
(L1-1)

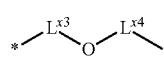
(L1-2)

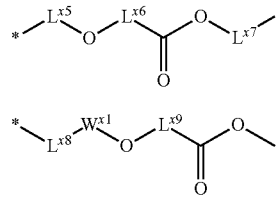
(L1-3)

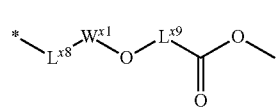
(L1-4)

In the formulae, $X^{X1}$ represents an oxycarbonyl group or a carbonyloxy group, $L^{X1}$ represents a C1-C16 divalent saturated aliphatic hydrocarbon group, $L^{X2}$ represents a single bond or a C1-C15 divalent saturated aliphatic hydrocarbon group, provided that the total number of the carbon atoms contained in the groups of $L^{X1}$ and $L^{X2}$ is 16 or less;

$L^{X3}$ represents a single bond or a C1-C17 divalent saturated aliphatic hydrocarbon group, $L^{X4}$ represents a single bond or a C1-C16 divalent saturated aliphatic hydrocarbon group, provided that the total number of the carbon atoms contained in the groups of $L^{X3}$ and $L^{X4}$ is 17 or less;

$L^{X5}$ represents a C1-C15 divalent saturated aliphatic hydrocarbon group, $L^{X6}$ and $L^{X7}$ each independently represent a single bond or a C1-C14 divalent saturated aliphatic hydrocarbon group, provided that the total number of the carbon atoms contained in the groups of $L^{X5}$, $L^{X6}$ and $L^{X7}$ is 15 or less;

$L^{X8}$ and $L^{X9}$ each independently represent a single bond or a C1-C12 divalent saturated aliphatic hydrocarbon group, $W^{X1}$ represents a C3-C15 divalent saturated alicyclic hydrocarbon group, provided that the total number of the carbon atoms contained in the groups of $L^{X8}$, $L^{X9}$ and $W^{X1}$ is 15 or less.

$L^{X1}$ is preferably a C1-C8 divalent saturated aliphatic hydrocarbon group, and more preferably a methylene group or an ethylene group.

$L^{X2}$ is preferably a single bond or a C1-C8 divalent saturated aliphatic hydrocarbon group, and more preferably a single bond.

$L^{X3}$ is preferably a C1-C8 divalent saturated aliphatic hydrocarbon group.

$L^{X4}$ is preferably a single bond or a C1-C8 divalent saturated aliphatic hydrocarbon group.

$L^{X5}$ is preferably a C1-C8 divalent saturated aliphatic hydrocarbon group, and more preferably a methylene group or an ethylene group.

$L^{X6}$ is preferably a single bond or a C1-C8 divalent saturated aliphatic hydrocarbon group, and more preferably a methylene group or an ethylene group.

$L^{X7}$ is preferably a single bond or a C1-C8 divalent saturated aliphatic hydrocarbon group.

$L^{X8}$ is preferably a single bond or a C1-C8 divalent saturated aliphatic hydrocarbon group, and more preferably a single bond or a methylene group.

$L^{X9}$ is preferably a single bond or a C1-C8 divalent saturated aliphatic hydrocarbon group, and more preferably a single bond or a methylene group.

$W^{X1}$ is preferably a C3-C10 divalent saturated alicyclic hydrocarbon group, and more preferably a cyclohexanediyl group and an adamantanediyl group.

Examples of the group represented by the formula (L1-1) include the following ones.

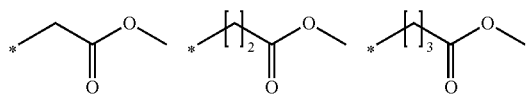
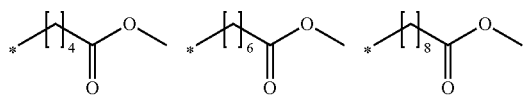
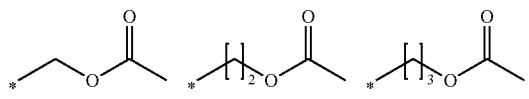
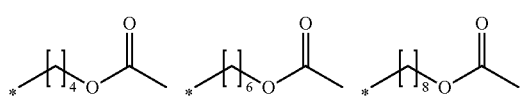
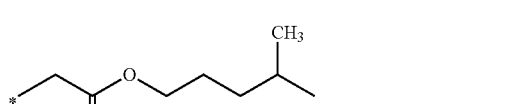
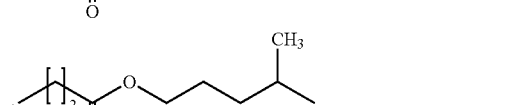

Examples of the group represented by the formula (L1-2) include the following ones.

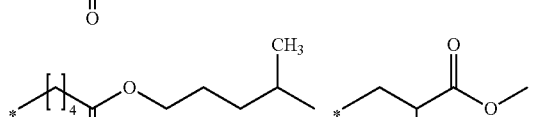

Examples of the group represented by the formula (L1-3) include the following ones.

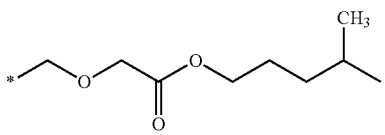
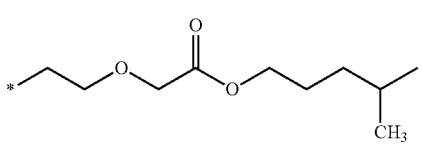
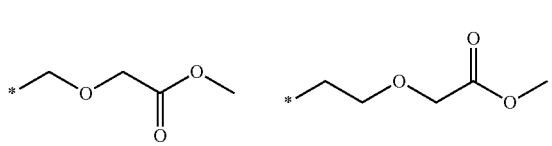

Examples of the group represented by the formula (L1-4) include the following ones.

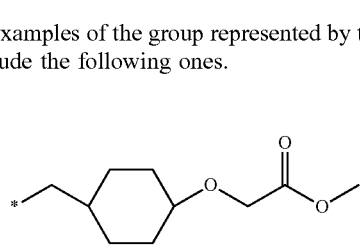
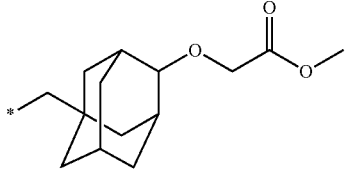
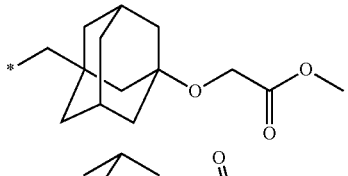
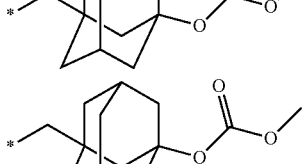
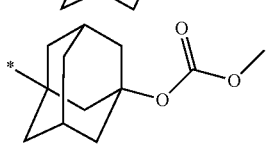

$L^{55}$ is preferably a single bond, a methylene group, and ethylene group or the group represented by the formula (L1-1), more preferably a single bond or the group represented by the formula (L1-1).

Examples of the structural unit represented by formula (a5-1) include the following ones and those represented by following formulae in which a methyl group has been replaced by a hydrogen atom.

(a5-1-1) 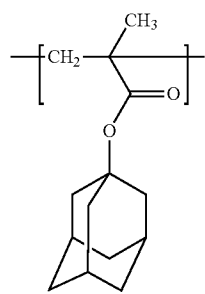
(a5-1-2) 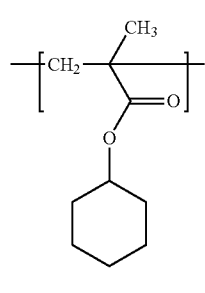
(a5-1-3) 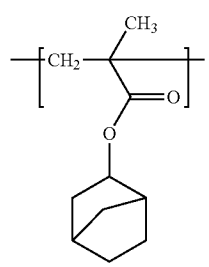
(a5-1-4) 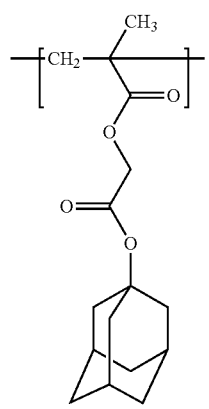
(a5-1-5) 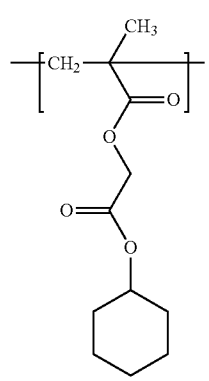
-continued
(a5-1-6) 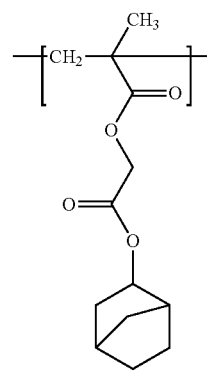
(a5-1-7) 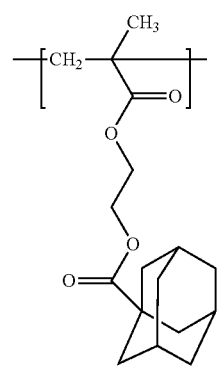
(a5-1-8) 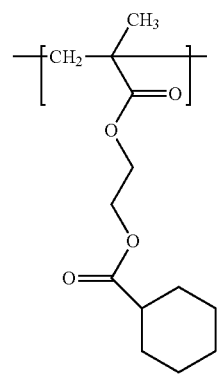
(a5-1-9) 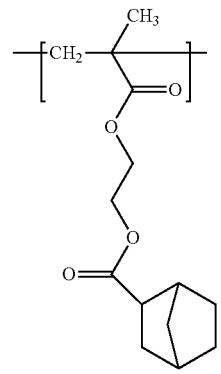

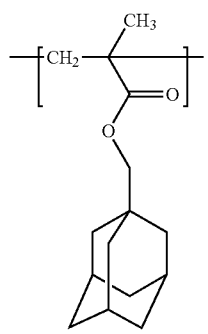 (a5-1-10)
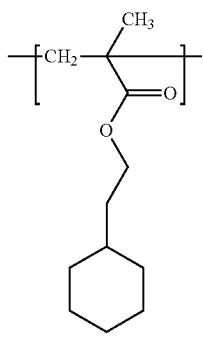 (a5-1-14)
(a5-1-11)
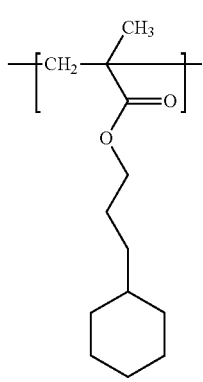 (a5-1-15)
(a5-1-12)
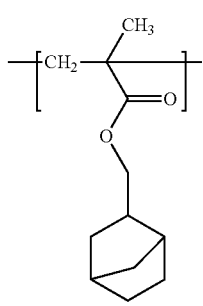 (a5-1-16)
(a5-1-13)
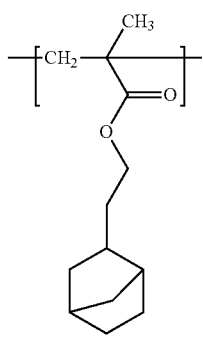 (a5-1-17)

(a5-1-18)

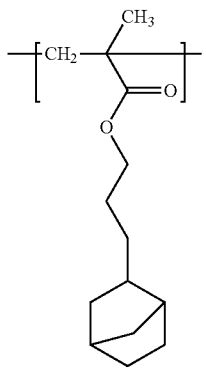

When the resin (A) further has the structural unit represented by formula (a5), the content thereof is preferably 1 to 30% by mole, more preferably 2 to 20% by mole, and still more preferably 3 to 15% by mole, based on all the structural units of the resin.

The resin (A) can further have any other structural unit known in the photoresist field.

The resin (A) is preferably a resin which comprises the structural unit (a1), more preferably a resin which comprises the structural unit (a1) and the structural unit (s).

The resin (A) has, as the structural unit (a1), preferably at least one, more preferably two or more structural units selected from the structural unit (a1-1), the structural unit (a1-2).

The resin (A) has, as the structural unit (s), preferably at least one structural unit selected from the structural unit (a2) and the structural unit (a3). For the resin (A), the structural unit (a2) is preferably the structural unit represented by formula (a2-1). For the resin (A), the structural unit (a2) is preferably at least one structural unit selected from the group consisting of the structural units represented by formulae (a3-1-1), (a3-1-2), (a3-1-3), (a3-1-4), (a3-2-1), (a3-2-2), (a3-2-3), (a3-2-4), (a3-4-1) and (a3-4-2).

The resin (A) can be produced by polymerizing a monomer as mentioned above in a manner of radical polymerization or a known polymerization method.

The weight-average molecular weight of the resin (A) is usually 2,000 or more, preferably 2,500 or more, and more preferably 3,000 or more, and usually 50,000 or less, preferably 30,000 or less, more preferably 15,000 or less.

The weight-average molecular weight can be measured with gel permeation chromatography (standard: polyethylene). The detailed method of measurement is described in Examples of the present specification.

Examples of another resin than Resin (A) include what consists of a structural unit having no acid-labile group, preferably what has the structural unit having a halogen atom such as the structural unit (a4). Here, such another resin is referred to as "Resin (X)". Resin (X) may be one which consists of the structural unit having a fluorine atom, or one which further comprise the structural unit (a2), the structural unit (a3), the structural unit (a5) or another structural unit having no acid-labile group, known in the art. Resin (X) preferably contains the structural unit having a fluorine atom and the structural unit (a5).

In Resin (X), the content of the structural unit (a4) is preferably 40% by mole or more, more preferably 45% by mole or more, still more preferably 50% by mole or more based on sum of the structural units in the resin.

Resin (X) usually has 8000 or more of the weight-average molecular weight, preferably 10000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

The resin (X) can be obtained by conducting polymerization reaction of the corresponding monomer or monomers. The polymerization reaction is usually carried out in the presence of a radical initiator. This polymerization reaction can be conducted according to known methods.

When the photoresist composition contains Resin (X), the content of the resin is preferably 1 to 60 weight parts, more preferably 1 to 50 weight parts, and still more preferably 1 to 40 weight parts, and further still more preferably 2 to 30 weight parts, relative to 100 parts of Resin (A).

The total content of the resins in the photoresist composition of the present invention is usually 80% by mass or more, preferably 90% by mass or more, based on sum of solid component, and usually 99% by mass or less based on sum of solid component.

In this specification, "solid component" means components other than solvent in the photoresist composition.

<Acid Generator (B)>

The photoresist composition of the disclosure may further contain a known acid generator which is sometimes referred to as "acid generator (B)".

The acid generator (B) may be a nonionic acid generator or an ionic acid generator. Examples of the nonionic acid generator include an organo-halogen compound, a sulfonate compound such as a 2-nitrobenzylsulfonate, an aromatic sulfonate, an oxime sulfonate, an N-sulfonyloxyimide, a sulfonyloxyketone and diazonaphthoquinone 4-sulfonate, and a sulfone compound such as a disulfone, a ketosulfone and a sulfonyldiazomethane. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonylmethide anion.

Specific examples of the acid generator (B) include acid generators described in JP 63-26653 A, JP 55-164824 A, JP62-69263 A, JP63-146038A, JP63-163452A, JP62-153853A, JP63-146029A, U.S. Pat. No. 3,779,778, U.S. Pat. No. 3,849,137, DE Patent No. 3914407 and EP Patent No. 126,712. Other examples of that include acid generators described in JP2013-68914A, JP2013-3155A and JP2013-11905A.

The acid generator for the photoresist composition is preferably a fluorine-containing acid generator, and more preferably a fluorine-containing organic sulfonate acid generator.

Preferable examples of the acid generator include a salt represented by the formula (B1):

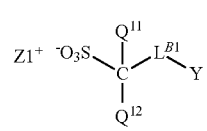

(B1)

wherein $Q^{11}$ and $Q^{12}$ each independently represent a fluorine atom or a C1-C6 perfluoroalkyl group, $L^{B1}$ represents a single bond or a C1-C24 divalent saturated hydrocarbon group in which a methylene group can be replaced by —O— or —CO— and in which a hydrogen atom can be replaced by a fluorine atom or a hydroxy group, and Y represents a methyl group which can have a substituent or a C3-C18 monovalent alicyclic hydrocarbon group which can have a substituent and in which a methylene group can be replaced by —O—, —CO— or —SO$_2$—, and $Z1^+$ represents an organic cation.

For $Q^{11}$ and $Q^{12}$, examples of the perfluoroalkyl group include examples of those for $Q^1$ and $Q^2$, and a trifluoromethyl group is preferred. $Q^{11}$ and $Q^{12}$ each independently preferably represent a fluorine atom or a trifluoromethyl group, and $Q^{11}$ and $Q^{12}$ are more preferably fluorine atoms.

Examples of the divalent saturated hydrocarbon group represented by $L^{B1}$ include linear alkanediyl groups, branched chain alkanediyl groups, a monocyclic divalent alicyclic hydrocarbon group, a polycyclic divalent alicyclic hydrocarbon group and combinations of them. Specific examples of them include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and heptadecane-1,17-diyl group; branched chain alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and 2-methylbutane-1,4-diyl group; a monocyclic divalent alicyclic hydrocarbon group such as a cyclobutan-1,3-diyl group, cyclopentane-1,3-diyl group, a cyclohexane-1,4-diyl group, and a cyclooctane-1,5-diyl group; and a polycyclic divalent alicyclic hydrocarbon group such as a norbornane-1,4-diyl group, a norbornane-2,5-diyl group, an adamantane-1,5-diyl group and an adamantane-2,6-diyl group.

When $L^{B1}$ represents a divalent saturated hydrocarbon group in which a methylene group has been replaced by an oxygen atom or a carbonyl group, examples of $L^{B1}$ include the moiety represented by any one of formulae (b1-1) to (b1-3) as follow;

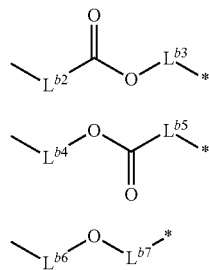

(b1-1)

(b1-2)

(b1-3)

wherein $L^{b2}$ represents a single bond or a C1 to C22 divalent saturated hydrocarbon group in which a hydrogen atom can be replaced by a fluorine atom, and $L^{b3}$ represents a single bond or a C1 to C22 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b2}$ and $L^{b3}$ is up to 22;

$L^{b4}$ represents a single bond or a C1 to C22 divalent saturated hydrocarbon group in which a hydrogen atom can be replaced by a fluorine atom, and $L^{b5}$ represents a single bond or a C1 to C22 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b4}$ and $L^{b5}$ is up to 22;

$L^{b6}$ represents a C1 to C23 divalent saturated hydrocarbon group in which a hydrogen atom can be replaced by a fluorine atom or a hydroxyl group, and $L^{b7}$ represents a single bond or a C1 to C23 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b6}$ and $L^{b7}$ is up to 23; and * represents a binding site to Y.

In formula (b1-1) to formula (b1-3), when a methylene group has been replaced by an oxygen atom or a carbonyl group, the carbon number of the saturated hydrocarbon group corresponds to the number of the carbon atom before replacement.

Examples of the divalent saturated hydrocarbon group are the same examples as the divalent saturated hydrocarbon group of $L^{b1}$.

$L^{b2}$ is preferably a single bond.

$L^{b3}$ is preferably a C1 to C4 divalent saturated hydrocarbon group.

$L^{b4}$ is preferably a C1 to C8 divalent saturated hydrocarbon group where a hydrogen atom can be replaced by a fluorine atom.

$L^{b5}$ is preferably a single bond or a C1 to C8 divalent saturated hydrocarbon group.

$L^{b6}$ is preferably a single bond or a C1 to C4 divalent saturated hydrocarbon group where a hydrogen atom can be replaced by a fluorine atom.

$L^{b7}$ is preferably a single bond or a C1 to C18 divalent saturated hydrocarbon group where a hydrogen atom can be replaced by a fluorine atom or a hydroxy group, and where a methylene group can be replaced by an oxygen atom or a carbonyl group.

Among these, the group represented by the formula (b1-1) or the formula (b1-3) is preferred.

Examples of the divalent group represented by the formula (b1-1) include the following groups represented by formula (b1-4) to formula (b1-8):

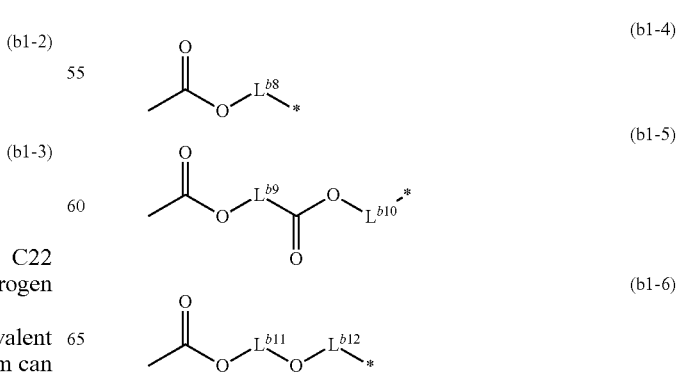

(b1-4)

(b1-5)

(b1-6)

(b1-7)

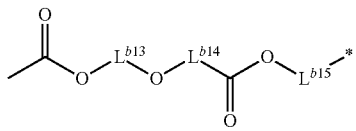

(b1-8)

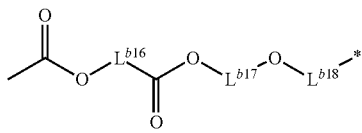

wherein $L^{b8}$ represents a single bond or a C1 to C22 divalent saturated hydrocarbon group where a hydrogen atom can be replaced by a fluorine atom or a hydroxy group;

$L^{b9}$ represents a C1 to C20 divalent saturated hydrocarbon group, and $L^{b10}$ represents a single bond or a C1 to C19 divalent saturated hydrocarbon group where a hydrogen atom can be replaced by a fluorine atom or a hydroxy group, provided that the total number of carbon atoms contained in the group of $L^{b9}$ and $L^{b10}$ is 20 or less;

$L^{b11}$ represents a C1 to C21 divalent saturated hydrocarbon group, and $L^{b12}$ represents a single bond or a C1 to C20 divalent saturated hydrocarbon group where a hydrogen atom can be replaced by a fluorine atom or a hydroxy group, provided that the total number of carbon atoms contained in the group of $L^{b11}$ and $L^{b12}$ is 21 or less;

$L^{b13}$ represents a C1 to C19 divalent saturated hydrocarbon group, $L^{b14}$ represents a single bond or a C1 to C18 divalent saturated hydrocarbon group, and $L^{b15}$ represents a single bond or a C1 to C18 divalent saturated hydrocarbon group where a hydrogen atom can be replaced by a fluorine atom or a hydroxy group, provided that the total number of carbon atoms contained in the group of $L^{b13}$, $L^{b14}$ and $L^{b15}$ is 19 or less;

$L^{b16}$ represents a C1 to C18 divalent saturated hydrocarbon group, $L^{b17}$ represents a C1 to C18 divalent saturated hydrocarbon group, and $L^{b18}$ represents a single bond or a C1 to C17 divalent saturated hydrocarbon group where a hydrogen atom can be replaced by a fluorine atom or a hydroxy group, provided that the total number of carbon atoms contained in the group of $L^{b16}$, $L^{b17}$ and $L^{b18}$ is 19 or less; and * represents a binding site to Y.

$L^{b8}$ is preferably a C1 to C4 divalent saturated hydrocarbon group.

$L^{b9}$ is preferably a C1 to C8 divalent saturated hydrocarbon group.

$L^{b10}$ is preferably a single bond or a C1 to C19 divalent saturated hydrocarbon group, and more preferably a single bond or a C1 to C8 divalent saturated hydrocarbon group.

$L^{b11}$ is preferably a C1 to C8 divalent saturated hydrocarbon group.

$L^{b12}$ is preferably a single bond or a C1 to C8 divalent saturated hydrocarbon group.

$L^{b13}$ is preferably a C1 to C12 divalent saturated hydrocarbon group.

$L^{b14}$ is preferably a C1 to C6 divalent saturated hydrocarbon group.

$L^{b15}$ is preferably a single bond or a C1 to C18 divalent saturated hydrocarbon group, and more preferably a single bond or a C1 to C8 divalent saturated hydrocarbon group.

$L^{b16}$ is preferably a C1 to C12 divalent saturated hydrocarbon group.

$L^{b17}$ is preferably a C1 to C6 divalent saturated hydrocarbon group.

$L^{b18}$ is preferably a single bond or a C1 to C17 divalent saturated hydrocarbon group, and more preferably a single bond or a C1 to C4 divalent saturated hydrocarbon group.

Examples of the divalent group represented by the formula (b1-3) include the following groups represented by formula (b1-9) to formula (b1-11):

(b1-9)

$\diagup L^{b19}\diagdown_O\diagup L^{b20}\diagdown_*$ (b1-10)

(b1-11)

wherein $L^{b19}$ represents a single bond or a C1 to C23 divalent saturated hydrocarbon group where a hydrogen atom can be replaced by a fluorine atom, and $L^{b20}$ represent a single bond or a C1 to C23 divalent saturated hydrocarbon group where a hydrogen atom can be replaced by a fluorine atom, a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b19}$ and $L^{b20}$ is 23 or less;

$L^{b21}$ represents a single bond or a C1 to C21 divalent saturated hydrocarbon group where a hydrogen atom can be replaced by a fluorine atom, $L^{b22}$ represents a single bond or a C1 to C21 divalent saturated hydrocarbon group, and $L^{b23}$ represents a single bond or a C1 to C21 divalent saturated hydrocarbon group where a hydrogen atom can be replaced by a fluorine atom, a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b21}$, $L^{b22}$ and $L^{b23}$ is 21 or less;

$L^{b24}$ represents a single bond or a C1 to C20 divalent saturated hydrocarbon group where a hydrogen atom can be replaced by a fluorine atom, $L^{b25}$ represents a single bond or a C1 to C21 divalent saturated hydrocarbon group, and $L^{b26}$ represents a single bond or a C1 to C20 divalent saturated hydrocarbon group where a hydrogen atom can be replaced by a fluorine atom, a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b24}$, $L^{b25}$ and $L^{b26}$ is 21 or less;

and * represents a binding site to Y.

In formula (b1-9) to formula (b1-11), when a hydrogen atom has been replaced by an acyloxy group, the carbon number of the saturated hydrocarbon group corresponds to the number of the carbon atom, CO and O in addition to the carbon number of the saturated hydrocarbon group.

$L^{B1}$ is preferably one represented by formulae (b1-1), (b1-2) or (b1-3), more preferably *²—CO—O—$(CH_2)_{t1}$— or *²—$(CH_2)_{t2}$—O—CO— where t1 represents an integer of 0 to 6, t2 represents an integer of 2 to 6, and *² represents a binding position to —C(Q¹¹)(Q¹²)-.
The monovalent alicyclic hydrocarbon group for Y may be a monocyclic one or polycyclic one such as a spiro ring.
Preferred examples of the alicyclic hydrocarbon group represented by Y include those represented by the formulae (Y1) to (Y38).
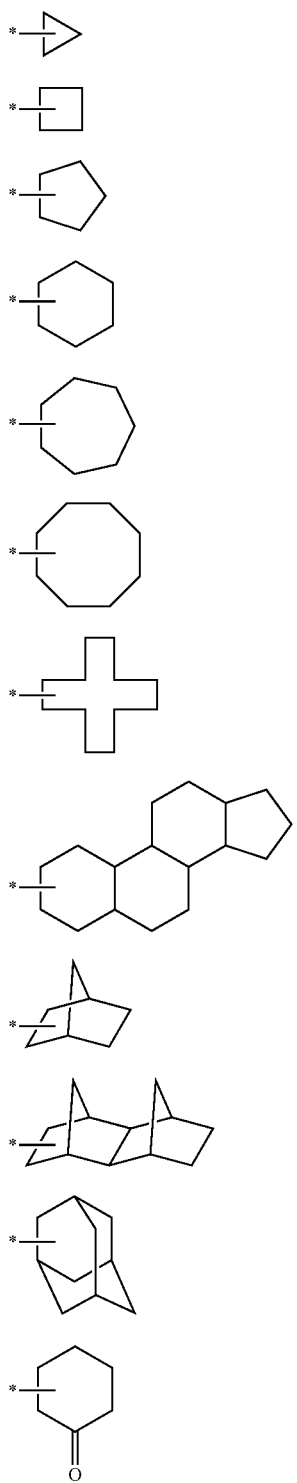
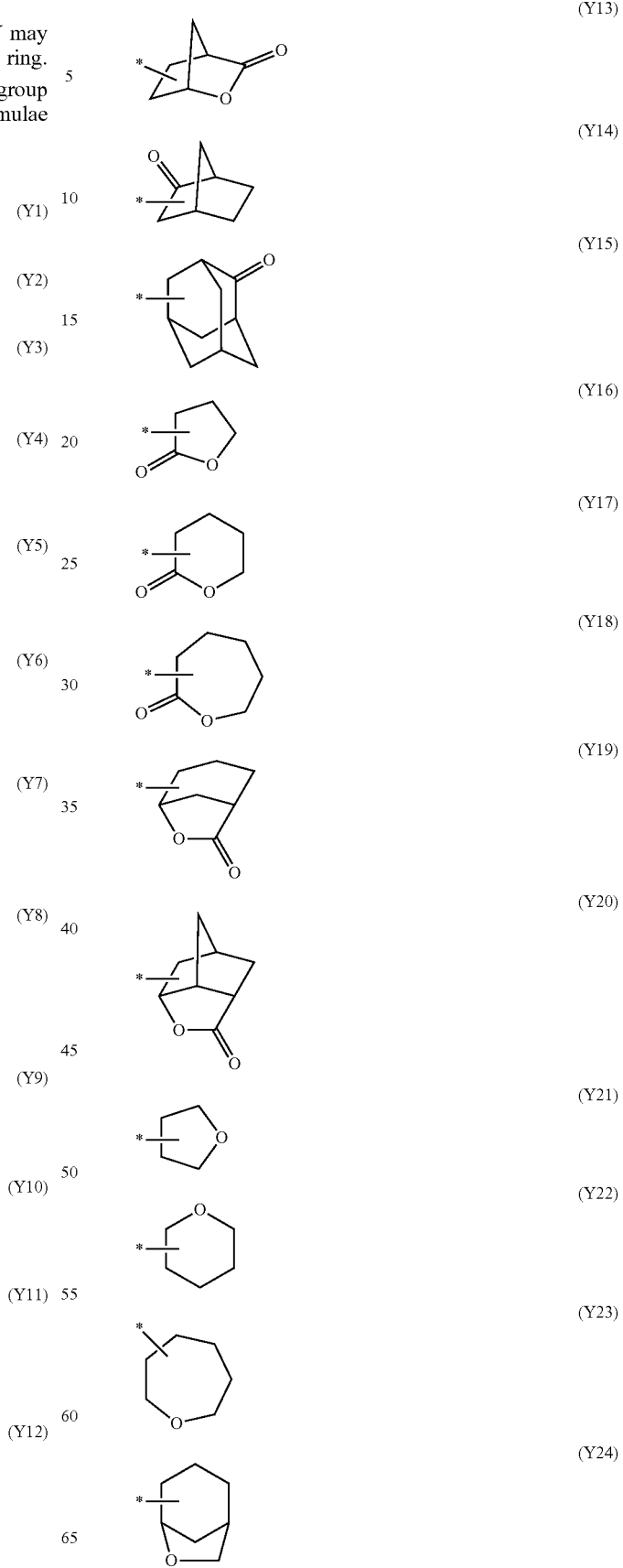

(Y25) 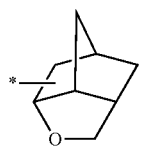

(Y26) 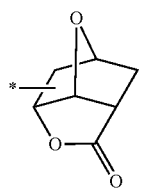

(Y27) 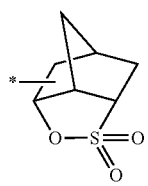

(Y28) 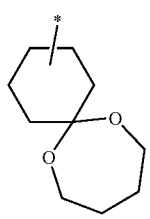

(Y29) 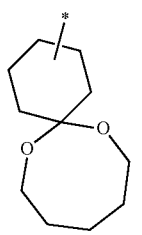

(Y30) 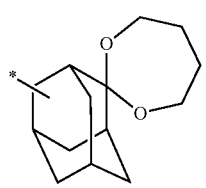

(Y31) 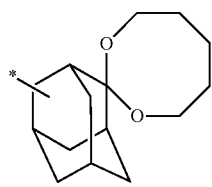

(Y32) 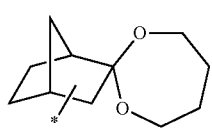

(Y33) 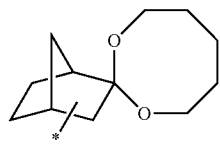

(Y34) 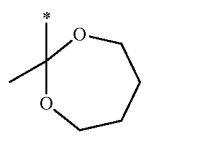

(Y35) 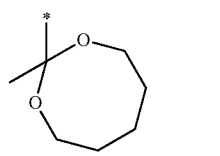

(Y36) 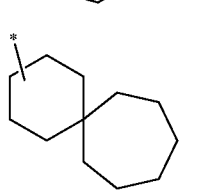

(Y37) 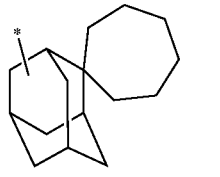

(Y38) 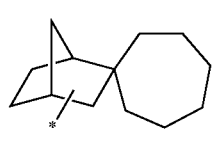

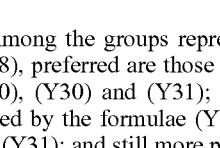

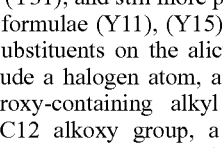

Among the groups represented by the formulae (Y1) to (Y38), preferred are those represented by formulae (Y1) to (Y20), (Y30) and (Y31); more preferred are those represented by the formulae (Y11), (Y15), (Y16), (Y19), (Y30) and (Y31); and still more preferred are those represented by the formulae (Y11), (Y15) and (Y30).

Substituents on the alicyclic hydrocarbon groups for Y include a halogen atom, a C1-C12 alkyl group, a C1-C12 hydroxy-containing alkyl group, a hydroxyl group, a C1-C12 alkoxy group, a C3-C16 alicyclic hydrocarbon group, a C6-C18 aromatic hydrocarbon group, a C7-C21 aralkyl group, a C2-C4 acyl group, a glycidyloxy group, and —(CH$_2$)$_{j2}$—O—CO—R$^{b1'}$— in which R$^{b1'}$ is a C1-C16 alkyl group and j2 is an integer of 0 to 4.

Examples of hydroxyl-containing alkyl group include a hydroxymethyl group and a hydroxyethyl group.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group. Examples of the aralkyl group include a benzyl group, phenylpropyl group, a phenethyl group, a naphthylmethyl group, or a naphthylethyl group.
Examples of the acyl group include an acetyl group, a propyonyl group and a butyryl group.
Examples of the halogen atom include a fluorine atom, a chlorine atom, a bromine atom and an iodine atom.
Examples of Y include the groups as follow.
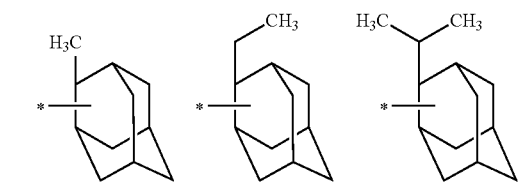
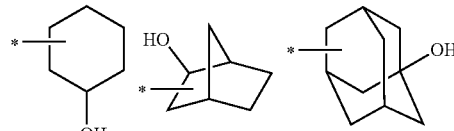
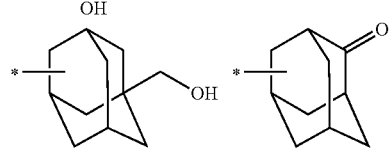
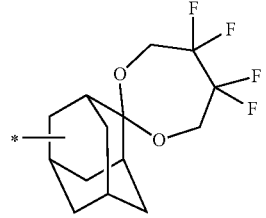
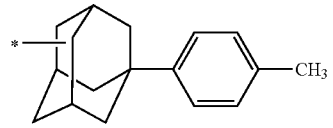
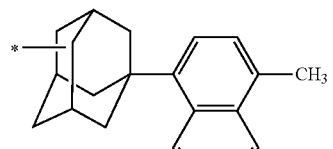
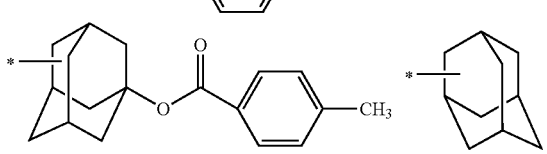
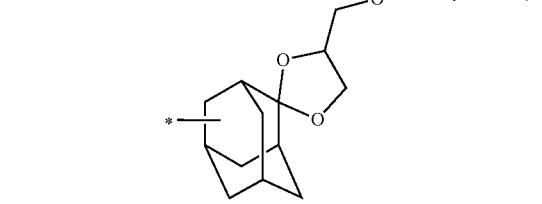
-continued
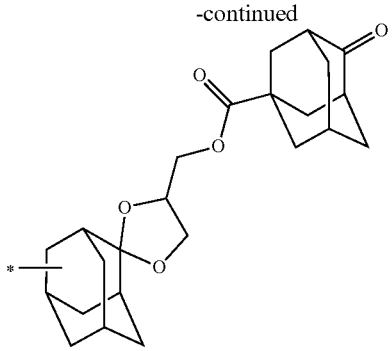
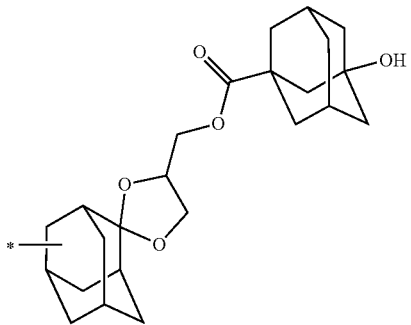
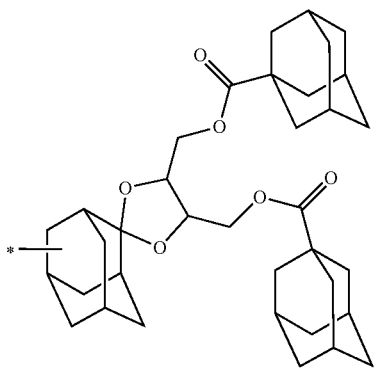
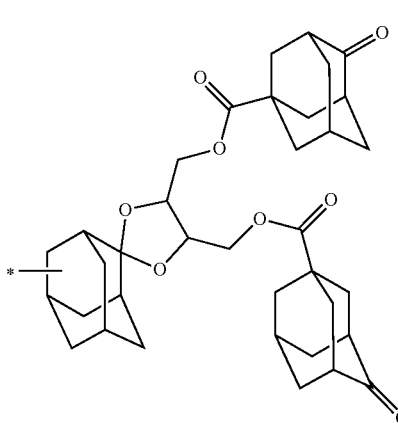

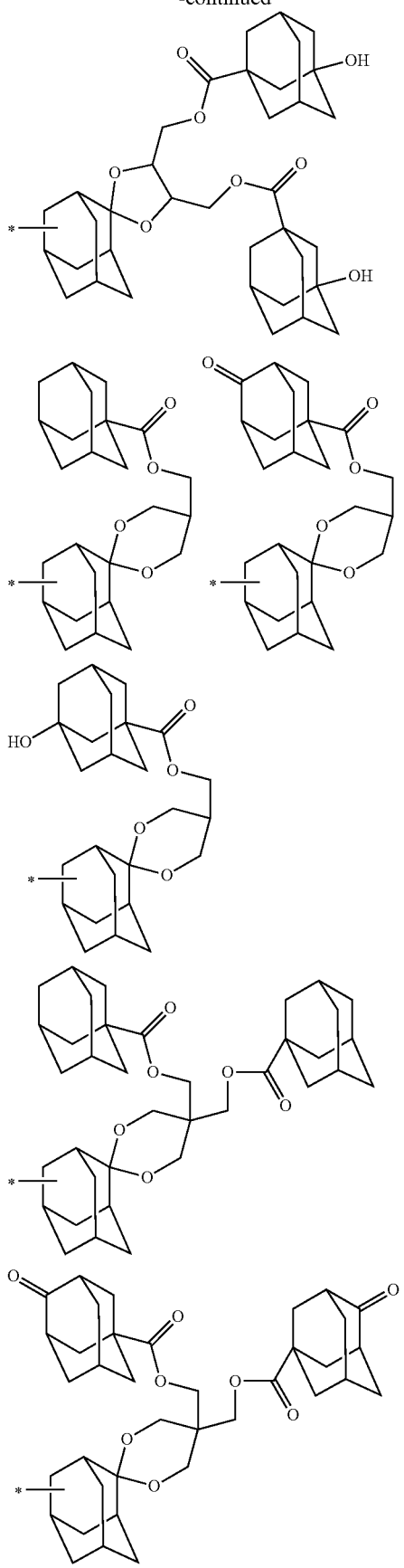
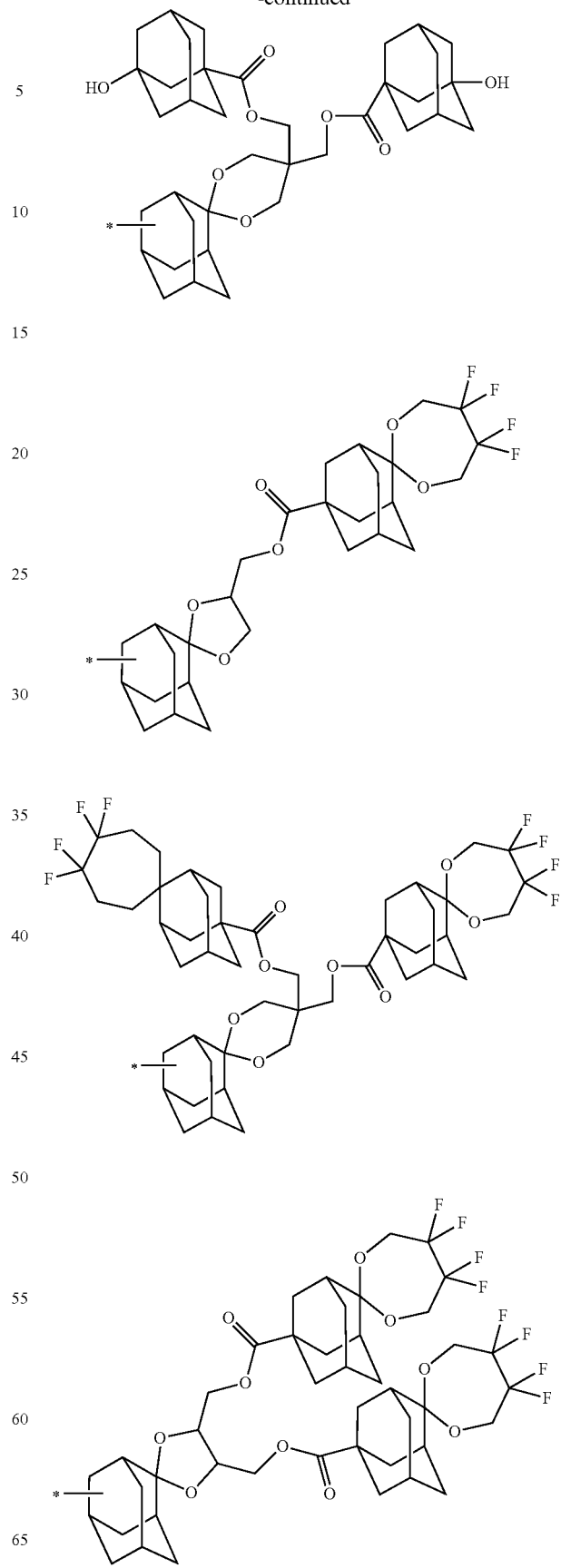

101
-continued
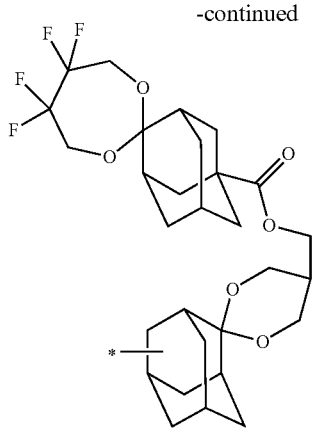
where * represents a binding position.
Y represents preferably a C3-C18 alicyclic hydrocarbon group which may have a substituent, more preferably an amadantyl group which may have a substituent, and still more preferably an amadantyl group, a hydroxyamadantyl group, an oxoamadantyl group, or the following group.
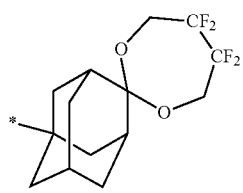
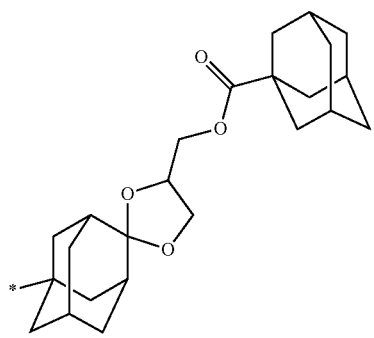
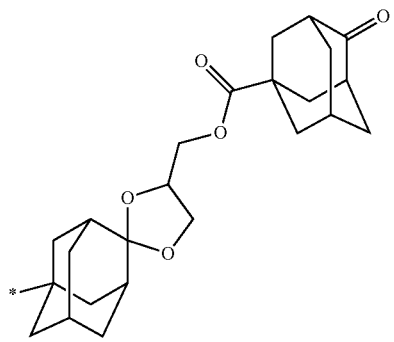
102
-continued
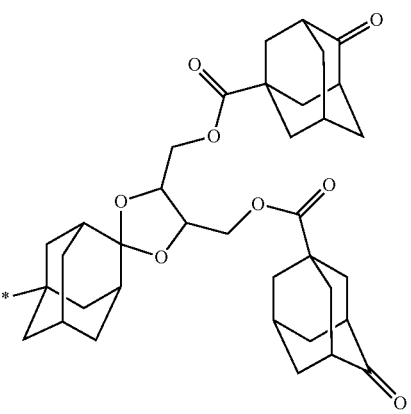
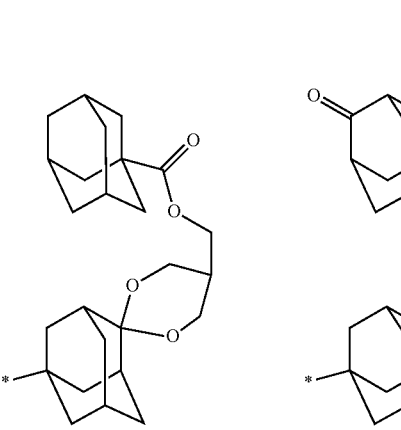
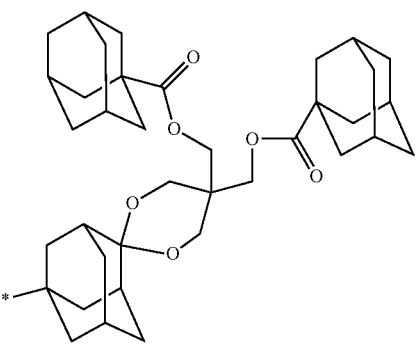

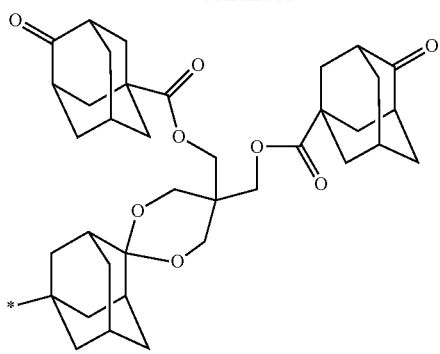
Preferred examples of the sulfonic acid anion of the salt represented by formula (B1) include salts represented by the formulae (B1-A-1) to (B1-A-55), preferably the formulae (B1-A-1) to (B1-A-4), (B1-A-9), (B1-A-10), (B1-A-24) to (B1-A-33), (B1-A-36) to (B1-A-40) and (B1-A-47) to (B1-A-55).
(B1-A-1)
(B1-A-2)
(BI-A-3)
(B1-A-4)
(B1-A-5)
(B1-A-6)
(B1-A-7)
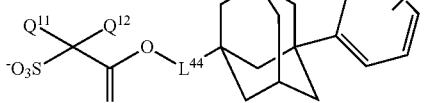
(B1-A-8)
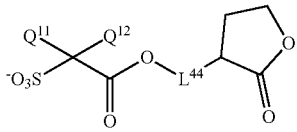
(B1-A-9)
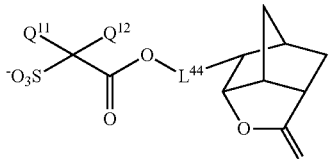
(B1-A-10)
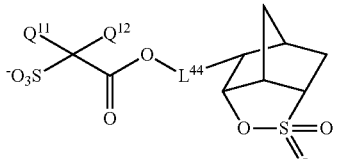
(B1-A-11)
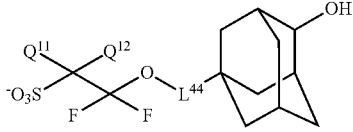
(B1-A-12)
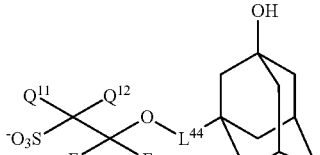
(B1-A-13)
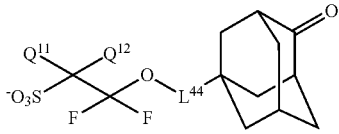
(B1-A-14)
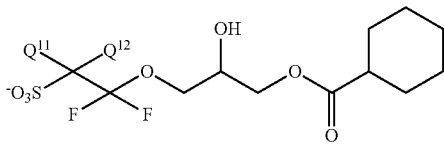
(B1-A-15)
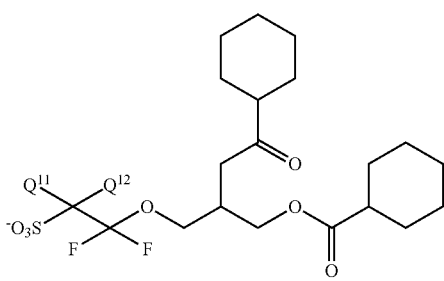

(B1-A-16)
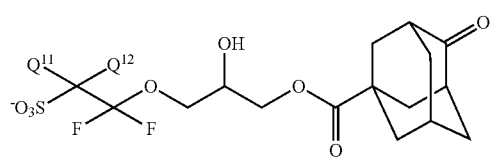
(B1-A-17)
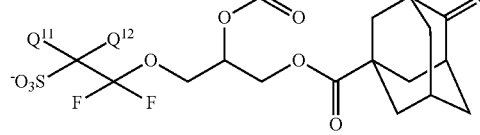
(B1-A-18)
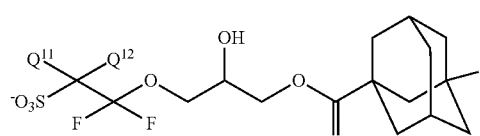
(B1-A-19)
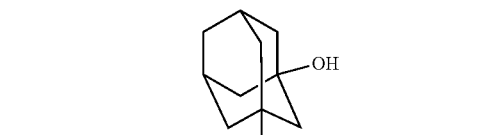
(B1-A-20)
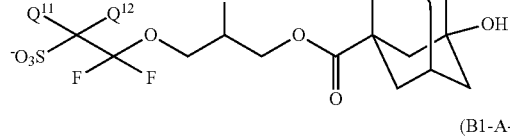
(B1-A-21)
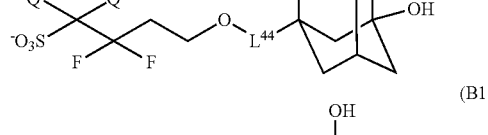
(B1-A-21)
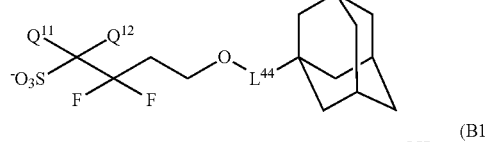
(B1-A-22)
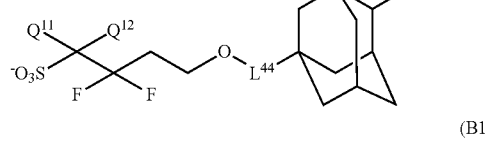
(B1-A-23)
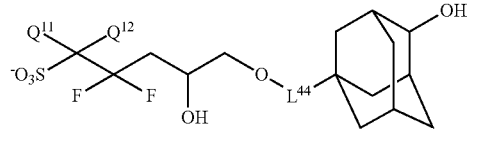
(B1-A-24)
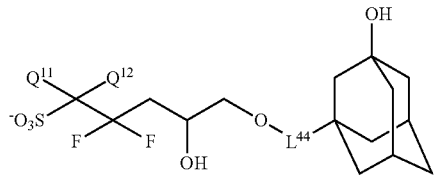
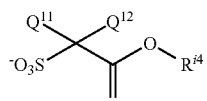
(B1-A-25)
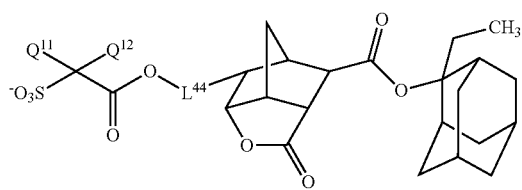
(B1-A-26)
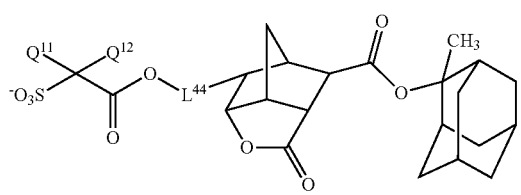
(B1-A-27)
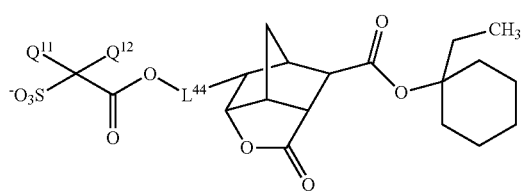
(B1-A-28)
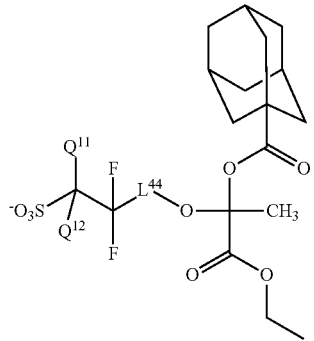

-continued
(B1-A-29)
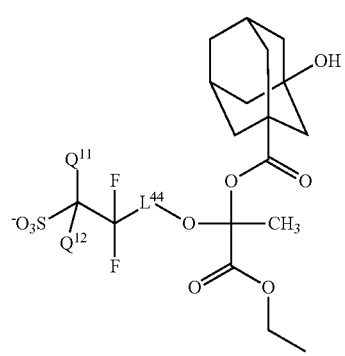
(B1-A-30)
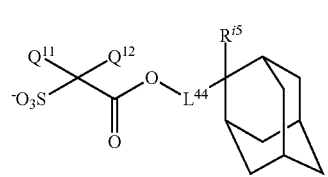
(B1-A-31)
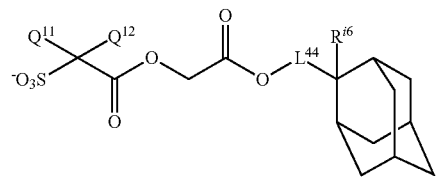
(B1-A-32)
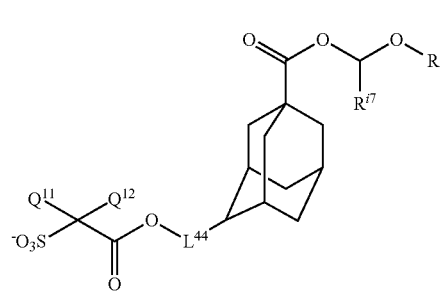
(B1-A-33)
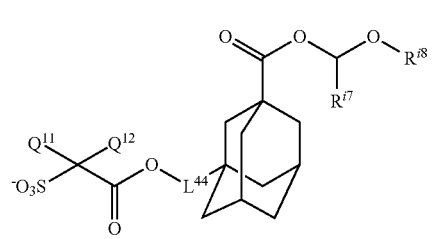
(B1-A-34)
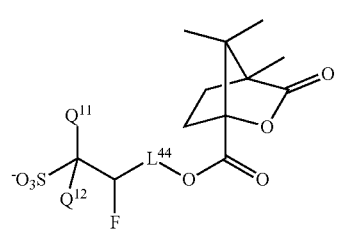
-continued
(B1-A-35)
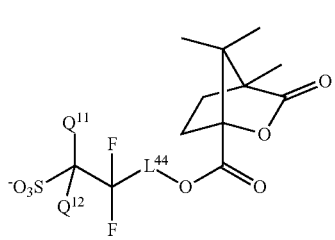
(B1-A-36)
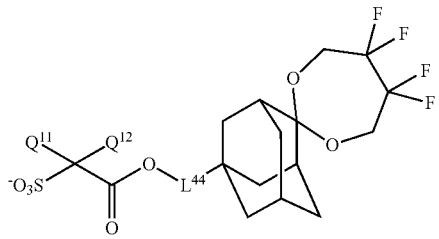
(B1-A-37)
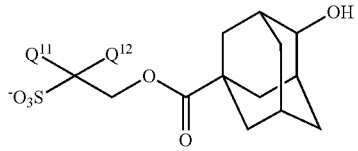
(B1-A-38)
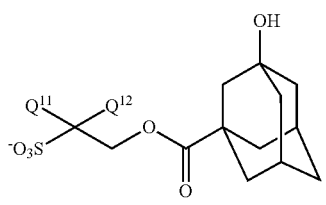
(B1-A-39)
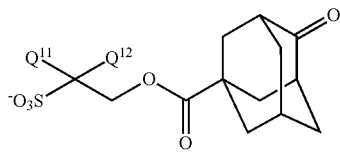
(B1-A-40)
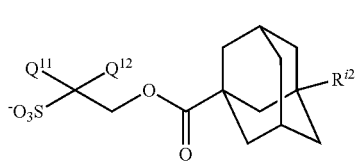
(B1-A-41)
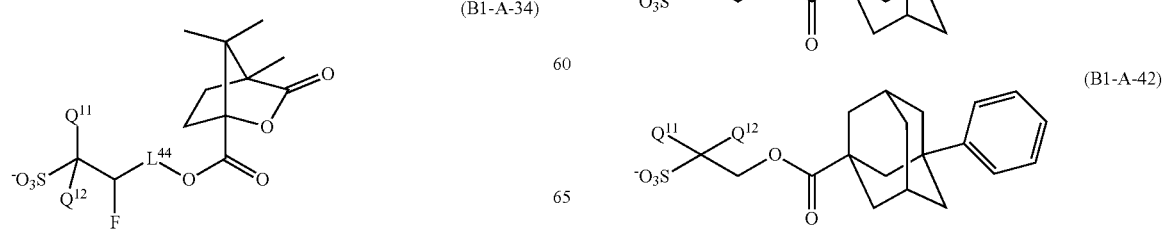
(B1-A-42)
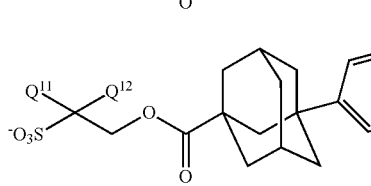

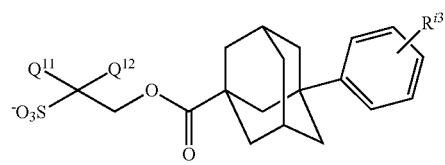
(B1-A-43)
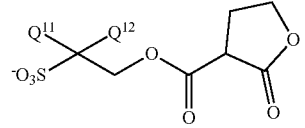
(B1-A-44)
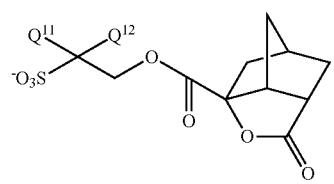
(B1-A-45)
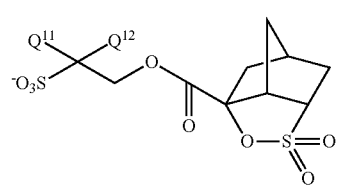
(B1-A-46)
(B1-A-47)
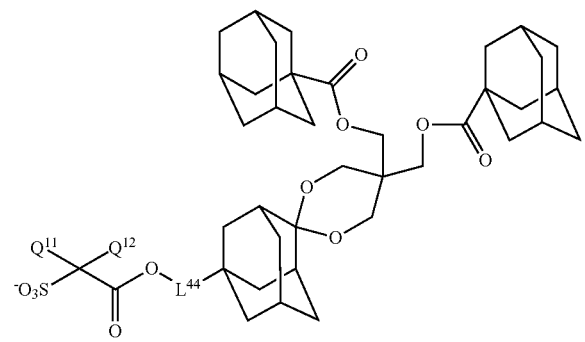
(B1-A-48)
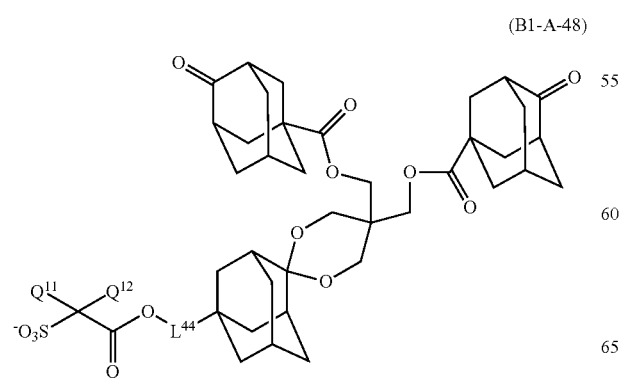
(B1-A-49)
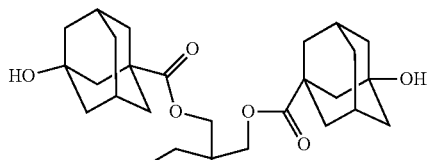
(B1-A-50)
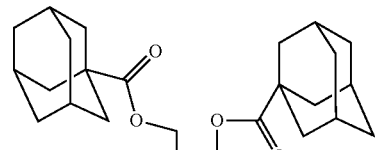
(B1-A-51)
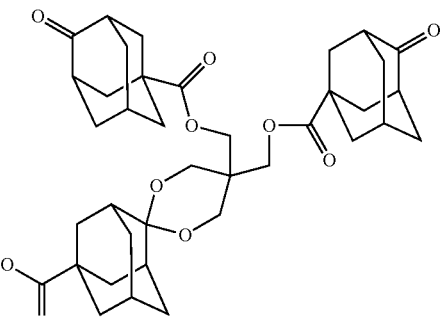
(B1-A-52)
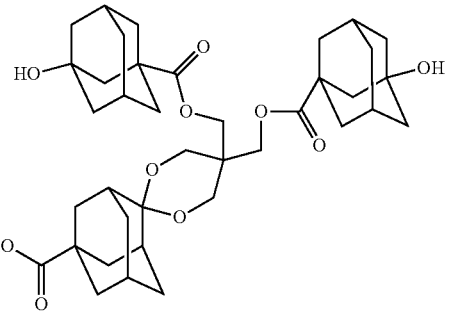

In these formulae, the symbols $Q^{11}$, $Q^{12}$ and Y are defined as above, $R^{i2}$, $R^{i3}$, $R^{i4}$, $R^{i5}$, $R^{i6}$ and $R^{i7}$ each independently represent a C1-C4 alkyl group, preferably a methyl group or an ethyl group, $R^{i8}$ represents a C1-C12 saturated hydrocarbon group [preferably a C1-C4 alkyl group], a C5-C12 monovalent alicyclic hydrocarbon group, or a combined group of them, preferably a methyl group, an ethyl group, a cyclohexyl group or an adamantyl group, and $L^{44}$ represents a single bond or a C1-C4 alkanediyl group.

Specific examples of the anion for the salt represented by formula (B1) include the following anions.

(B1a-10)
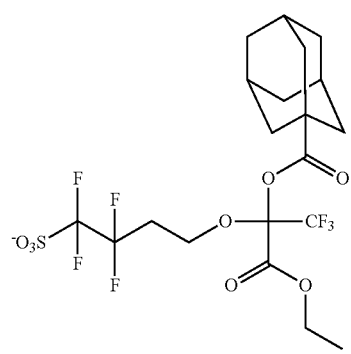
(B1a-11)
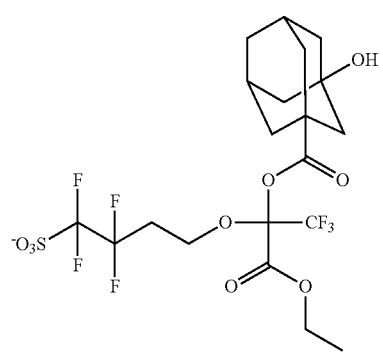
(B1a-12)
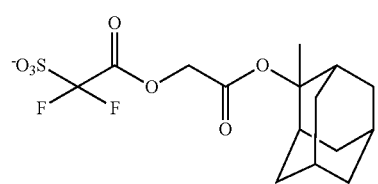
(B1a-13)
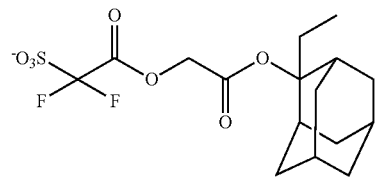
(B1a-14)
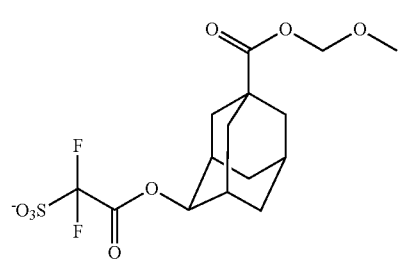
(B1a-15)
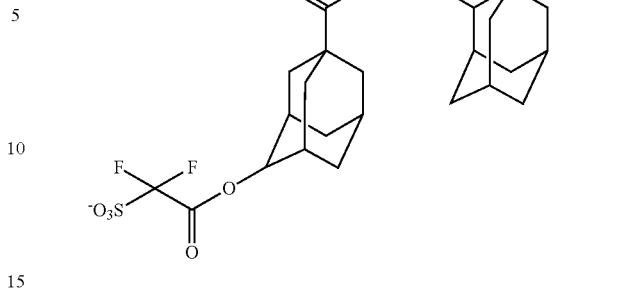
(B1a-16)
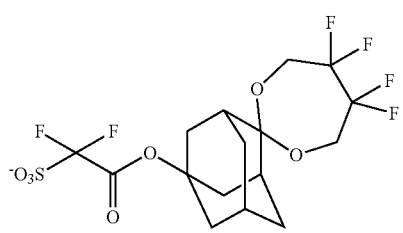
(B1a-17)
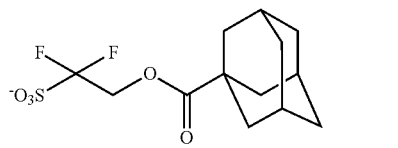
(B1a-18)
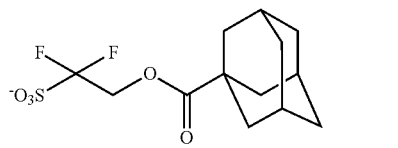
(B1a-19)
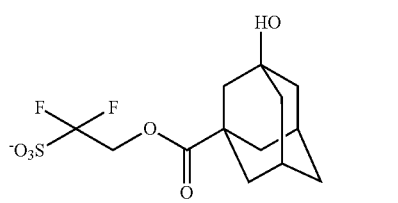
(B1a-20)
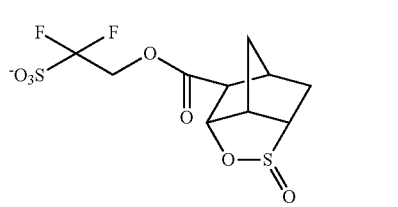
(B1a-21)
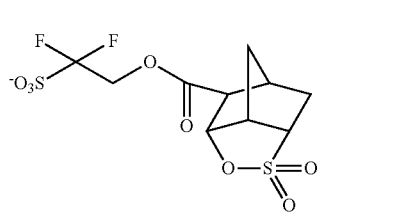

(B1a-22)
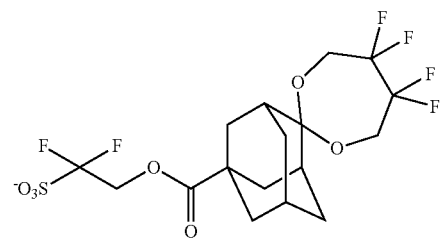
(B1a-23)
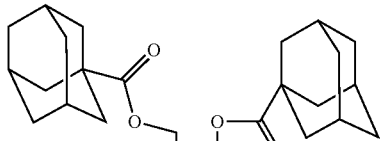
(B1a-24)
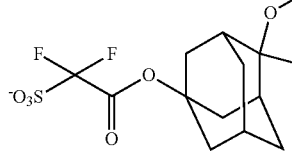
(B1a-25)
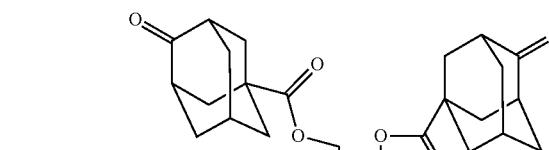
(B1a-26)
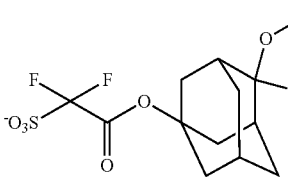
(B1a-27)
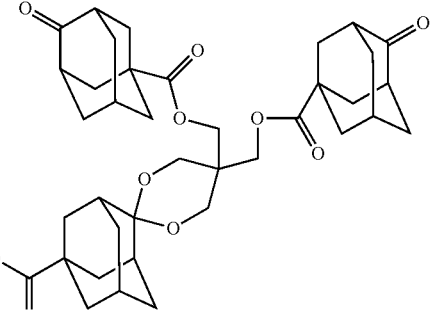
(B1a-28)
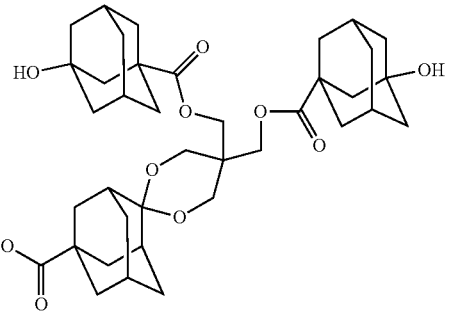
(B1a-29)
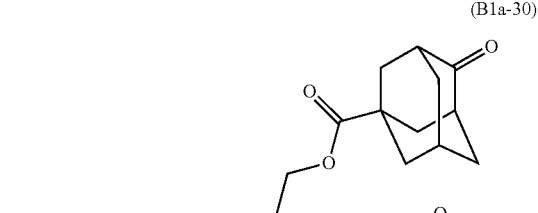
(B1a-30)
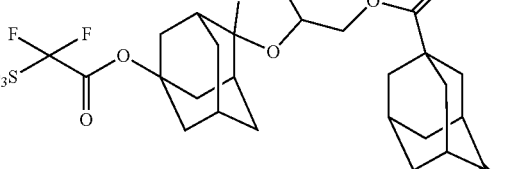

(B1a-31)
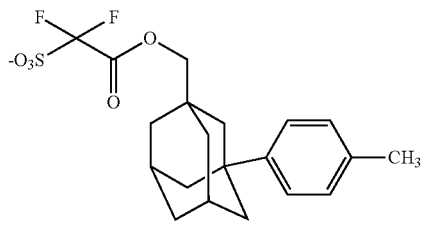

(B1a-32)
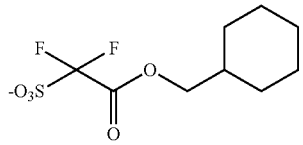

(B1a-33)
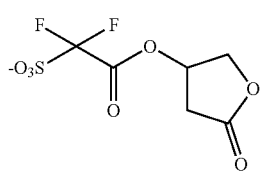

(B1a-34)
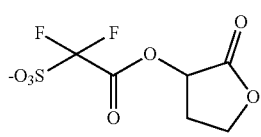

Among them, preferred are those represented by formulae (B1a-1) to (B1a-3), (B1a-7) to (B1a-16), (B1a-18), (B1a-19) and (B1a-22) to (B1a-34).

Examples of the organic counter ion represented by $Z1^+$ include an onium cations as referred to $Z^+$ of formula (I), for example those represented by the formulae (b2-1), (b2-2), (b2-3) and (b2-4), and a sulfonium cation and an iodonium cation are preferred, and a sulfonium cation, specifically an arylsulfonium cation, is more preferred.

Specific examples of the acid generator include the following salts represented by formulae (B1-1) to (B1-48). Among them, those which comprise an arylsulfonium cation are preferred, the salts represented by formulae (B1-1), (B1-2), (B1-3), (B1-5), (B1-6), (B1-7), (B1-11), (B1-12), (B1-13), (B1-14), (B1-17), (B1-20), (B1-21), (B1-22), (B1-23), (B1-24), (B1-25), (B1-26), (B1-29) and (B1-31) to (B1-48) are more preferred.

(B1-1)
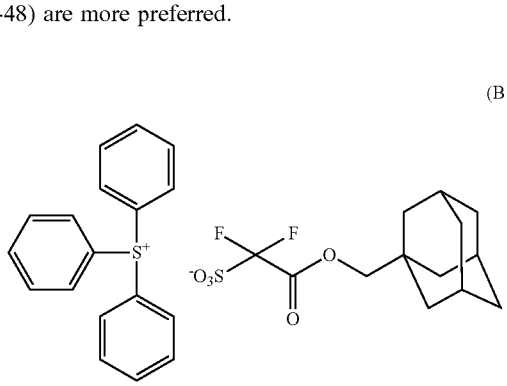

(B1-2)
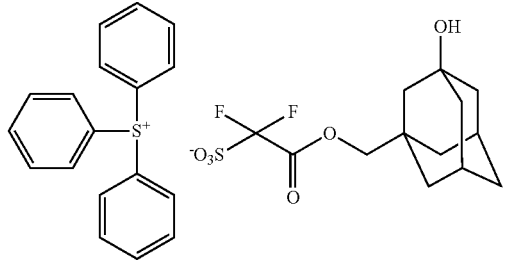

(B1-3)
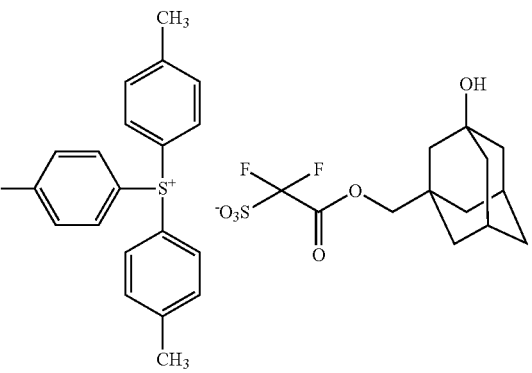

(B1-4)
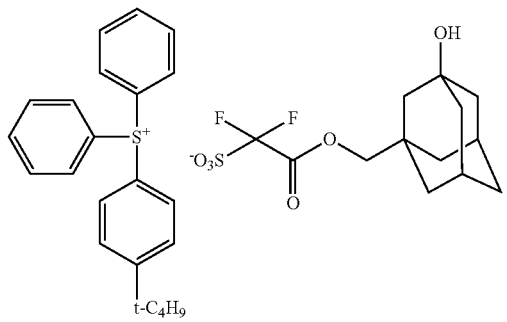

(B1-5)
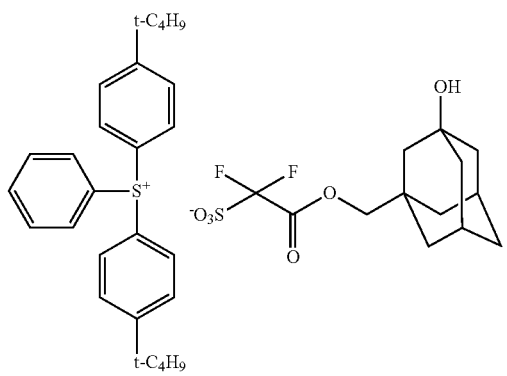

(B1-6)
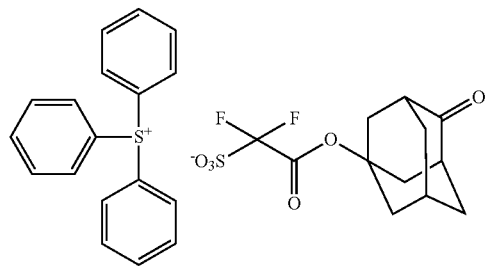
(B1-10)
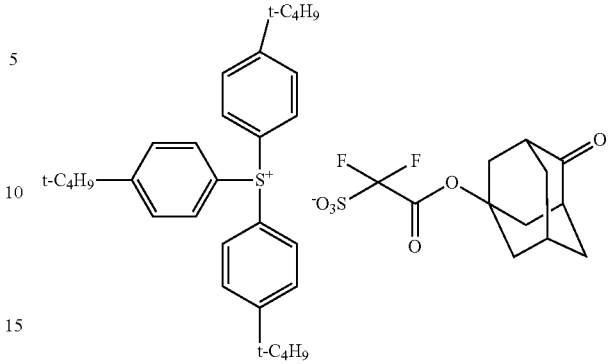
(B1-7)
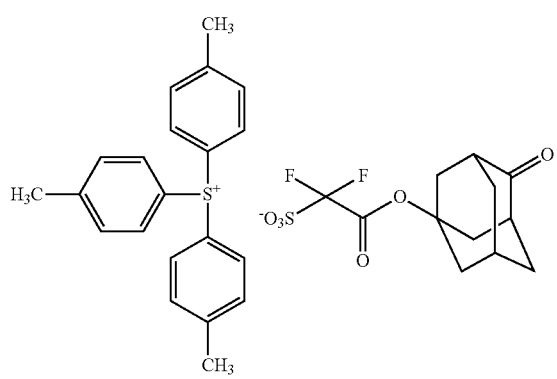
(B1-11)
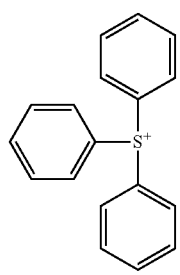
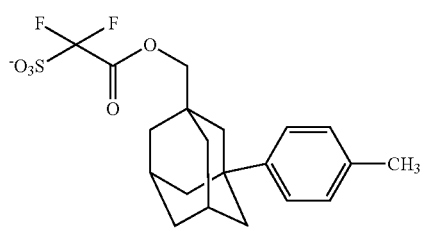
(B1-8)
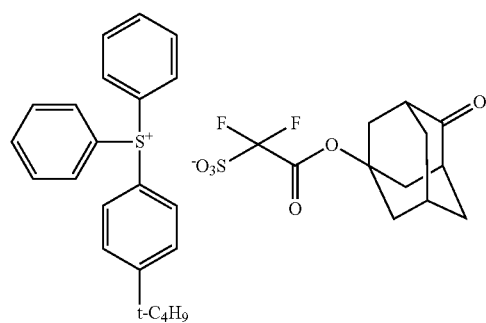
(B1-12)
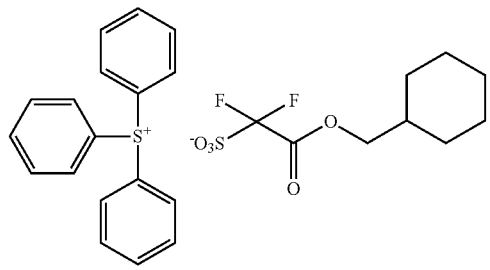
(B1-9)
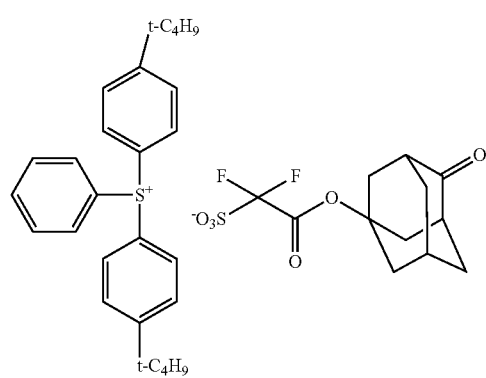
(B1-13)
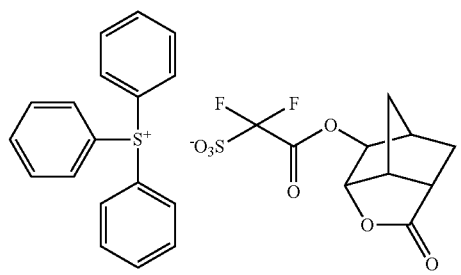

(B1-14)
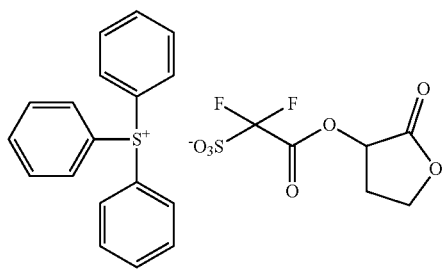
(B1-15)
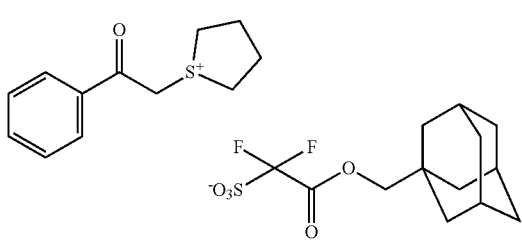
(B1-16)
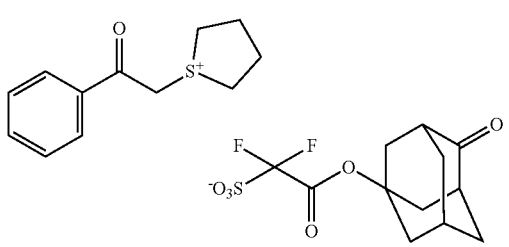
(B1-17)
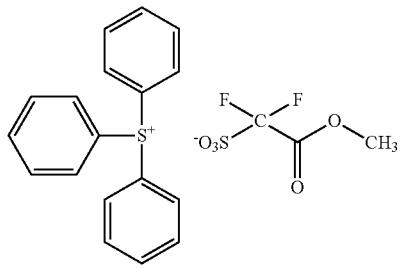
(B1-18)
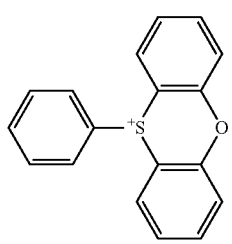
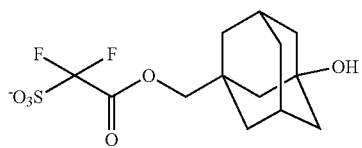
(B1-19)
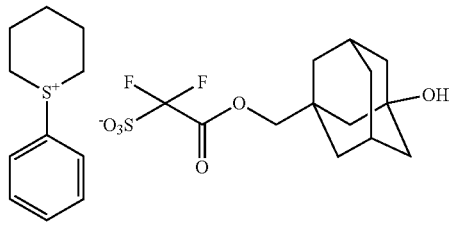
(B1-20)
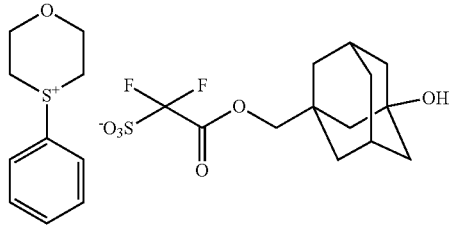
(B1-21)
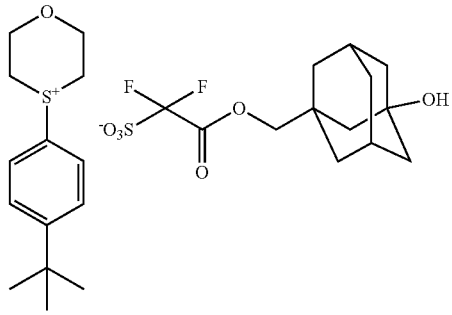
(B1-22)
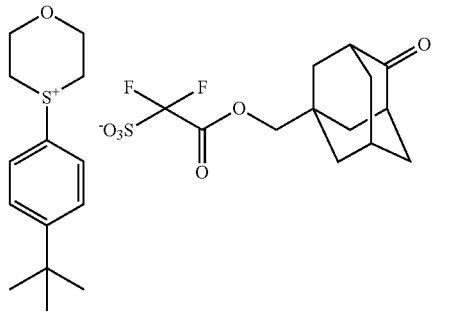
(B1-23)
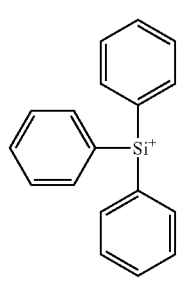

-continued
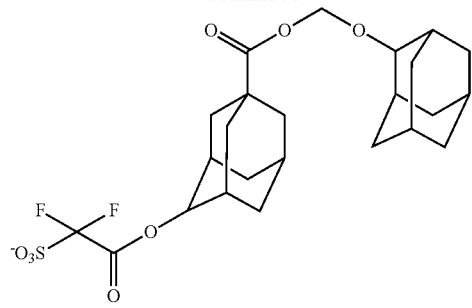
(B1-24)
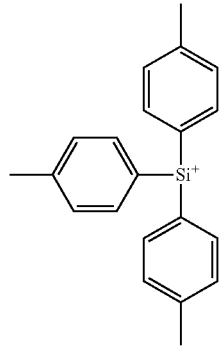
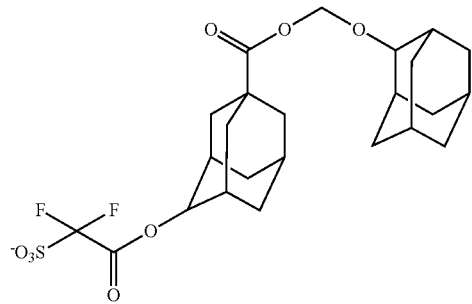
(B1-25)
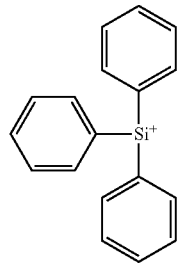
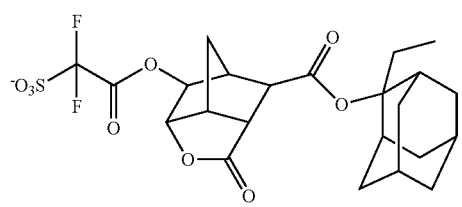
-continued
(B1-26)
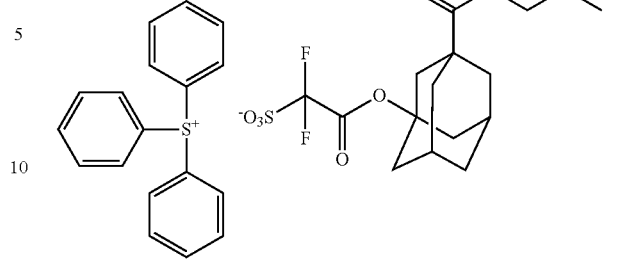
(B1-27)
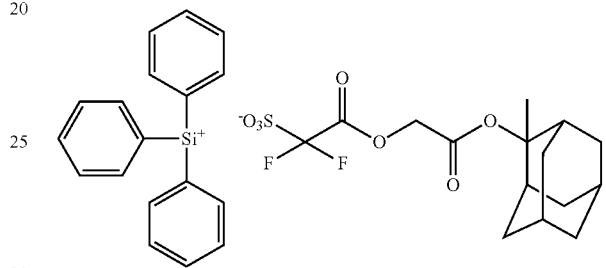
(B1-28)
(B1-29)
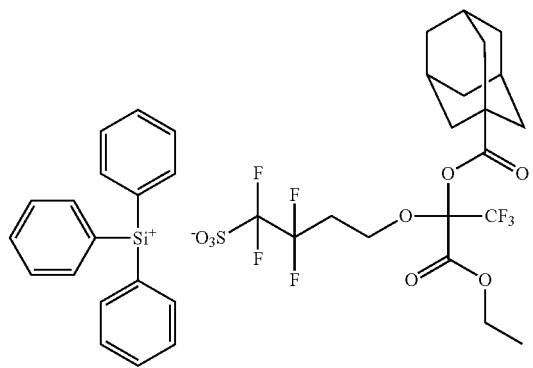

-continued
(B1-30)
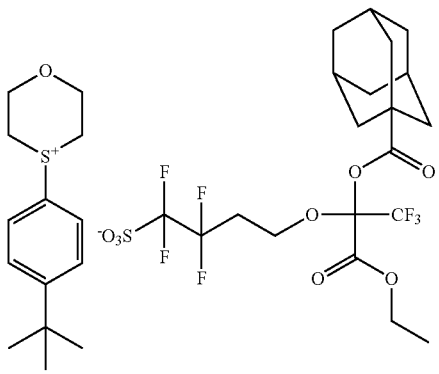
(B1-31)
(B1-33)
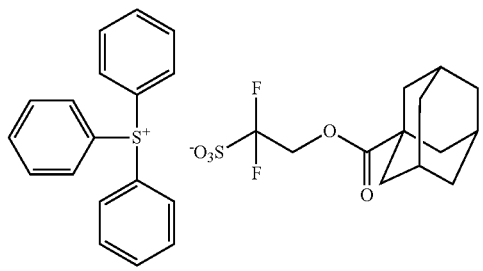
(B1-34)
(B1-32)
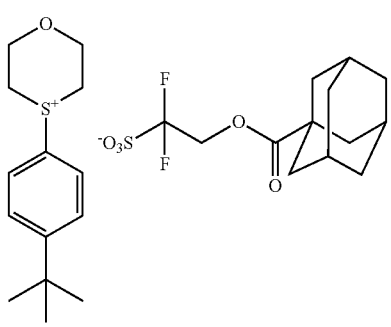
(B1-35)
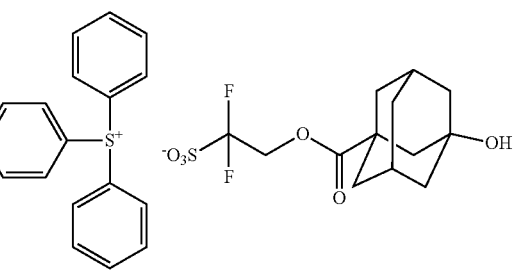
(B1-36)
(B1-37)
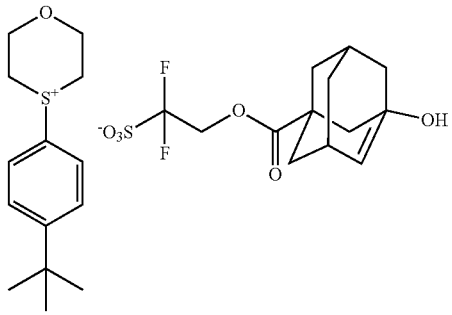
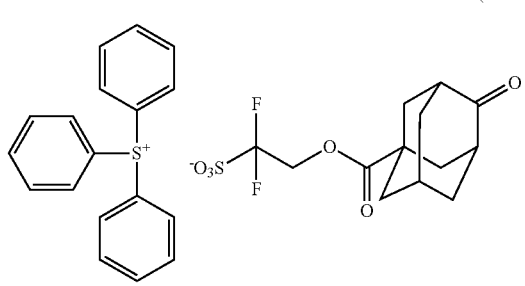

(B1-38)
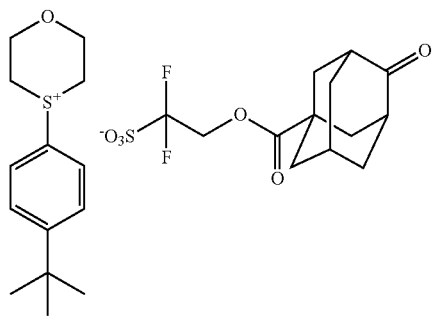
(B1-39)
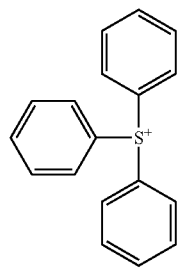
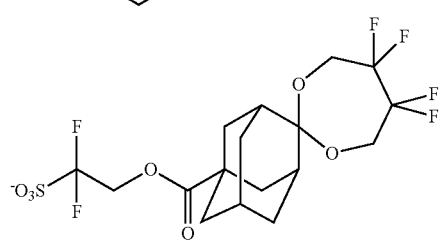
(B1-40)
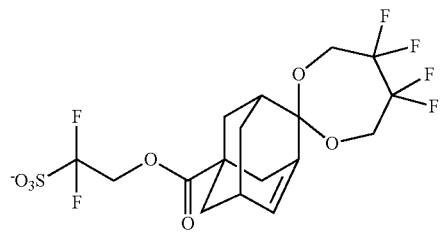
(B1-41)
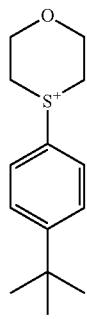
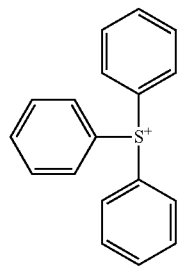
(B1-42)
(B1-43)

(B1-44)
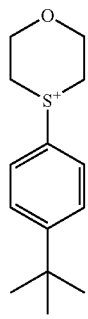
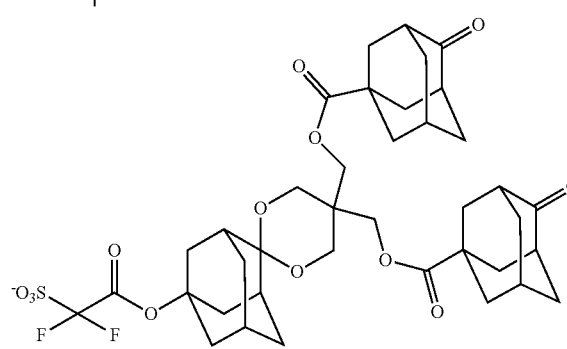
(B1-45)
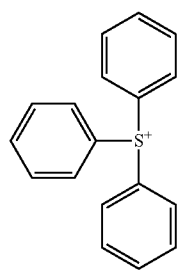
(B1-46)
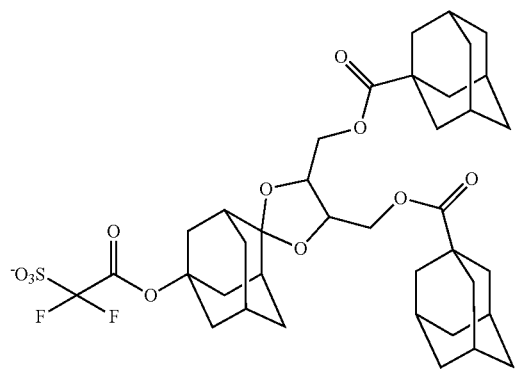
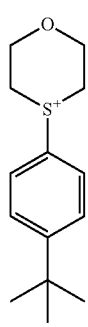
(B1-47)
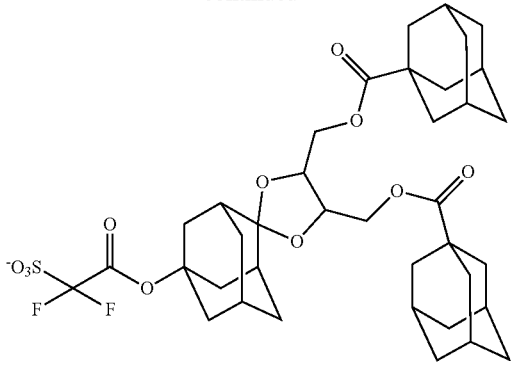
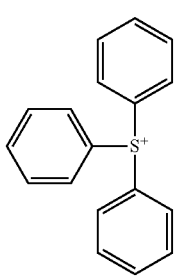
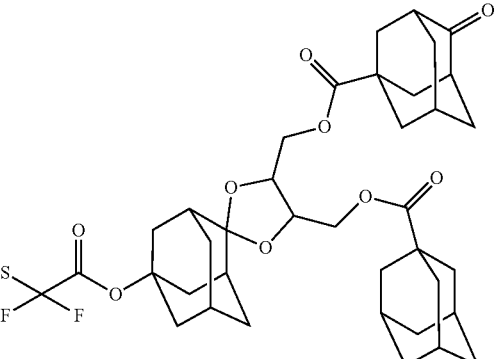
(B1-48)
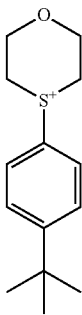

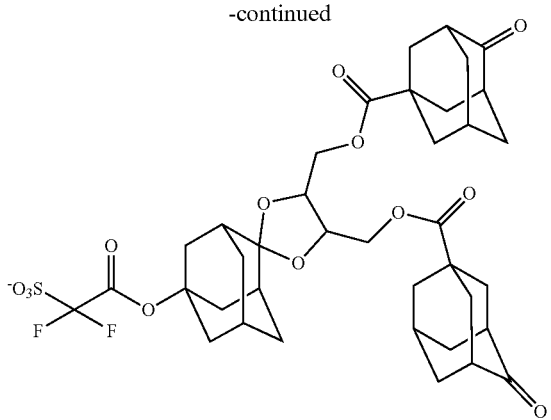

The content of the acid generator (B) is preferably 1 to 40 parts by mass, more preferably 3 to 35 parts by mass, still more preferably 30 parts by mass, further more preferably 25 parts by mass, per 100 parts of Resin (A).

When the photoresist composition further contains the acid generator (B), the total content of the acid generator (B) and the salt represented by formula (I) is preferably 1.5 to 40 parts by mass, more preferably 3 to 35 parts by mass, per 100 parts of Resin (A). When the photoresist contains the acid generator (B), the weight ratio of the salt and the acid generator (B) is usually 1:99 to 99:1, preferably 2:98 to 98:2, more preferably 5:95 to 95:5.

<Solvent>

Preferably, the photoresist composition of the disclosure further contains a solvent.

The amount of the solvent is usually 90% by weight or more, preferably 92% by weight or more preferably 94% by weight or more based on total amount of the photoresist composition of the present invention.

The amount of the solvent is usually 99.9% by weight or less and preferably 99% by weight or less based on total amount of the photoresist composition of the present invention. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

<Quencher>

The photoresist composition of the disclosure may further contain a quencher such as a basic compound. The "quencher" has the property that it can trap an acid, especially an acid generated from the acid generator by exposure to light for lithography.

Examples of the quencher include a basic compound, such as a basic nitrogen-containing organic compound, and a salt which generates an acid having acidity weaker than an acid generated from the acid generators.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris [2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy) ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

As to salt which generates an acid having acidity weaker than an acid generated from the acid generators, the acidity in the salts is shown by the acid dissociation constant (pKa).

The acid dissociation constant of acid generated from the salt for a quencher is usually −3<pKa.

The salt for a quencher is preferably a salt of −1<pKa<7, and more preferably a salt of 0<pKa<5.

Specific examples of the salt for a quencher include the following ones, an onium carboxylic acid salt such as the salt of formula (D), and salts recited in US2012/328986A1, US2011/171576A1, US2011/201823A1, JP2011-39502A1, and US2011/200935A1.

The photoresist composition comprises preferably onium carboxylic acid salt, more preferably the salt of formula (D).

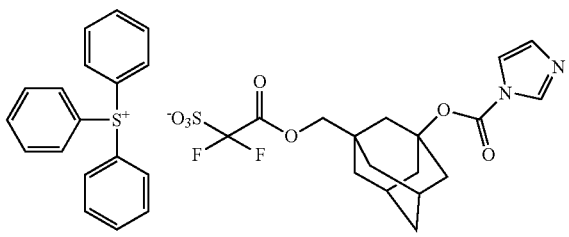

133
-continued
134
-continued
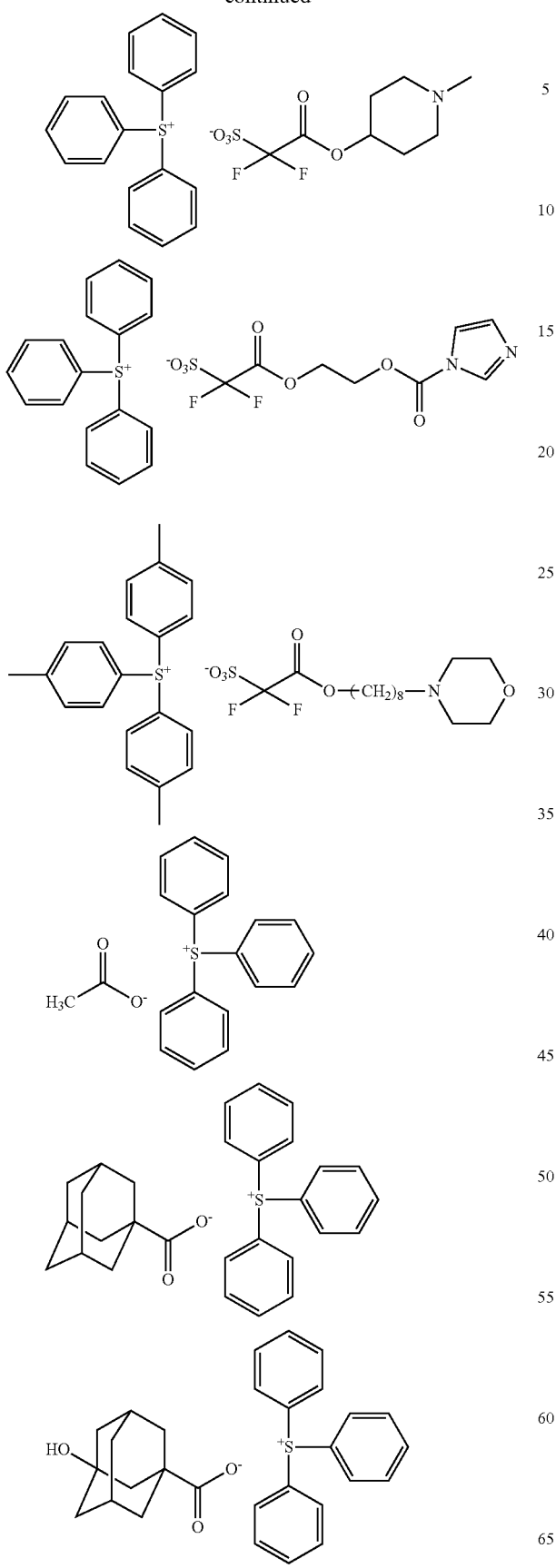
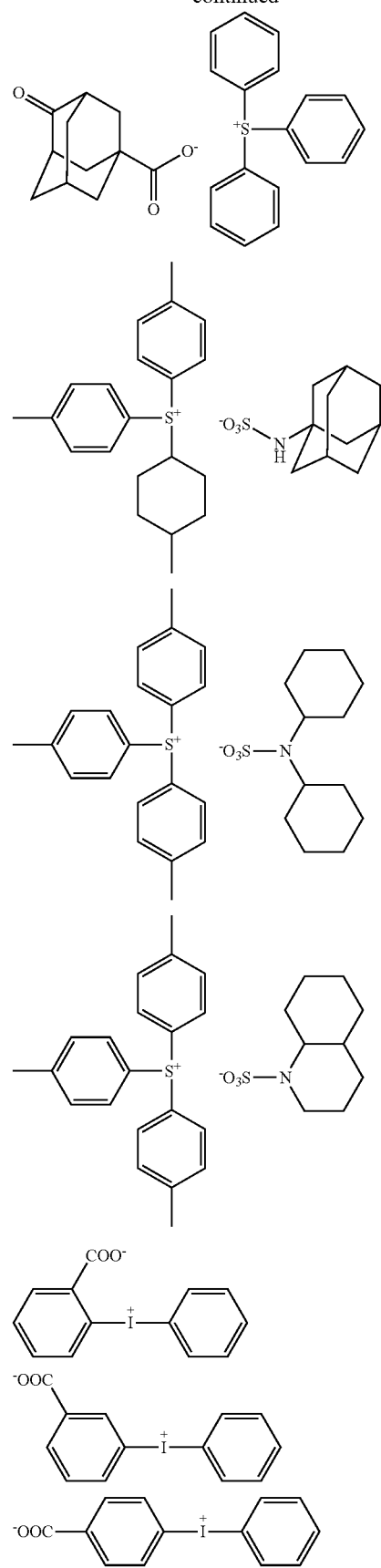

-continued

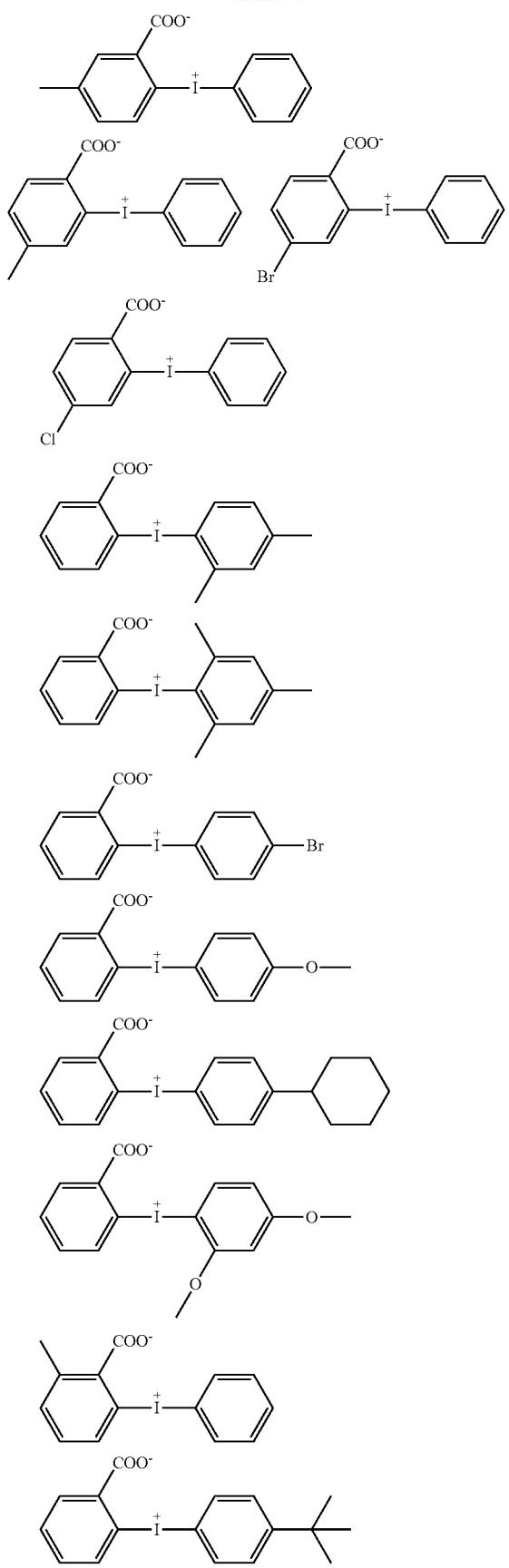

-continued

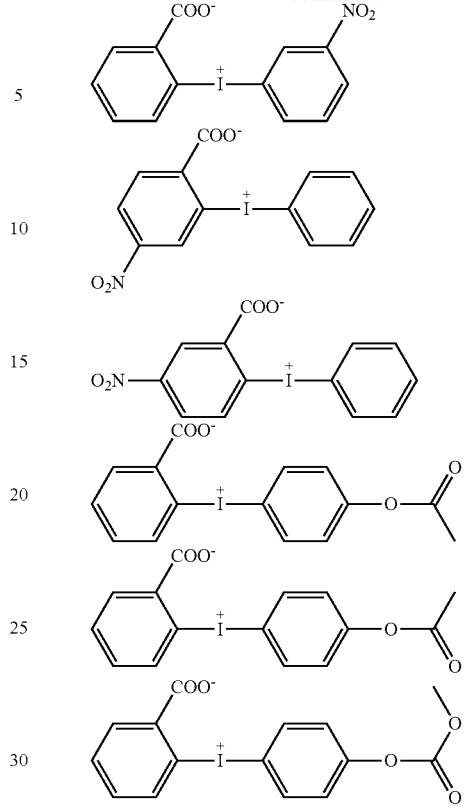

The content of quencher is preferably 0.01 to 5% by mass, more preferably 0.01 to 4% by mass, still more preferably 0.01 to 3% by mass, based on sum of solid component.

The photoresist compositions of the present invention may comprise, if necessary, a small amount of various additives such as a sensitizer, a dissolution inhibitor, other polymers, a surfactant, a stabilizer and a dye as long as the effect of the present invention is not prevented.

The photoresist compositions of the present invention can be prepared by mixing, usually in a solvent, an acid generator which contains the salt represented by formula (I) and Resin (A), and if necessary a quencher, and/or additives at a suitable ratio for the composition, optionally followed by filtrating the mixture with a filter having 0.003 µm to 0.2 µm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

A photoresist pattern can be produced by the following steps (1) to (5):

(1) a step of applying the photoresist composition of the present invention on a substrate, (2) a step of forming a composition film by conducting drying, (3) a step of exposing the composition film to radiation, (4) a step of baking the exposed composition film, and (5) a step of developing the baked composition film with an alkaline developer.

The applying of the photoresist composition on a substrate is usually conducted using a conventional apparatus such as spin coater. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0 \times 10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), a light source radiating harmonic laser light in a far UV region or a vacuum UV region by wavelength conversion of laser light from a solid laser light source (such as YAG or semiconductor laser), and a light source radiating electron beam or EUV (extreme ultraviolet) light.

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the present invention, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the present invention, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 90% to 100% by weight, more preferably from 95% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the present invention is suitable for KrF excimer laser lithography, ArF excimer laser lithography, EUV (extreme ultraviolet) lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography under the following conditions.

Column: HLC-8120GPC Type (Three Columns with guard column), TSKgel Multipore HXL-M, manufactured by TOSOH CORPORATION Solvent: Tetrahydrofuran, Flow rate: 1.0 mL/min.
Detector: RI detector
Column temperature: 40° C.
Injection volume: 100 μL
Standard reference material: Standard polystyrene Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). Hereinafter the peak value in the molecular ion spectrum determined by the spectrometry is referred to as "MASS".

Example 1

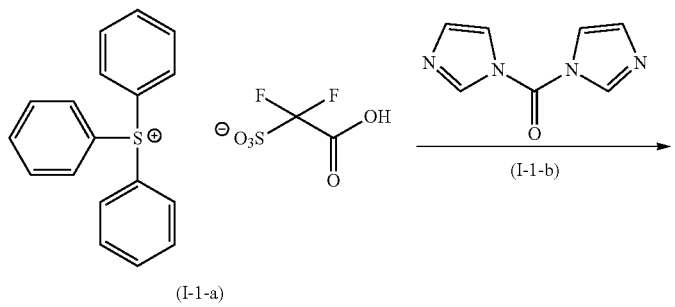

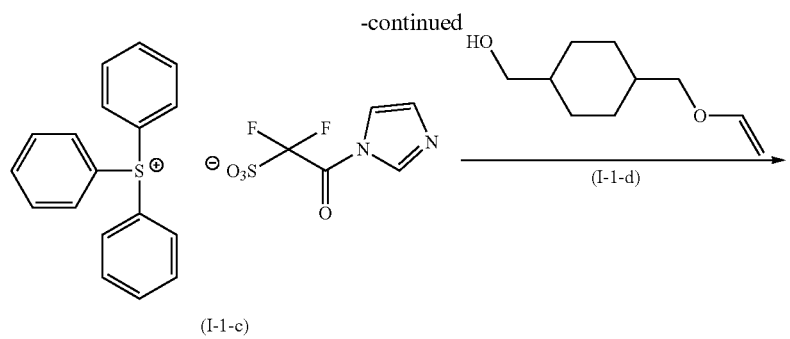

In a reactor, 50.3 parts of the salt represented by the formula (I-1-a) and 250 parts of acetonitrile were mixed and stirred at 40° C. for one hour. To resultant mixture, 23.8 parts of the salt represented by the formula (I-1-b) was added over 10 minutes, and then its temperature was increased to 70° C. Then the obtained mixture was stirred at 70° C. for 2 hours to obtain a solution which contained a salt represented by formula (I-1-c).

The solution was cooled to 23° C., and thereto was added a mixture of 13 parts of a salt represented by formula (I-1-d) and 13 parts of acetonitrile over 90 minutes, and stirred at 23° C. for one hour, followed by being concentrated. To the concentrates, 500 parts of chloroform and 390 parts of 5% aqueous oxalic acid solution were added, followed by being stirred at 23° C. for 30 minutes. The obtained mixture was left so as to separate an organic layer.

To the organic layer, 250 parts of ion-exchanged water were added and stirred at 23° C. for 30 minutes for washing, followed by separating an organic layer: The organic layer was washed four times with ion-exchanged water in this manner.

Then the resultant mixture was concentrated. To the obtained residue, 170 parts of tert-butylmethylether was added and the resultant mixture was stirred, and then its supernatant was removed therefrom.

The obtained residue was dissolved in acetonitrile and then concentrated to obtain 40.3 parts of the salt represented by formula (I-1).

MS (ESI(+) Spectrum): M$^+$ 263.1
MS (ESI(−) Spectrum): M$^-$ 327.1

Examples 2

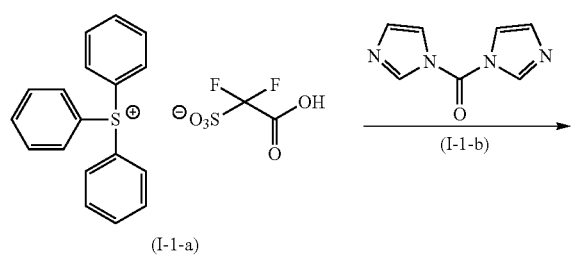

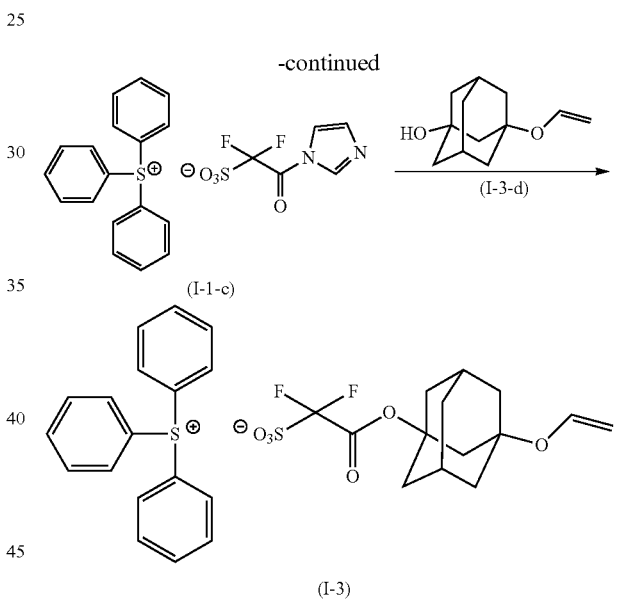

In a reactor, 5 parts of the salt represented by the formula (I-1-a) and 25 parts of acetonitrile were mixed and stirred at 40° C. for one hour. To resultant mixture, 2.38 parts of the salt represented by the formula (I-1-b) was added at 40° C., and then its temperature was increased to 60° C. Then the obtained mixture was stirred at 60° C. for 2 hours to obtain a solution which contained a salt represented by formula (I-1-c).

To the solution was added a mixture of 1.48 parts of a salt represented by formula (I-3-d) and 1.48 parts of acetonitrile, and stirred at 60° C. for 6 hours, followed by being concentrated. To the concentrates, 50 parts of chloroform and 40 parts of 5% aqueous oxalic acid solution were added, followed by being stirred at 23° C. for 30 minutes. The obtained mixture was left so as to separate an organic layer.

To the organic layer, 25 parts of ion-exchanged water were added and stirred at 23° C. for 30 minutes for washing, followed by separating an organic layer: The organic layer was washed five times with ion-exchanged water in this manner.

Then the resultant mixture was concentrated. To the obtained residue, 20 parts of tert-butylmethylether was added and the resultant mixture was stirred, and then its supernatant was removed therefrom. The obtained residue was dissolved in acetonitrile and then concentrated to obtain 4.48 parts of the salt represented by formula (I-3).

MS (ESI(+) Spectrum): M+ 263.1
MS (ESI(−) Spectrum): M− 351.1

Example 3

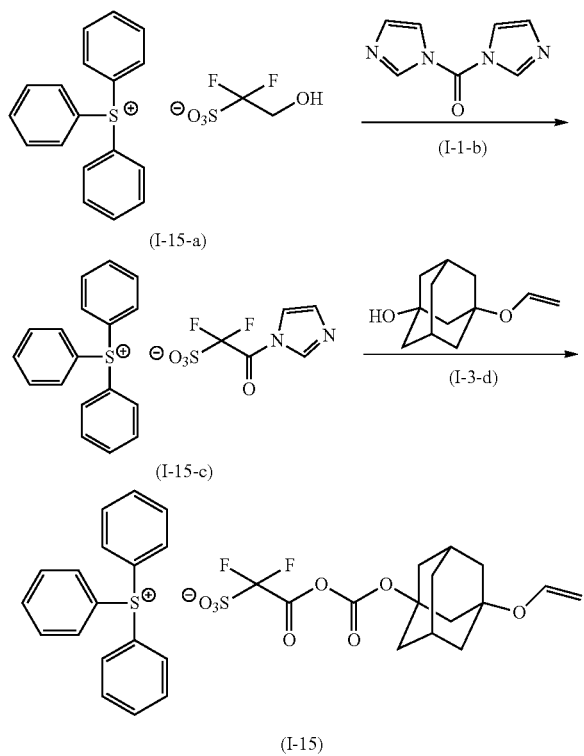

In a reactor, 4.84 parts of the salt represented by the formula (I-15-a) and 25 parts of acetonitrile were mixed and stirred at 40° C. for one hour. To resultant mixture, 2.38 parts of the salt represented by the formula (I-1-b) was added at 40° C., and then its temperature was increased to 60° C. Then the obtained mixture was stirred at 60° C. for 2 hours to obtain a solution which contained a salt represented by formula (I-15-c).

To the solution was added a mixture of 1.48 parts of a salt represented by formula (I-3-d) and 1.48 parts of acetonitrile, and stirred at 60° C. for 6 hours, followed by being concentrated. To the concentrates, 50 parts of chloroform and 40 parts of 5% aqueous oxalic acid solution were added, followed by being stirred at 23° C. for 30 minutes. The obtained mixture was left so as to separate an organic layer.

To the organic layer, 25 parts of ion-exchanged water were added and stirred at 23° C. for 30 minutes for washing, followed by separating an organic layer. The organic layer was washed five times with ion-exchanged water in this manner.

Then the resultant mixture was concentrated. To the obtained residue, 20 parts of tert-butylmethylether was added and the resultant mixture was stirred, and then its supernatant was removed therefrom.

The obtained residue was dissolved in acetonitrile and then concentrated to obtain 4.12 parts of the salt represented by formula (I-15).

MS (ESI(+) Spectrum): M+ 263.1
MS (ESI(−) Spectrum): M− 381.1

Example 4

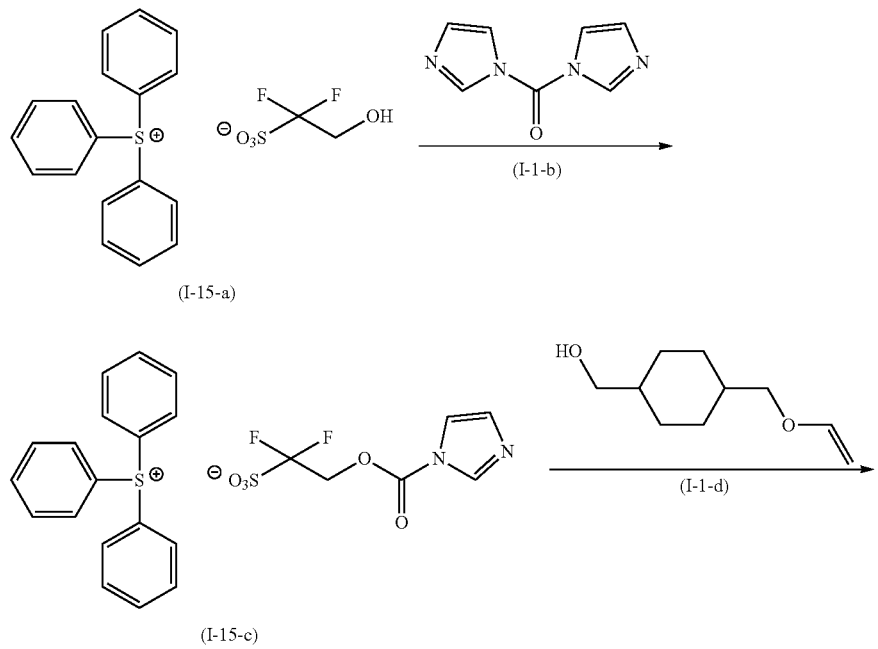

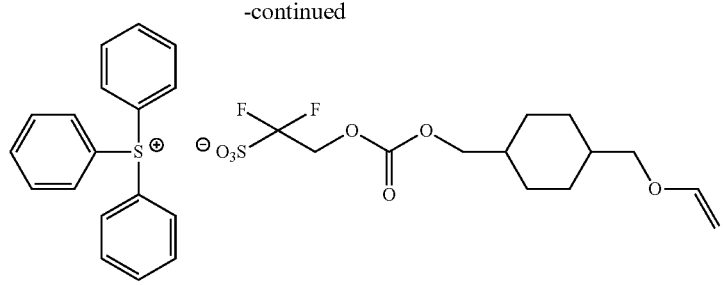

(I-16)

In a reactor, 4.84 parts of the salt represented by the formula (I-15-a) and 25 parts of acetonitrile were mixed and stirred at 40° C. for one hour. To resultant mixture, 2.38 parts of the salt represented by the formula (I-1-b) was added at 40° C., and then its temperature was increased to 60° C. Then the obtained mixture was stirred at 60° C. for 2 hours to obtain a solution which contained a salt represented by formula (I-15-c).

To the solution was added a mixture of 1.3 parts of a salt represented by formula (I-1-d) and 1.3 parts of acetonitrile, and stirred at 60° C. for 6 hours, followed by being concentrated. To the concentrates, 50 parts of chloroform and 40 parts of 5% aqueous oxalic acid solution were added, followed by being stirred at 23° C. for 30 minutes. The obtained mixture was left so as to separate an organic layer.

To the organic layer, 25 parts of ion-exchanged water were added and stirred at 23° C. for 30 minutes for washing, followed by separating an organic layer: The organic layer was washed five times with ion-exchanged water in this manner.

Then the resultant mixture was concentrated. To the obtained residue, 20 parts of tert-butylmethylether was added and the resultant mixture was stirred, and then its supernatant was removed therefrom.

The obtained residue was dissolved in acetonitrile and then concentrated to obtain 4.26 parts of the salt represented by formula (I-16).

MS (ESI(+) Spectrum): M$^+$ 263.1
MS (ESI(−) Spectrum): M$^-$ 357.1

Synthesis of Resin

Monomers used in the following Example are following ones.

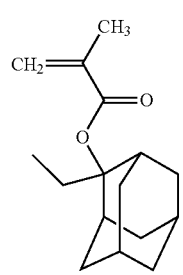

(a1-1-2)

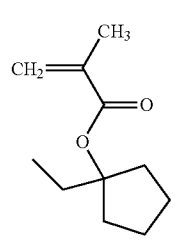

(a1-2-9)

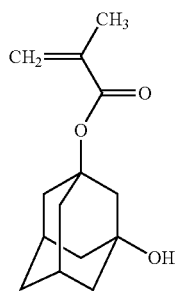

(a2-1-1)

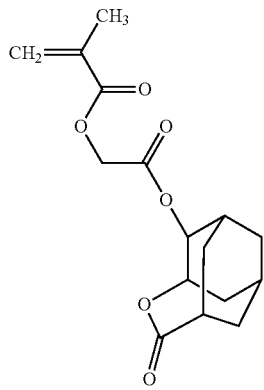

(a3-4-2)

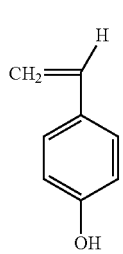

(a2-0-2)

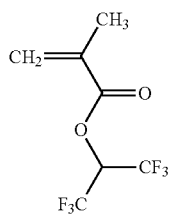

(a4-0-12)

-continued (a5-1-1)

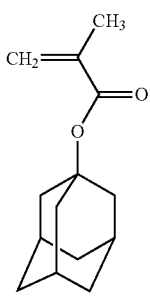

Those monomers are sometimes referred to as "Monomer (X)" in which (X) represents the sign of the formula corresponding to the monomer.

For example, the monomer represented by formula (a1-1-2) is referred to as "Monomer (a1-1-2)".

Resin Synthesis Example 1

The monomers (a1-1-2), (a1-2-9), (a2-1-1) and (a3-4-2) were mixed in a molar ratio of 35/24/2.5/38.5 (monomer (a1-1-2)/monomer (a1-2-9)/monomer (a2-1-1)/monomer (a3-4-2)), and propyleneglycolmonomethyletheracetate was added in 1.5 times parts based on total parts of all monomers to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation, followed by being filtrated. The collected precipitate was dissolved in propyleneglycolmonomethyletheracetate, and then a large amount of the mixture of methanol and water was added thereto to cause precipitation, followed by being filtrated: This reprecipitation step was conducted twice. As a result, a polymer having a weight-average molecular weight of about 8,600 was obtained in a yield of 78%. The polymer had the following structural units.

That resin is referred to as polymer A1.

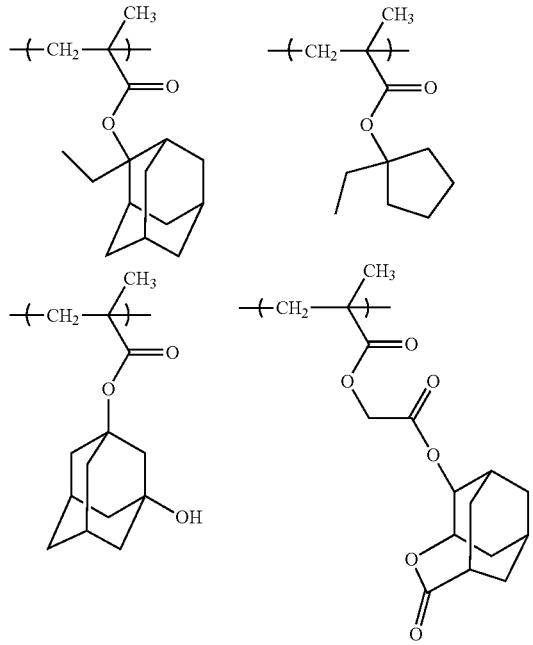

Resin Synthesis Example 2

The monomers (a1-1-2), (a1-2-9), (a2-1-1), (a2-0-2) and (a3-4-2) were mixed in a molar ratio of 35/24/2.5/5/33.5 (monomer (a1-1-2)/monomer (a1-2-9)/monomer (a2-1-1)/monomer (a2-0-2)/monomer (a3-4-2)), and propyleneglycolmonomethyletheracetate was added in 1.5 times parts based on total parts of all monomers to prepare a mixture. To the mixture, azobisisobutyronitrile as an initiator in a ratio of 1 mol % based on all monomer molar amount and azobis (2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation, followed by being filtrated. The collected precipitate was dissolved in propyleneglycolmonomethyletheracetate, and then a large amount of the mixture of methanol and water was added thereto to cause precipitation, followed by being filtrated: This reprecipitation step was conducted twice. As a result, a polymer having a weight-average molecular weight of about 8,900 was obtained in a yield of 82%. The polymer had the following structural units.

That resin is referred to as polymer A2.

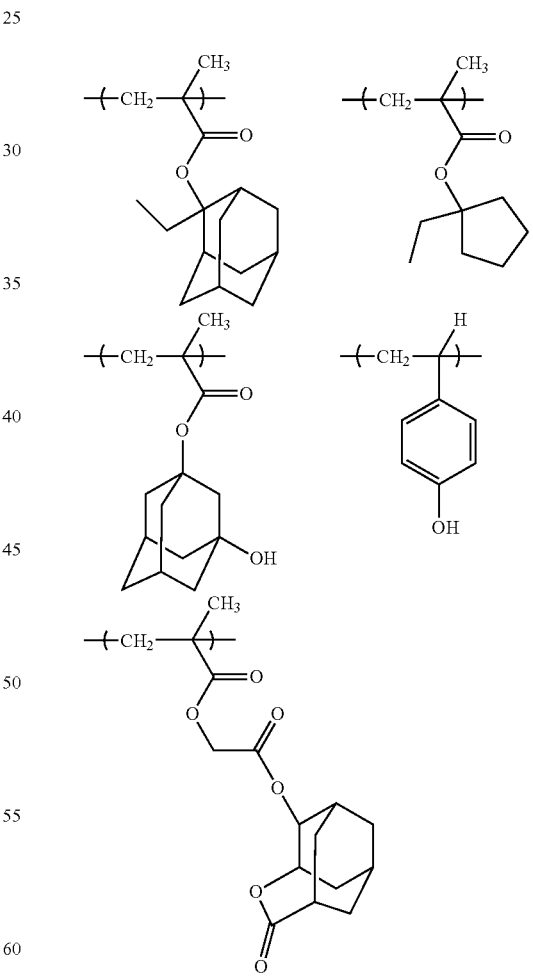

Resin Synthesis Example 3

The monomers (a5-1-1) and (a4-0-12) were mixed in a molar ratio of 50/50 (monomer (a5-1-1)/monomer (a4-0-

12)), and methylisobutylketone was added in 1.2 times parts based on total parts of all monomers to prepare a mixture. To the mixture, azobisisobutyronitrile was added as an initiator in a ratio of 3 mol % based on all monomer molar amount, and the obtained mixture was heated at 70° C. for about 5 hours. The reaction mixture obtained was poured into a large amount of a mixture of methanol and water to cause precipitation, followed by being filtrated. As a result, a polymer having a weight-average molecular weight of about 10,000 was obtained in a yield of 91%. The polymer had the following structural units. That resin is referred to as polymer X1.

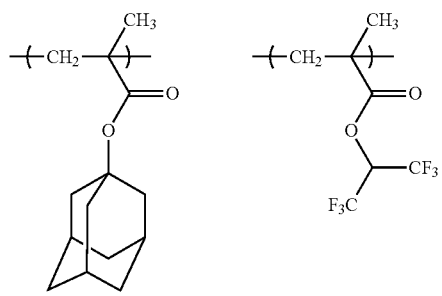

Examples 5 to 14 and Comparative Examples 1 to 3

<Producing Photoresist Compositions>

The following components as listed in the following table were mixed and dissolved in the solvent as mentioned below, and then filtrated through a fluorine resin filter having pore diameter of 0.2 μm, to prepare photoresist compositions.

TABLE 5

| Comp. No. | Resin (kind/ amount (part)) | Acid generator (kind/amount (part)) | Compound of formula (I) (kind/amount (part)) | Quencher (kind/ amount (part)) | PB (° C.)/ PEB (° C.) |
|---|---|---|---|---|---|
| 1 | X1/0.4 A1/10 | None | I-1/0.90 | D1/0.28 | 120/110 |
| 2 | X1/0.4 A1/10 | B1-21/0.30 B1-22/0.20 | I-1/0.40 | D1/0.28 | 120/110 |
| 3 | X1/0.4 A1/10 | B1-21/0.60 B1-22/0.40 | I-1/0.20 | D1/0.28 | 120/110 |
| 4 | X1/0.4 A2/10 | B1-21/0.30 B1-22/0.20 | I-1/0.40 | D1/0.28 | 120/110 |
| 5 | X1/0.4 A1/10 | None | I-3/0.90 | D1/0.28 | 120/110 |
| 6 | X1/0.4 A2/10 | B1-21/0.30 B1-22/0.20 | I-3/0.40 | D1/0.28 | 120/110 |
| 7 | X1/0.4 A1/10 | None | I-15/0.9 | D1/0.28 | 120/110 |
| 8 | X1/0.4 A2/10 | B1-21/0.30 B1-22/0.20 | I-15/0.4 | D1/0.28 | 120/110 |
| 9 | X1/0.4 A1/10 | None | I-16/0.9 | D1/0.28 | 120/110 |
| 10 | X1/0.4 A2/10 | B1-21/0.30 B1-22/0.20 | I-16/0.4 | D1/0.28 | 120/110 |
| Compar. comp 1 | X1/0.4 A1/10 | None | I-X1/0.9 | D1/0.28 | 120/110 |
| Compar. comp 2 | X1/0.4 A1/10 | None | I-X2/0.9 | D1/0.28 | 120/110 |
| Compar. comp 3 | X1/0.4 A1/10 | None | I-X3 1.9 | D1/0.28 | 120/110 |

In Table 5, each of characters represents the following component:

<Resin>

A1: Resin A1, A2: Resin A2, X1: Resin X1

<Acid Generator>

B1-21: Salt represented by formula (B1-21), produced according to the method as recited in JP2012-224611A1

B1-22: Salt represented by formula (B1-22), produced according to the method as recited in JP2012-224611A1

IX-1: Salt represented by formula (IX-1), produced according to the method as recited in JP2007-197718A1

IX-2: Salt represented by formula (IX-2), produced according to the method as recited in JP2007-145822A1

IX-3: Salt represented by formula (IX-3), produced according to the method as recited in JP2013-82893A1

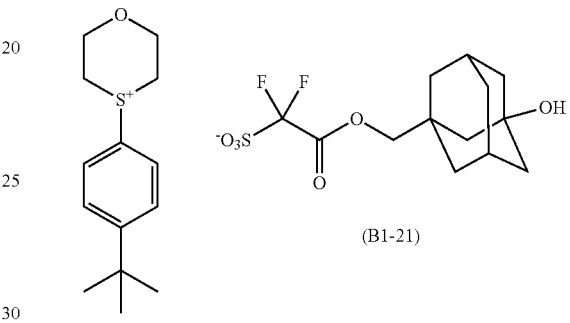

(B1-21)

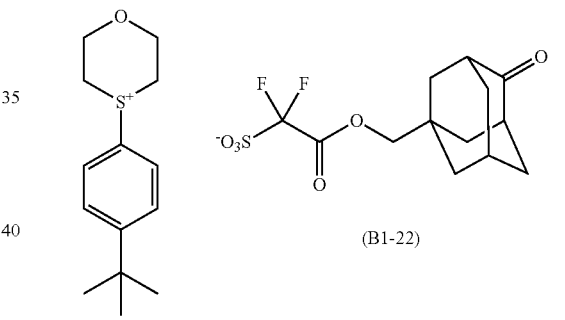

(B1-22)

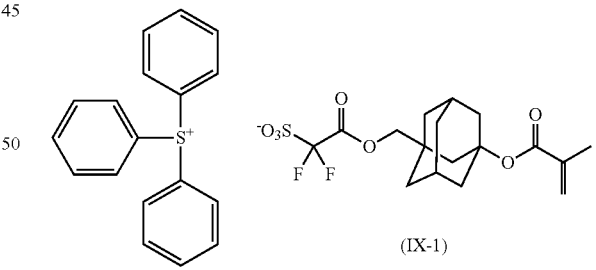

(IX-1)

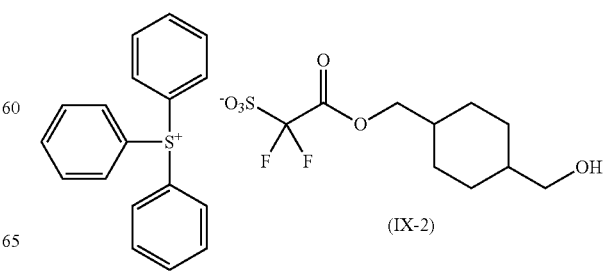

(IX-2)

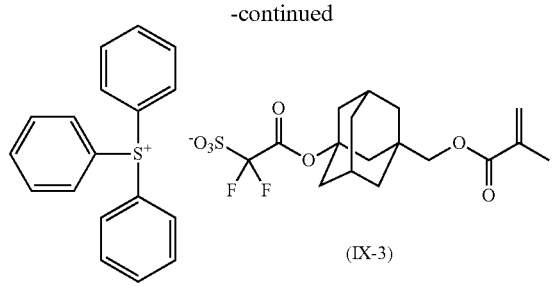

(IX-3)

<Salt of Formula (I)>
I-1: Salt represented by formula (I-1)
I-3: Salt represented by formula (I-3)
I-15: Salt represented by formula (I-15)
I-16: Salt represented by formula (I-16)
<Quencher>
D1: The compound of the following formula, which was manufactured by Tokyo Chemical Industries, Co., Ltd.

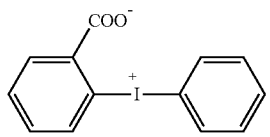

<Solvent>

| Mixture of the following solvents | |
|---|---|
| propyleneglycolmonomethylether acetate | 265 parts |
| propyleneglycolmonomethylether | 20 parts |
| 2-heptanone | 20 parts |
| γ-butyrolactone | 3.5 parts |

<Evaluation>

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 100 nm after drying. The silicon wafers thus coated with the respective photoresist compositions were each prebaked on a direct hotplate at the temperature as listed in the column "PB" of Table 5 for 60 seconds. Using an ArF excimer stepper (XT:1900G1 manufactured by ASML INC., NA=1.35, Annular $\sigma_{out}$=0.85 $\sigma_{in}$=0.65, X—Y polarization) and a mask for forming trench pattern (pitch: 120 nm, trench width: 40 nm), each wafer having the respective resist film was subjected to exposure, with the exposure quantity being varied stepwise.

After the exposure, each wafer was subjected to post-exposure baking on a hotplate at the temperature as listed in the column "PEB" of Table 5 for 60 seconds and then to development for 20 seconds at 23° C. with butyl acetate (Tokyo Chemical Industries, Co., Ltd.) in the manner of dynamic dispense method to produce a negative photoresist pattern.

In the following evaluation, effective sensitivity (ES) means the exposure quantity with which exposure using the above-mentioned mask provides a pattern with 40 nm of the trench width after development.

<Evaluation of Focus Margin [DOF]>

Negative photoresist patterns were produced in the same manner as described above except that exposure was conducted at the effective sensitivity with the focus point distance being varied stepwise.

The focus range where the resulting photoresist patterns exhibited a trench pattern width of 40 nm±5% (between 38 nm and 42 nm) was taken as DOF (nm).

The results were listed in Table 6.

TABLE 6

| Ex. No. | Composition No. | DOF (nm) |
|---|---|---|
| Ex. 5 | 1 | 90 |
| Ex. 6 | 2 | 120 |
| Ex. 7 | 3 | 105 |
| Ex. 8 | 4 | 135 |
| Ex. 9 | 5 | 105 |
| Ex. 10 | 6 | 150 |
| Ex. 11 | 7 | 105 |
| Ex. 12 | 8 | 150 |
| Ex. 13 | 9 | 105 |
| Ex. 14 | 10 | 135 |
| Comp. Ex. 1 | Compar. Comp.1 | 60 |
| Comp. Ex. 2 | Compar. Comp.2 | 45 |
| Comp. Ex. 3 | Compar. Comp.3 | 60 |

The salt of the present invention is useful as a component for a photoresist composition, and the photoresist composition containing the salt of the present invention can provide photoresist patterns with excellent DOF, which is suitable for fine processing of semiconductors.

What is claimed is:

1. A salt represented by formula (I):

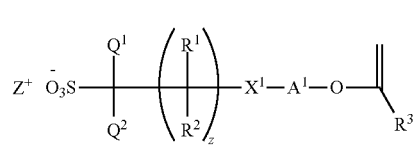

(I)

wherein $Q^1$ and $Q^2$ independently each represent a fluorine atom or a C1-C6 perfluoroalkyl group,
$R^1$ and $R^2$ independently each represent a hydrogen atom, a fluorine atom or a C1-C6 perfluoroalkyl group,
z represents an integer of 0 to 6,
$X^1$ represents *—C(=O)—O—, *—O—C(=O)—, *—O—C(=O)—O— or —O—, where * represents a binding site to —C($R^1$)($R^2$)— or —C($Q^1$)($Q^2$)-,
$A^1$ represents a C2-C36 divalent hydrocarbon group in which a hydrogen atom can be replaced by a substituent, said divalent hydrocarbon group having a C3-C18 alicyclic hydrocarbon group,
$R^3$ represents a hydrogen atom or a methyl group, and
$Z^+$ represents an organic cation.

2. The salt according to claim 1 wherein $X^1$ represents *—C(=O)—O—.

3. The salt according to claim 1 wherein $R^3$ is a hydrogen atom.

4. An acid generator comprising the salt according to claim 1.

5. A photoresist composition comprising the salt according to claim 1 as an acid generator and a resin which comprises a structural unit having an acid-labile group.

6. The photoresist composition according to claim 5 which further comprises a salt generating an acid weaker in acidity than an acid generated from the acid generator.

7. A process for producing a photoresist pattern comprising the following steps (1) to (5):
   (1) a step of applying the photoresist composition according to claim 5 on a substrate,
   (2) a step of forming a composition film by conducting drying,
   (3) a step of exposing a composition film to radiation,
   (4) a step of baking the exposed composition film, and
   (5) a step of developing the baked composition film with an alkaline developer, thereby forming a photoresist pattern.

* * * * *